US008805524B2

(12) United States Patent
Woods et al.

(10) Patent No.: US 8,805,524 B2
(45) Date of Patent: Aug. 12, 2014

(54) SYSTEM AND METHOD FOR DISPLAYING STIMULATION FIELD GENERATED BY ELECTRODE ARRAY

(75) Inventors: Carla Mann Woods, Los Angeles, CA (US); David K. L. Peterson, Saugus, CA (US); Paul M. Meadows, Glendale, CA (US); Gerald E. Loeb, South Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 107 days.

(21) Appl. No.: 13/361,669

(22) Filed: Jan. 30, 2012

(65) Prior Publication Data

US 2012/0130448 A1 May 24, 2012

Related U.S. Application Data

(63) Continuation of application No. 12/120,162, filed on May 13, 2008, now Pat. No. 8,121,701, and a continuation of application No. 11/158,670, filed on Jun. 21, 2005, now Pat. No. 7,555,346, and a continuation of application No. 10/641,905, filed on Aug. 15, 2003, now Pat. No. 6,909,917, and a continuation of application No. 10/150,679, filed on May 17, 2002, now Pat. No. 6,609,032, and a continuation of application No. 09/550,217, filed on Apr. 17, 2000, now Pat. No. 6,393,325, and a continuation-in-part of application No. 09/226,849, filed on Jan. 7, 1999, now Pat. No. 6,052,624.

(60) Provisional application No. 60/145,829, filed on Jul. 27, 1999, provisional application No. 60/172,167, filed on Dec. 17, 1999.

(51) Int. Cl.
*A61N 1/08* (2006.01)

(52) U.S. Cl.
USPC .................................. 607/59; 607/60; 607/46

(58) Field of Classification Search
USPC ................................................ 607/59–60, 46
See application file for complete search history.

(56) References Cited

U.S. PATENT DOCUMENTS 3,646,940 A 3/1972 Timm et al.
3,822,708 A 7/1974 Zilber (Continued)

FOREIGN PATENT DOCUMENTS

WO WO 01/15773 3/2001

OTHER PUBLICATIONS

Office Action dated Nov. 8, 2007 in U.S. Appl. No. 11/158,670, filed Jun. 21, 2005, inventor: Carla Mann Woods, (9pages).

(Continued)

*Primary Examiner* — Joseph Stoklosa
(74) *Attorney, Agent, or Firm* — Vista IP Law Group LLP

(57) ABSTRACT

An implantable pulse generator includes a current steering capability that allows a clinician or patient to quickly determine a desired electrode stimulation pattern, including which electrodes of a group of electrodes within an electrode array should receive a stimulation current, including the amplitude, width and pulse repetition rate of such current. Movement of the selected group of electrodes is facilitated through the use of remotely generated directional signals, generated by a pointing device, such as a joystick. As movement of the selected group of electrodes occurs, current redistribution amongst the various electrode contacts takes place. The redistribution of stimulus amplitudes utilizes re-normalization of amplitudes so that the perceptual level remains fairly constant. This prevents the resulting paresthesia from falling below the perceptual threshold or above the comfort threshold.

24 Claims, 40 Drawing Sheets

(56) References Cited

U.S. PATENT DOCUMENTS

| | | | | |
|---|---|---|---|---|
| 4,019,518 | A | 4/1977 | Maurer et al. | |
| 4,331,283 | A | 5/1982 | Fraser | |
| 4,520,825 | A | 6/1985 | Thompson et al. | |
| 4,653,109 | A | 3/1987 | Lemelson et al. | |
| 4,793,353 | A | 12/1988 | Borkan | |
| 5,036,850 | A | 8/1991 | Owens | |
| 5,167,229 | A | 12/1992 | Peckham et al. | |
| 5,311,449 | A | 5/1994 | Adams | |
| 5,354,320 | A | 10/1994 | Schaldach et al. | |
| 5,370,672 | A * | 12/1994 | Fowler et al. | 607/58 |
| 5,417,719 | A | 5/1995 | Hull et al. | |
| 5,443,486 | A | 8/1995 | Hrdlicka et al. | |
| 5,501,703 | A | 3/1996 | Holsheimer et al. | |
| 5,601,617 | A | 2/1997 | Loeb et al. | |
| 5,626,629 | A | 5/1997 | Faltys et al. | |
| 5,643,330 | A | 7/1997 | Holsheimer et al. | |
| 5,649,970 | A | 7/1997 | Loeb et al. | |
| 5,674,264 | A | 10/1997 | Carter et al. | |
| 5,713,922 | A | 2/1998 | King | |
| 5,776,171 | A | 7/1998 | Peckham et al. | |
| 5,776,172 | A | 7/1998 | Schulman et al. | |
| 5,800,465 | A | 9/1998 | Thompson et al. | |
| 5,814,092 | A | 9/1998 | King | |
| 5,833,623 | A | 11/1998 | Mann et al. | |
| 5,893,883 | A | 4/1999 | Torgerson et al. | |
| 5,895,416 | A | 4/1999 | Barreras, Sr. et al. | |
| 5,913,882 | A | 6/1999 | King | |
| 5,938,690 | A | 8/1999 | Law et al. | |
| 5,941,906 | A | 8/1999 | Barreras, Sr. et al. | |
| 6,035,237 | A | 3/2000 | Schulman et al. | |
| 6,052,624 | A | 4/2000 | Mann | |
| 6,289,247 | B1 * | 9/2001 | Faltys et al. | 607/57 |
| 6,308,102 | B1 | 10/2001 | Sieracki et al. | |
| 6,353,762 | B1 | 3/2002 | Baudino et al. | |
| 6,393,325 | B1 | 5/2002 | Mann et al. | |
| 6,609,032 | B1 | 8/2003 | Woods et al. | |
| 6,622,048 | B1 | 9/2003 | Mann et al. | |
| 6,909,917 | B2 | 6/2005 | Woods et al. | |
| 7,499,048 | B2 | 3/2009 | Sieracki et al. | |
| 7,555,346 | B1 | 6/2009 | Woods et al. | |
| 7,623,918 | B2 | 11/2009 | Goetz | |
| 7,657,319 | B2 | 2/2010 | Goetz et al. | |
| 7,848,802 | B2 | 12/2010 | Goetz et al. | |
| 7,930,030 | B2 | 4/2011 | Woods et al. | |
| 2003/0139781 | A1 | 7/2003 | Bradley et al. | |
| 2004/0082980 | A1 | 4/2004 | Mouine et al. | |
| 2004/0098063 | A1 | 5/2004 | Goetz | |
| 2008/0039738 | A1 | 2/2008 | Dinsmoor et al. | |
| 2008/0221637 | A1 | 9/2008 | Woods et al. | |
| 2009/0240302 | A1 | 9/2009 | Woods et al. | |
| 2011/0060386 | A1 | 3/2011 | Woods et al. | |

OTHER PUBLICATIONS

Office Action dated Apr. 25, 2008 in U.S. Appl. No. 11/158,670, filed Jun. 21, 2005, inventor: Carla Mann Woods, (8pages).

Office Action dated Oct. 20, 2008 in U.S. Appl. No. 11/158,670, filed Jun. 21, 2005, inventor: Carla Mann Woods, (9pages).

Notice of Allowance dated Feb. 24, 2009 in U.S. Appl. No. 11/158,670, filed Jun. 21, 2005, inventor: Carla Mann Woods, (6pages).

* cited by examiner

INPUT MECHANISM CONTROLLED BY THE USER

| | LEFT + | LEFT − | RIGHT + | RIGHT − |
|---|---|---|---|---|
| 1 | 1.0 | −1.0 | | |
| 2 | 0.9 | −1.0 | 0.1 | |
| 3 | 0.8 | −1.0 | 0.2 | |
| 4 | 0.7 | −1.0 | 0.3 | |
| 5 | 0.6 | −1.0 | 0.4 | |
| 6 | 0.5 | −1.0 | 0.5 | |
| 7 | 0.4 | −1.0 | 0.6 | |
| 8 | 0.3 | −1.0 | 0.7 | |
| 9 | 0.2 | −1.0 | 0.8 | |
| 10 | 0.1 | −1.0 | 0.9 | |
| 11 | | −1.0 | 1.0 | |
| 12 | 0.1 | −0.9 | 0.9 | −0.1 |
| 13 | 0.2 | −0.8 | 0.8 | −0.2 |
| 14 | 0.3 | −0.7 | 0.7 | −0.3 |
| 15 | 0.4 | −0.6 | 0.6 | −0.4 |
| 16 | 0.5 | −0.5 | 0.5 | −0.5 |
| 17 | 0.6 | −0.4 | 0.4 | −0.6 |
| 18 | 0.7 | −0.3 | 0.3 | −0.7 |
| 19 | 0.8 | −0.2 | 0.2 | −0.8 |
| 20 | 0.9 | −0.1 | 0.1 | −0.9 |
| 21 | 1.0 | | | −1.0 |
| 22 | 0.9 | | 0.1 | −1.0 |
| 23 | 0.8 | | 0.2 | −1.0 |
| 24 | 0.7 | | 0.3 | −1.0 |
| 25 | 0.6 | | 0.4 | −1.0 |
| 26 | 0.5 | | 0.5 | −1.0 |
| 27 | 0.4 | | 0.6 | −1.0 |
| 28 | 0.3 | | 0.7 | −1.0 |
| 29 | 0.2 | | 0.8 | −1.0 |
| 30 | 0.1 | | 0.9 | −1.0 |
| 31 | | | 1.0 | −1.0 |

FIG. 7

| | CASE | CASE | E1 | E2 | E3 | E4 | E5 | E6 | E7 | E8 | CASE | CASE |
|---|---|---|---|---|---|---|---|---|---|---|---|---|
| 1 | 1.0 | | −1.0 | | | | | | | | | |
| 2 | 0.9 | | −1.0 | | 0.1 | | | | | | | |
| 3 | 0.8 | | −1.0 | | 0.2 | | | | | | | |
| 4 | 0.7 | | −1.0 | | 0.3 | | | | | | | |
| 5 | 0.6 | | −1.0 | | 0.4 | | | | | | | |
| 6 | 0.5 | | −1.0 | | 0.5 | | | | | | | |
| 7 | 0.4 | | −1.0 | | 0.6 | | | | | | | |
| 8 | 0.3 | | −1.0 | | 0.7 | | | | | | | |
| 9 | 0.2 | | −1.0 | | 0.8 | | | | | | | |
| 10 | 0.1 | | −1.0 | | 0.9 | | | | | | | |
| 11 | | | −1.0 | | 1.0 | | | | | | | |
| 12 | | | −1.0 | | 0.9 | 0.1 | | | | | | |
| 13 | | | −1.0 | | 0.8 | 0.2 | | | | | | |
| 14 | | | −1.0 | | 0.7 | 0.3 | | | | | | |
| 15 | | | −1.0 | | 0.6 | 0.4 | | | | | | |
| 16 | | | −1.0 | | 0.5 | 0.5 | | | | | | |
| 17 | | | −1.0 | | 0.4 | 0.6 | | | | | | |
| 18 | | | −1.0 | | 0.3 | 0.7 | | | | | | |
| 19 | | | −1.0 | | 0.2 | 0.8 | | | | | | |
| 20 | | | −1.0 | | 0.1 | 0.9 | | | | | | |

FIG. 8A

| | CASE | CASE | E1 | E2 | E3 | E4 | E5 | E6 | E7 | E8 | CASE | CASE |
|---|---|---|---|---|---|---|---|---|---|---|---|---|
| 21 | | | −1.0 | | | 1.0 | | | | | | |
| 22 | 0.1 | | −0.9 | −0.1 | | 0.9 | | | | | | |
| 23 | 0.2 | | −0.8 | −0.2 | | 0.8 | | | | | | |
| 24 | 0.3 | | −0.7 | −0.3 | | 0.7 | | | | | | |
| 25 | 0.4 | | −0.6 | −0.4 | | 0.6 | | | | | | |
| 26 | 0.5 | | −0.5 | −0.5 | | 0.5 | | | | | | |
| 27 | 0.6 | | −0.4 | −0.6 | | 0.4 | | | | | | |
| 28 | 0.7 | | −0.3 | −0.7 | | 0.3 | | | | | | |
| 29 | 0.8 | | −0.2 | −0.8 | | 0.2 | | | | | | |
| 30 | 0.9 | | −0.1 | −0.9 | | 0.1 | | | | | | |
| 31 | 1.0 | | | −1.0 | | | | | | | | |
| 32 | 0.9 | 0.1 | | −1.0 | | | | | | | | |
| 33 | 0.8 | 0.2 | | −1.0 | | | | | | | | |
| 34 | 0.7 | 0.3 | | −1.0 | | | | | | | | |
| 35 | 0.6 | 0.4 | | −1.0 | | | | | | | | |
| 36 | 0.5 | 0.5 | | −1.0 | | | | | | | | |
| 37 | 0.4 | 0.6 | | −1.0 | | | | | | | | |
| 38 | 0.3 | 0.7 | | −1.0 | | | | | | | | |
| 39 | 0.2 | 0.8 | | −1.0 | | | | | | | | |
| 40 | 0.1 | 0.9 | | −1.0 | | | | | | | | |

FIG. 8B

| | CASE | CASE | E1 | E2 | E3 | E4 | E5 | E6 | E7 | E8 | CASE | CASE |
|---|---|---|---|---|---|---|---|---|---|---|---|---|
| 41 | | 1.0 | | -1.0 | | | | | | | | |
| 42 | | 0.9 | | -1.0 | | 0.1 | | | | | | |
| 43 | | 0.8 | | -1.0 | | 0.2 | | | | | | |
| 44 | | 0.7 | | -1.0 | | 0.3 | | | | | | |
| 45 | | 0.6 | | -1.0 | | 0.4 | | | | | | |
| 46 | | 0.5 | | -1.0 | | 0.5 | | | | | | |
| 47 | | 0.4 | | -1.0 | | 0.6 | | | | | | |
| 48 | | 0.3 | | -1.0 | | 0.7 | | | | | | |
| 49 | | 0.2 | | -1.0 | | 0.8 | | | | | | |
| 50 | | 0.1 | | -1.0 | | 0.9 | | | | | | |
| 51 | | | | -1.0 | | 1.0 | | | | | | |
| 52 | | | | -1.0 | | 0.9 | 0.1 | | | | | |
| 53 | | | | -1.0 | | 0.8 | 0.2 | | | | | |
| 54 | | | | -1.0 | | 0.7 | 0.3 | | | | | |
| 55 | | | | -1.0 | | 0.6 | 0.4 | | | | | |
| 56 | | | | -1.0 | | 0.5 | 0.5 | | | | | |
| 57 | | | | -1.0 | | 0,4 | 0.6 | | | | | |
| 58 | | | | -1.0 | | 0.3 | 0.7 | | | | | |
| 59 | | | | -1.0 | | 0.2 | 0.8 | | | | | |
| 60 | | | | -1.0 | | 0.1 | 0.9 | | | | | |

FIG. 8C

| | CASE | CASE | E1 | E2 | E3 | E4 | E5 | E6 | E7 | E8 | CASE | CASE |
|---|---|---|---|---|---|---|---|---|---|---|---|---|
| 61 | | | | -1.0 | | | 1.0 | | | | | |
| 62 | | 0.1 | | -0.9 | -0.1 | | 0.9 | | | | | |
| 63 | | 0.2 | | -0.8 | -0.2 | | 0.8 | | | | | |
| 64 | | 0.3 | | -0.7 | -0.3 | | 0.7 | | | | | |
| 65 | | 0.4 | | -0.6 | -0.4 | | 0.6 | | | | | |
| 66 | | 0.5 | | -0.5 | -0.5 | | 0.5 | | | | | |
| 67 | | 0.6 | | -0.4 | -0.6 | | 0.4 | | | | | |
| 68 | | 0.7 | | -0.3 | -0.7 | | 0.3 | | | | | |
| 69 | | 0.8 | | -0.2 | -0.8 | | 0.2 | | | | | |
| 70 | | 0.9 | | -0.1 | -0.9 | | 0.1 | | | | | |
| 71 | | 1.0 | | | -1.0 | | | | | | | |
| 72 | | 0.9 | 0.1 | | -1.0 | | | | | | | |
| 73 | | 0.8 | 0.2 | | -1.0 | | | | | | | |
| 74 | | 0.7 | 0.3 | | -1.0 | | | | | | | |
| 75 | | 0.6 | 0.4 | | -1.0 | | | | | | | |
| 76 | | 0.5 | 0.5 | | -1.0 | | | | | | | |
| 77 | | 0.4 | 0.6 | | -1.0 | | | | | | | |
| 78 | | 0.3 | 0.7 | | -1.0 | | | | | | | |
| 79 | | 0.2 | 0.8 | | -1.0 | | | | | | | |
| 80 | | 0.1 | 0.9 | | -1.0 | | | | | | | |

FIG. 8D

| | CASE | CASE | E1 | E2 | E3 | E4 | E5 | E6 | E7 | E8 | CASE | CASE |
|---|---|---|---|---|---|---|---|---|---|---|---|---|
| 81 | | | 1.0 | | −1.0 | | | | | | | |
| 82 | | | 0.9 | | −1.0 | | 0.1 | | | | | |
| 83 | | | 0.8 | | −1.0 | | 0.2 | | | | | |
| 84 | | | 0.7 | | −1.0 | | 0.3 | | | | | |
| 85 | | | 0.6 | | −1.0 | | 0.4 | | | | | |
| 86 | | | 0.5 | | −1.0 | | 0.5 | | | | | |
| 87 | | | 0.4 | | −1.0 | | 0.6 | | | | | |
| 88 | | | 0.3 | | −1.0 | | 0.7 | | | | | |
| 89 | | | 0.2 | | −1.0 | | 0.8 | | | | | |
| 90 | | | 0.1 | | −1.0 | | 0.9 | | | | | |
| 91 | | | | | −1.0 | | 1.0 | | | | | |
| 92 | | | | | −1.0 | | 0.9 | 0.1 | | | | |
| 93 | | | | | −1.0 | | 0.8 | 0.2 | | | | |
| 94 | | | | | −1.0 | | 0.7 | 0.3 | | | | |
| 95 | | | | | −1.0 | | 0.6 | 0.4 | | | | |
| 96 | | | | | −1.0 | | 0.5 | 0.5 | | | | |
| 97 | | | | | −1.0 | | 0.4 | 0.6 | | | | |
| 98 | | | | | −1.0 | | 0.3 | 0.7 | | | | |
| 99 | | | | | −1.0 | | 0.2 | 0.8 | | | | |
| 100 | | | | | −1.0 | | 0.1 | 0.9 | | | | |

FIG. 8E

| | CASE | CASE | E1 | E2 | E3 | E4 | E5 | E6 | E7 | E8 | CASE | CASE |
|---|---|---|---|---|---|---|---|---|---|---|---|---|
| 101 | | | | | −1.0 | | | 1.0 | | | | |
| 102 | | | 0.1 | | −0.9 | −0.1 | | 0.9 | | | | |
| 103 | | | 0.2 | | −0.8 | −0.2 | | 0.8 | | | | |
| 104 | | | 0.3 | | −0.7 | −0.3 | | 0.7 | | | | |
| 105 | | | 0.4 | | −0.6 | −0.4 | | 0.6 | | | | |
| 106 | | | 0.5 | | −0.5 | −0.5 | | 0.5 | | | | |
| 107 | | | 0.6 | | −0.4 | −0.6 | | 0.4 | | | | |
| 108 | | | 0.7 | | −0.3 | −0.7 | | 0.3 | | | | |
| 109 | | | 0.8 | | −0.2 | −0.8 | | 0.2 | | | | |
| 110 | | | 0.9 | | −0.1 | −0.9 | | 0.1 | | | | |
| 111 | | | 1.0 | | | −1.0 | | | | | | |
| 112 | | | 0.9 | 0.1 | | −1.0 | | | | | | |
| 113 | | | 0.8 | 0.2 | | −1.0 | | | | | | |
| 114 | | | 0.7 | 0.3 | | −1.0 | | | | | | |
| 115 | | | 0.6 | 0.4 | | −1.0 | | | | | | |
| 116 | | | 0.5 | 0.5 | | −1.0 | | | | | | |
| 117 | | | 0.4 | 0.6 | | −1.0 | | | | | | |
| 118 | | | 0.3 | 0.7 | | −1.0 | | | | | | |
| 119 | | | 0.2 | 0.8 | | −1.0 | | | | | | |
| 120 | | | 0.1 | 0.9 | | −1.0 | | | | | | |

FIG. 8F

| | CASE | CASE | E1 | E2 | E3 | E4 | E5 | E6 | E7 | E8 | CASE | CASE |
|---|---|---|---|---|---|---|---|---|---|---|---|---|
| 141 | | | | | | −1.0 | | | 1.0 | | | |
| 142 | | | | 0.1 | | −0.9 | −0.1 | | 0.9 | | | |
| 143 | | | | 0.2 | | −0.8 | −0.2 | | 0.8 | | | |
| 144 | | | | 0.3 | | −0.7 | −0.3 | | 0.7 | | | |
| 145 | | | | 0.4 | | −0.6 | −0.4 | | 0.6 | | | |
| 146 | | | | 0.5 | | −0.5 | −0.5 | | 0.5 | | | |
| 147 | | | | 0.6 | | −0.4 | −0.6 | | 0.4 | | | |
| 148 | | | | 0.7 | | −0.3 | −0.7 | | 0.3 | | | |
| 149 | | | | 0.8 | | −0.2 | −0.8 | | 0.2 | | | |
| 150 | | | | 0.9 | | −0.1 | −0.9 | | 0.1 | | | |
| 151 | | | | 1.0 | | | −1.0 | | | | | |
| 152 | | | | 0.9 | 0.1 | | −1.0 | | | | | |
| 153 | | | | 0.8 | 0.2 | | −1.0 | | | | | |
| 154 | | | | 0.7 | 0.3 | | −1.0 | | | | | |
| 155 | | | | 0.6 | 0.4 | | −1.0 | | | | | |
| 156 | | | | 0.5 | 0.5 | | −1.0 | | | | | |
| 157 | | | | 0.4 | 0.6 | | −1.0 | | | | | |
| 158 | | | | 0.3 | 0.7 | | −1.0 | | | | | |
| 159 | | | | 0.2 | 0.8 | | −1.0 | | | | | |
| 160 | | | | | 0.9 | | −1.0 | | | | | |

FIG. 8H

| | CASE | CASE | E1 | E2 | E3 | E4 | E5 | E6 | E7 | E8 | CASE | CASE |
|---|---|---|---|---|---|---|---|---|---|---|---|---|
| 161 | | | | | 1.0 | | -1.0 | | | | | |
| 162 | | | | | 0.9 | | -1.0 | | 0.1 | | | |
| 163 | | | | | 0.8 | | -1.0 | | 0.2 | | | |
| 164 | | | | | 0.7 | | -1.0 | | 0.3 | | | |
| 165 | | | | | 0.6 | | -1.0 | | 0.4 | | | |
| 166 | | | | | 0.5 | | -1.0 | | 0.5 | | | |
| 167 | | | | | 0.4 | | -1.0 | | 0.6 | | | |
| 168 | | | | | 0.3 | | -1.0 | | 0.7 | | | |
| 169 | | | | | 0.2 | | -1.0 | | 0.8 | | | |
| 170 | | | | | 0.1 | | -1.0 | | 0.9 | | | |
| 171 | | | | | | | -1.0 | | 1.0 | | | |
| 172 | | | | | | | -1.0 | | 0.9 | 0.1 | | |
| 173 | | | | | | | -1.0 | | 0.8 | 0.2 | | |
| 174 | | | | | | | -1.0 | | 0.7 | 0.3 | | |
| 175 | | | | | | | -1.0 | | 0.6 | 0.4 | | |
| 176 | | | | | | | -1.0 | | 0.5 | 0.5 | | |
| 177 | | | | | | | -1.0 | | 0.4 | 0.6 | | |
| 178 | | | | | | | -1.0 | | 0.3 | 0.7 | | |
| 179 | | | | | | | -1.0 | | 0.2 | 0.8 | | |
| 180 | | | | | | | -1.0 | | 0.1 | 0.9 | | |

FIG. 8J

| | CASE | CASE | E1 | E2 | E3 | E4 | E5 | E6 | E7 | E8 | CASE | CASE |
|---|---|---|---|---|---|---|---|---|---|---|---|---|
| 181 | | | | | | | −1.0 | | | 1.0 | | |
| 182 | | | | | 0.1 | | −0.9 | −0.1 | | 0.9 | | |
| 183 | | | | | 0.2 | | −0.8 | −0.2 | | 0.8 | | |
| 184 | | | | | 0.3 | | −0.7 | −0.3 | | 0.7 | | |
| 185 | | | | | 0.4 | | −0.6 | −0.4 | | 0.6 | | |
| 186 | | | | | 0.5 | | −0.5 | −0.5 | | 0.5 | | |
| 187 | | | | | 0.6 | | −0.4 | −0.6 | | 0.4 | | |
| 188 | | | | | 0.7 | | −0.3 | −0.7 | | 0.3 | | |
| 189 | | | | | 0.8 | | −0.2 | −0.8 | | 0.2 | | |
| 190 | | | | | 0.9 | | −0.1 | −0.9 | | 0.1 | | |
| 191 | | | | | 1.0 | | | −1.0 | | | | |
| 192 | | | | | 0.9 | 0.1 | | −1.0 | | | | |
| 193 | | | | | 0.8 | 0.2 | | −1.0 | | | | |
| 194 | | | | | 0.7 | 0.3 | | −1.0 | | | | |
| 195 | | | | | 0.6 | 0.4 | | −1.0 | | | | |
| 196 | | | | | 0.5 | 0.5 | | −1.0 | | | | |
| 197 | | | | | 0.4 | 0.6 | | −1.0 | | | | |
| 198 | | | | | 0.3 | 0.7 | | −1.0 | | | | |
| 199 | | | | | 0.2 | 0.8 | | −1.0 | | | | |
| 200 | | | | | 0.1 | 0.9 | | −1.0 | | | | |

FIG. 8K

| | CASE | CASE | E1 | E2 | E3 | E4 | E5 | E6 | E7 | E8 | CASE | CASE |
|---|---|---|---|---|---|---|---|---|---|---|---|---|
| 201 | | | | | | 1.0 | | −1.0 | | | | |
| 202 | | | | | | 0.9 | | −1.0 | | 0.1 | | |
| 203 | | | | | | 0.8 | | −1.0 | | 0.2 | | |
| 204 | | | | | | 0.7 | | −1.0 | | 0.3 | | |
| 205 | | | | | | 0.6 | | −1.0 | | 0.4 | | |
| 206 | | | | | | 0.5 | | −1.0 | | 0.5 | | |
| 207 | | | | | | 0.4 | | −1.0 | | 0.6 | | |
| 208 | | | | | | 0.3 | | −1.0 | | 0.7 | | |
| 209 | | | | | | 0.2 | | −1.0 | | 0.8 | | |
| 210 | | | | | | 0.1 | | −1.0 | | 0.9 | | |
| 211 | | | | | | | | −1.0 | | 1.0 | | |
| 212 | | | | | | | | −1.0 | | 0.9 | 0.1 | |
| 213 | | | | | | | | −1.0 | | 0.8 | 0.2 | |
| 214 | | | | | | | | −1.0 | | 0.7 | 0.3 | |
| 215 | | | | | | | | −1.0 | | 0.6 | 0.4 | |
| 216 | | | | | | | | −1.0 | | 0.5 | 0.5 | |
| 217 | | | | | | | | −1.0 | | 0.4 | 0.6 | |
| 218 | | | | | | | | −1.0 | | 0.3 | 0.7 | |
| 219 | | | | | | | | −1.0 | | 0.2 | 0.8 | |
| 220 | | | | | | | | −1.0 | | 0.1 | 0.9 | |

FIG. 8L

| | CASE | CASE | E1 | E2 | E3 | E4 | E5 | E6 | E7 | E8 | CASE | CASE |
|---|---|---|---|---|---|---|---|---|---|---|---|---|
| 221 | | | | | | 0.1 | | | | 1.0 | | |
| 222 | | | | | | 0.2 | | | -0.1 | 0.9 | | |
| 223 | | | | | | 0.3 | | | -0.2 | 0.8 | | |
| 224 | | | | | | 0.4 | | | -0.3 | 0.7 | | |
| 225 | | | | | | 0.5 | | | -0.4 | 0.6 | | |
| 226 | | | | | | 0.6 | | | -0.5 | 0.5 | | |
| 227 | | | | | | 0.7 | | | -0.6 | 0.4 | | |
| 228 | | | | | | 0.8 | | | -0.7 | 0.3 | | |
| 229 | | | | | | 0.9 | | | -0.8 | 0.2 | | |
| 230 | | | | | | 1.0 | | -1.0 | -0.9 | 0.1 | | |
| 231 | | | | | | 0.9 | 0.1 | -0.9 | -1.0 | | | |
| 232 | | | | | | 0.8 | 0.2 | -0.8 | -1.0 | | | |
| 233 | | | | | | 0.7 | 0.3 | -0.7 | -1.0 | | | |
| 234 | | | | | | 0.6 | 0.4 | -0.6 | -1.0 | | | |
| 235 | | | | | | 0.5 | 0.5 | -0.5 | -1.0 | | | |
| 236 | | | | | | 0.4 | 0.6 | -0.4 | -1.0 | | | |
| 237 | | | | | | 0.3 | 0.7 | -0.3 | -1.0 | | | |
| 238 | | | | | | 0.2 | 0.8 | -0.2 | -1.0 | | | |
| 239 | | | | | | 0.1 | 0.9 | -0.1 | -1.0 | | | |
| 240 | | | | | | | | | -1.0 | | | |

| CASE | CASE | E1 | E2 | E3 | E4 | E5 | E6 | E7 | E8 | CASE | CASE |
|------|------|----|----|----|----|----|----|----|----|------|------|
| 241  |      |    |    |    |    |     |    |      |    |      |      |
| 242  |      |    |    |    |    | 1.0 |    | -1.0 |    |      |      |
| 243  |      |    |    |    |    | 0.9 |    | -1.0 | 0.1 |     |      |
| 244  |      |    |    |    |    | 0.8 |    | -1.0 | 0.2 |     |      |
| 245  |      |    |    |    |    | 0.7 |    | -1.0 | 0.3 |     |      |
| 246  |      |    |    |    |    | 0.6 |    | -1.0 | 0.4 |     |      |
| 247  |      |    |    |    |    | 0.5 |    | -1.0 | 0.5 |     |      |
| 248  |      |    |    |    |    | 0.4 |    | -1.0 | 0.6 |     |      |
| 249  |      |    |    |    |    | 0.3 |    | -1.0 | 0.7 |     |      |
| 250  |      |    |    |    |    | 0.2 |    | -1.0 | 0.8 |     |      |
| 251  |      |    |    |    |    | 0.1 |    | -1.0 | 0.9 |     |      |
| 252  |      |    |    |    |    |     |    | -1.0 | 1.0 |     |      |
| 253  |      |    |    |    |    |     |    | -1.0 | 0.9 | 0.1 |      |
| 254  |      |    |    |    |    |     |    | -1.0 | 0.8 | 0.2 |      |
| 255  |      |    |    |    |    |     |    | -1.0 | 0.7 | 0.3 |      |
| 256  |      |    |    |    |    |     |    | -1.0 | 0.6 | 0.4 |      |
| 257  |      |    |    |    |    |     |    | -1.0 | 0.5 | 0.5 |      |
| 258  |      |    |    |    |    |     |    | -1.0 | 0.4 | 0.6 |      |
| 258  |      |    |    |    |    |     |    | -1.0 | 0.3 | 0.7 |      |
| 258  |      |    |    |    |    |     |    | -1.0 | 0.2 | 0.8 |      |
| 260  |      |    |    |    |    |     |    | -1.0 | 0.1 | 0.9 |      |

| | CASE | CASE | E1 | E2 | E3 | E4 | E5 | E6 | E7 | E8 | CASE | CASE |
|---|---|---|---|---|---|---|---|---|---|---|---|---|
| 261 | | | | | | | | | −1.0 | −1.0 | | 1.0 |
| 262 | | | | | | | 0.1 | | −0.9 | −1.0 | | 0.9 |
| 263 | | | | | | | 0.2 | | −0.8 | −1.0 | | 0.8 |
| 264 | | | | | | | 0.3 | | −0.7 | −1.0 | | 0.7 |
| 265 | | | | | | | 0.4 | | −0.6 | −1.0 | | 0.6 |
| 266 | | | | | | | 0.5 | | −0.5 | −1.0 | | 0.5 |
| 267 | | | | | | | 0.6 | | −0.4 | −1.0 | | 0.4 |
| 268 | | | | | | | 0.7 | | −0.3 | −1.0 | | 0.3 |
| 269 | | | | | | | 0.8 | | −0.2 | −1.0 | | 0.2 |
| 270 | | | | | | | 0.9 | | −0.1 | −1.0 | | 0.1 |
| 271 | | | | | | | 1.0 | | | −1.0 | | |
| 272 | | | | | | | 0.9 | 0.1 | | −1.0 | | |
| 273 | | | | | | | 0.8 | 0.2 | | −1.0 | | |
| 274 | | | | | | | 0.7 | 0.3 | | −1.0 | | |
| 275 | | | | | | | 0.6 | 0.4 | | −1.0 | | |
| 276 | | | | | | | 0.5 | 0.5 | | −1.0 | | |
| 277 | | | | | | | 0.4 | 0.6 | | −1.0 | | |
| 278 | | | | | | | 0.3 | 0.7 | | −1.0 | | |
| 279 | | | | | | | 0.2 | 0.8 | | −1.0 | | |
| 280 | | | | | | | 0.1 | 0.9 | | −1.0 | | |

FIG. 8P

| CASE | E1 | E2 | E3 | E4 | E5 | E6 | E7 | E8 | CASE | CASE |
|------|----|----|----|----|----|----|----|----|------|------|
| 281 | | | | | | | | | | |
| 282 | | | | | | 1.0 | | −1.0 | | 0.1 |
| 283 | | | | | | 0.9 | | −1.0 | | 0.2 |
| 284 | | | | | | 0.8 | | −1.0 | | 0.3 |
| 285 | | | | | | 0.7 | | −1.0 | | 0.4 |
| 286 | | | | | | 0.6 | | −1.0 | | 0.5 |
| 287 | | | | | | 0.5 | | −1.0 | | 0.6 |
| 288 | | | | | | 0.4 | | −1.0 | | 0.7 |
| 289 | | | | | | 0.3 | | −1.0 | | 0.8 |
| 290 | | | | | | 0.2 | | −1.0 | | 0.9 |
| 291 | | | | | | 0.1 | | −1.0 | | 1.0 |

SYSTEM AND METHOD FOR DISPLAYING STIMULATION FIELD GENERATED BY ELECTRODE ARRAY

This application is a continuation of U.S. patent application Ser. No. 12/120,162, filed May 13, 2008, now U.S. Pat. No. 8,121,701; which application is a continuation of U.S. patent application Ser. No. 11/158,670, filed Jun. 21, 2005, now U.S. Pat. No. 7,555,346; which application is a continuation of U.S. application Ser. No. 10/641,905, filed Aug. 15, 2003, now U.S. Pat. No. 6,909,917; which application is a continuation of U.S. application Ser. No. 10/150,679, filed May 17, 2002, now U.S. Pat. No. 6,609,032; which application is a continuation of Ser. No. 09/550,217, filed Apr. 17, 2000, now U.S. Pat. No. 6,393,325; which application is a continuation-in-part of U.S. patent application Ser. No. 09/226,849, filed Jan. 7, 1999, now U.S. Pat. No. 6,052,624; which application claims the benefit of the following U.S. Provisional Applications: Ser. No. 60/145,829, filed Jul. 27, 1999, and Ser. No. 60/172,167, filed Dec. 17, 1999; which applications and patents are incorporated herein by reference.

BACKGROUND OF THE INVENTION

The present invention relates to a device for programming an implantable electrode array used with an implantable stimulator. More particularly, one embodiment of the invention relates to a device used to provide directional programming for the implantable electrode array associated with an implantable stimulator that electrically stimulates the spinal cord for the purposes of controlling and reducing pain.

Within the past several years, rapid advances have been made in medical devices and apparatus for controlling chronic intractable pain. One such apparatus involves the implantation of an electrode array within the body to electrically stimulate the area of the spinal cord that conducts electrochemical signals to and from the pain site. The stimulation creates the sensation known as paresthesia, which can be characterized as an alternative sensation that replaces the pain signals sensed by the patient. One theory of the mechanism of action of electrical stimulation of the spinal cord for pain relief is the "gate control theory". This theory suggests that by simulating cells wherein the cell activity counters the conduction of the pain signal along the path to the brain, the pain signal can be blocked from passage.

Spinal cord stimulator and other implantable tissue stimulator systems come in two general types: "RF" controlled and fully implanted. The type commonly referred to as an "RF" system includes an external transmitter inductively coupled via an electromagnetic link to an implanted receiver that is connected to a lead with one or more electrodes for stimulating the tissue. The power source, e.g., a battery, for powering the implanted receiver-stimulator as well as the control circuitry to command the implant is maintained in the external unit, a hand-held sized device that is typically worn on the patient's belt or carried in a pocket. The data/power signals are transcutaneously coupled from a cable-connected transmission coil placed over the implanted receiver-stimulator device. The implanted receiver-stimulator device receives the signal and generates the stimulation. The external device usually has some patient control over selected stimulating parameters, and can be programmed from a physician programming system. An example of an RF system is described, e.g., in U.S. Pat. No. 4,793,353, incorporated herein by reference.

The fully implanted type of stimulating system contains the programmable stimulation information in memory, as well as a power supply, e.g., a battery, all within the implanted pulse generator, or "implant", so that once programmed and turned on, the implant can operate independently of external hardware. The implant is turned on and off and programmed to generate the desired stimulation pulses from an external programming device using transcutaneous electromagnetic, or RF links. Such stimulation parameters include, e.g., the pulse width, pulse amplitude, repetition rate, and burst rates. An example of such a commercially-available implantable device is the Medtronic Itrel II, Model 7424. Such device is substantially described in U.S. Pat. No. 4,520,825, also incorporated herein by reference.

The '825 patent describes a circuit implementation of a cyclic gradual turn on, or ramping of the output amplitude, of a programmable tissue stimulator. The implementation contains separate memory cells for programming the output amplitude and number of pulses at each increasing output level or "step". In devices of the type described in the referenced '825 patent, it is desirable to provide some means of control over the amplitude (intensity), the frequency, and the width of the stimulating pulses. Such control affords the patient using the device the ability to adjust the device for maximum effectiveness. For example, if the pulse amplitude is set too low, there may be insufficient pain relief for the user; yet, if the pulse amplitude is set too high, there may be an unpleasant or uncomfortable stinging or tingling sensation felt by the user. Moreover, the optimum stimulation parameters may change over time. That is, numerous and varied factors may influence the optimum stimulation parameters, such as the length of time the stimulation has been ON, user (patient) postural changes, user activity, medicines or drugs taken by the user, or the like.

In more complex stimulation systems, one or more leads can be attached to the pulse generator, with each lead usually having multiple electrode contacts, Each electrode contact can be programmed to assume a positive (anode), negative (cathode), or OFF polarity to create a particular stimulation field when current is applied. Thus, different combinations of programmed anode and cathode electrode contacts can be used to deliver a variety of current waveforms to stimulate the tissue surrounding the electrode contacts.

Within such complex systems, once one or more electrode arrays are implanted in the spinal cord, the ability to create paresthesia over the painful site is firstly dependent upon the ability to accurately locate the stimulation site. This may more readily be accomplished by programming the selection of electrode contacts within the array(s) than by physically maneuvering the lead (and hence physically relocating the electrode contacts). Thus, the electrode arrays may be implanted in the vicinity of the target site, and then the individual electrode contacts within the array(s) are selected to identify an electrode contact combination that best addresses the painful site. In other words, electrode programming may be used to pinpoint the stimulation area correlating to the pain. Such electrode programming ability is particularly advantageous after implant should the lead contacts gradually or unexpectedly move, thereby relocating the paresthesia away from the pain site. With electrode programmability, the stimulation area can often be moved back to the effective site without having to re-operate on the patient in order to reposition the lead and its electrode array.

Electrode programming has provided different clinical results using different combinations of electrode contacts and stimulation parameters, such as pulse width, amplitude and frequency. Hence, an effective spinal cord stimulation system should provide flexible programming to allow customization of the stimulation profile for the patient, and thereby allow for easy changes to such stimulation profile over time, as needed.

The physician generally programs the implant, external controller, and/or external patient programmer through a computerized programming station or programming system. This programming system can be a self-contained hardware/software system, or can be defined predominately by software running on a standard personal computer (PC). The PC or custom hardware can have a transmitting coil attachment to allow for the programming of implants, or other attachments to program external units. Patients are generally provided hand-held programmers that are more limited in scope than are the physician-programming systems, with such hand-held programmers still providing the patient with some control over selected parameters.

Programming of the pulse generators, or implants, can be divided into two main programming categories: (1) programming of stimulation pulse variables, and (2) programming electrode configurations. Programmable stimulation pulse variables, as previously indicated, typically include pulse amplitude, pulse duration, pulse repetition rate, burst rate, and the like. Programmable electrode configuration includes the selection of electrodes for simulation from the available electrode contacts within the array as well as electrode polarity (+/−) assignments. Factors to consider when programming an electrode configuration include the number of electrode contacts to be selected, the polarity assigned to each selected electrode contact, and the location of each selected electrode contact within the array relative to the spinal cord, and the distance between selected electrodes (anodes and cathodes), all of which factors combine to define a stimulation field. The clinician's electrode selection results in a simulating "group" containing at least one anode and at least one cathode that can be used to pass stimulating currents defined by the programmed pulse variables. For an electrode array having eight electrode contacts, this can result in an unreasonable large number of possible combinations, or stimulation groups, to chose from.

Moreover, within each stimulation group, there are a large number of pulse stimulation parameters that may be selected. Thus, through the programmer, the clinician must select each electrode, including polarity, for stimulation to create each combination of electrode contacts for patient testing. Then, for each combination, the clinician adjusts the stimulation parameters for patient feedback until the optimal pain relief is found for the patient. Disadvantageously, it is difficult to test many stimulation variables with hundreds or even thousands of possible electrode and stimulus parameter combinations. To test all such combinations, which is typically necessary in order to find the optimum stimulation settings, is a very lengthy and tedious process. Because an all-combination test is lengthy and tedious, some clinicians may not bother to test many different electrode combinations, including many that may be considered far more optimal than what is ultimately programmed for the patient. It is thus evident that there is a need in the art for a more manageable programming technique for testing and handling a large number of possible electrode and pulse parameter combinations.

One method that has recently been developed for simplifying the programming process is described in U.S. Pat. No. 5,370,672, incorporated herein by reference. The '672 patent describes a programming system where the patient interacts with the clinician's programmer. More specifically, the '672 patent teaches a system wherein the patient identifies the pain site by "drawing" the pain site on a touch screen that displays an illustration of the human body. After entering the patient's stimulation thresholds and associated tolerances into the system, the computer generates a recommended electrode configuration for that patient using algorithms based on spinal cord stimulation research. The patient responds to the resulting stimulation by drawing the amount of paresthesia coverage over the body illustration. If the drawing paresthesia site does not fully match the pain site, the system adjusts the recommendation, and the patient responds again to the new sense of paresthesia. This process is repeated until the best-tested settings are reached.

Advantageously, the process described in the '672 patent effectively eliminates the manual selection of electrode combinations, and reduces the selection process to a reasonable testing of electrode/parameter combinations based on an extensive pre-organized set of rules for programming optimization and patient input. Moreover, the physician/clinician is not directly controlling the programming session; rather, the patient provides the system with the feedback without the need for the physician or clinician to interpret the patient's sensations or empirically estimate changes required in stimulation parameters.

Disadvantageously, using the method described in the '672 patent, the patient must still test and respond to each of the chosen combinations and must depend upon the system recommendations, which system recommendations might exclude a possible optimal setting for that patient. Further, the patient must be able to accurately translate subtle sensations and differences to a drawing on a screen, and then wait for device programming before having to react and redraw the paresthesia from the new settings. Such process can still be time consuming. Furthermore, subtle sensation differences felt by the patient between combinations cannot necessarily be translated in a drawing of paresthesia that only address "coverage area." In summary, by reducing the combinations to a computer-generated recommendation, many electrode combinations might be omitted that could provide a more effective paresthesia. Hence, the process of computer-recommended combinations, although superior to manual arbitrary selection, can still be viewed as an undesirable "discrete" method of patient feedback evaluation: i.e., electrodes are programmed and patient feedback is entered for each combination, one iteration at a time.

In view of the above, it is evident that profound improvements are still needed in the way multiple implanted electrode combinations are programmed. In particular, it is seen that improvements in programming techniques and methods are needed that do not compromise the patient's ability to feel the subtle effects of many different combinations, and that provide a more immediately responsive programming-to-feedback loop.

SUMMARY OF THE INVENTION

The present invention advantageously addresses the needs above, as well as other needs, by providing improved programming methods for electrode arrays having a multiplicity of electrodes. The present invention advantageously simplifies the programming of multiple electrode contact configurations by using a directional input device in conjunction with a programmer/controller to automatically combine and reconfigure electrodes with alternating current paths as determined by the directional input device. The directional input device used with the invention may take many forms, e.g., a joystick, a button pad, a group of keyboard arrow keys, a touch screen, a mouse, or equivalent directional input mechanisms. Advantageously, the use of a directional input device to automatically adjust electrode configurations in order to "steer" the stimulation current allows the patient to immediately feel the effect of electrode configuration changes. Then, without having to translate the subtle differences of sensation to a drawing for discrete computer-generated recommendations, or manually and arbitrarily selecting different combinations, the patient responds continuously to the sensation by steering directional or equivalent controls. Hence, the patient more directly controls the programming without being cognizant of actual electrode combinations and variables. The patient is also more immediately responsive, since there is no need to translate the perceived sensations to specific locations on a displayed drawing. This process is thus analogous to continuous feedback as opposed to discrete feedback and system manipulation.

While the directional programming device provided by the invention is primarily intended to program implanted stimulator devices having at least two electrode contacts, it should also be noted that it can also be used to program the electrodes used with external stimulators.

The invention described herein thus relates, inter alia, to a method of programming utilizing directional input signals to "steer" and define current fields through responsive automated electrode configuring. Hence, in accordance with one aspect of the invention, programming equipment is utilized including a computer and/or custom transmitter, coil and programming software to achieve the desired current field steering effect. Additional control mechanisms (software and/or hardware) are used to respond to directional control signals generated, e.g., with a joystick or other directional means, so as to configure and combine the electrodes as directed by the joystick or other directional-setting device so as to redistribute the current/voltage field in a way that prevents the paresthesia felt by the patient from either falling below a perceptual threshold or rising above a comfort threshold. As needed, one or more other input devices can be used to control different aspects of the electrode configuration.

In accordance with another aspect of the invention, a representation of the changing current fields resulting from movement of the directional device is visually provided on a display screen associated with the programming equipment, thereby providing visual feedback to the user as to the electrode configurations and/or resulting stimulation fields that are achieved through manipulation of the directional input mechanism.

In use, a spinal cord stimulator is implanted with one or more leads attached to the spinal cord. The implanted spinal cord stimulator is coupled through an RF or other suitable link to the external spinal cord stimulation system, which system is used to program and/or control the implanted stimulator. The style and number of leads are entered into the system software. The clinician then maneuvers the joystick, or other directional instructor, to redirect current to different groups of implanted electrodes. The software then automatically reconfigures electrodes according to directional responsive rules in the software and/or electronics. Automatic configuring of the electrodes to steer current includes, e.g., the number of electrodes, the selection of electrodes, the polarity designation of individual electrodes, and the distribution of stimulation intensities among the selected electrodes.

The advantage achieved with the programming system provided by the invention is that the clinician never has to actually select and test a multitude of electrode combinations with the patient, which otherwise takes time for each configuration. Instead, the patient immediately responds to maneuvers conducted by himself/herself or the clinician, which causes the user to move toward or away from certain directions. The directional programming feature may also be made available directly to the patient through a small portable programming device. Advantageously, all reconfiguring of the electrodes is done automatically as a function of the directional signals generated by the joystick or other directional device(s), and is done in a way that prevents the paresthesia felt by the patient from falling below the perceptual threshold or rising above the comfort threshold.

One embodiment of the invention may be viewed as a programming system for use with a neural stimulation system. Such neural stimulation system includes: (1) a multiplicity of implantable electrodes adapted to contact body tissue to be stimulated; (2) an implantable pulse generator connected to each of the multiplicity of electrodes, the implantable pulse generator having electrical circuitry responsive to programming signals that selectively activates a plurality of the implantable electrodes, wherein at least one electrode in the plurality of activated implantable electrodes functions as a cathode, and wherein at least one electrode in the plurality of activated implantable electrodes functions as an anode, whereby stimulus current flows from the at least one activated anodic electrode to the at least one activated cathodic electrode; (3) a programming device coupled with the implantable pulse generator, the programming device having control circuitry that generates programming signals adapted to control the implantable pulse generator; (4) an input device coupled with the programming device, wherein the input device generates directional signals as a function of user control; and (5) control logic within the programming device that continuously activates selected ones of the multiplicity of implantable electrodes in response to the directional signals received from the user controlled input device, whereby stimulus current is selectively redistributed among cathodic and anodic electrodes as directed by the user controlled input device. The electrical circuitry within the implantable pulse generator may activate the selected electrodes by forcing a prescribed current to flow into (a current sink) a cathodic electrode, by forcing a prescribed current to flow from (a current source) an anodic electrode, by causing a prescribed positive voltage to be applied to an anodic electrode, by causing a prescribed negative voltage to be applied to a cathodic electrode, or by combinations of the above.

It is thus a feature of the present invention to provide a system and a method for programming that allows a clinician or patient to quickly determine a desired electrode stimulation pattern, including which electrodes of a multiplicity of electrodes in an electrode array should receive a stimulation current, the polarity, distance between anodes and cathodes, and distribution of stimulation intensity or amplitude.

It is another feature of the invention to provide an electrode selection system that allows the user (the person operating the programmer) to readily select and visualize a particular group of electrodes of an electrode array for receipt of a stimulation pulse current, and when selected to allow different combinations of pulse amplitude, pulse width, pulse repetition rate, or other pulse-defining parameters to be applied to the selected group.

It is yet an additional feature of the invention to allow an implantable tissue stimulator, having an array of stimulation electrodes attached thereto, to be readily and quickly programmed so that only those electrodes which prove most effective for a desired purpose, e.g., pain relief, are selected and configured to receive a pulsed current having an amplitude, width, repetition frequency, or burst parameters that best meets the needs of a particular patient.

It is still another feature of the invention to provide a system and a method of steering or programming the perceived paresthesia so that any needed redistribution of the stimulus current occurs in small step sizes, thereby making neural recruitment more effective. In accordance with this feature of the invention, the small step size in current or voltage amplitude settings that is used amongst the electrode contacts is selected to effectively correspond to the spatial resolution to which neural elements can be activated. That is, this spatial resolution is meaningful to the extent that the micro-anatomy of the neural structures being activated gives rise to different clinical effects. Advantageously, by using such a system that automatically redistributes current or voltage amplitudes amongst electrodes in suitable small step sizes, desired neural activation patterns may be found more easily.

It is another feature of the invention to provide a system for redistributing current and/or voltage amplitudes amongst selected electrodes using a user interface that is simple and intuitive.

It is an object of the invention to eliminate the need for either a clinician to manually select electrode combinations, or even for a computer to select electrode combinations that must be discretely tested for patient feedback. That is, based on the feedback as to the amount of coverage, an educated guess for another combination must be made (by clinician or computer) and the patient must then discretely respond to that combination before another combination is set up and turned on. Such discrete testing with patient feedback is very tedious and time consuming. Advantageously, by practicing the present invention, discrete selection and patient feedback of location and amount of paresthesia coverage (either to the clinician or to a computer) is avoided.

BRIEF DESCRIPTION OF THE DRAWINGS

The above and other aspects, features and advantages of the present invention will be more apparent from the following more particular description thereof, presented in conjunction with the following drawings wherein:

FIG. 7 shows a table-based current shifting algorithm for horizontal shifting;

FIGS. 12A through 12J (note, there is no FIG. 12I) illustrate various screens that may be used by the software wizard as it carries out the steps depicted in FIG. 11;

Like reference numerals are used to refer to like elements or components throughout the several drawing figures.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it is to be noted that a preferred implementation for a directional programming device in accordance with the present invention is through the use of a joystick-type device or equivalent. Hence, in the description that follows, a joystick device is described. It is to be understood, however, that other directional-programming devices may also be used in lieu of a joystick, e.g., a roller ball tracking device, horizontal and vertical rocker-type arm switches, selected keys (e.g., directional-arrow keys) on a computer keyboard, touch-sensitive surfaces on which a thumb or finger may be placed, recognized voice commands (e.g., “up”, “down”, “diagonal”, etc.), recognized movement of body parts (e.g., detecting eye blinks, finger taping, muscle contraction, etc.), and the like. Any type of hardware or software that allows directional signals to be generated through motion or movement of a body part, or through the movement of keys, levers, or the like, or through recognition of voice or visual commands, may be used as the directional programming device used with the invention.

Thus, it is seen that any input device capable of driving software, electrical hardware, as well as mechanical systems that configure stimulation electrodes, may be used with the present invention as a directional programming device. Additional input devices include voice activated and mechanical dials that can cause the switching of electrodes and output distributions. The shifting of electrodes occurs in response to input signals derived from the user controlled input device.

While the embodiment described below relates to a spinal cord stimulator for the treatment of pain, it is to be understood that the principles of the invention also apply to other types of tissue stimulator systems. Likewise, although the preferred embodiment includes software for use in conjunction with a PC, it is to be understood that the invention can also be implemented through custom programming devices for either the clinician or the patient, with or without visual displays.

Figure 1A:
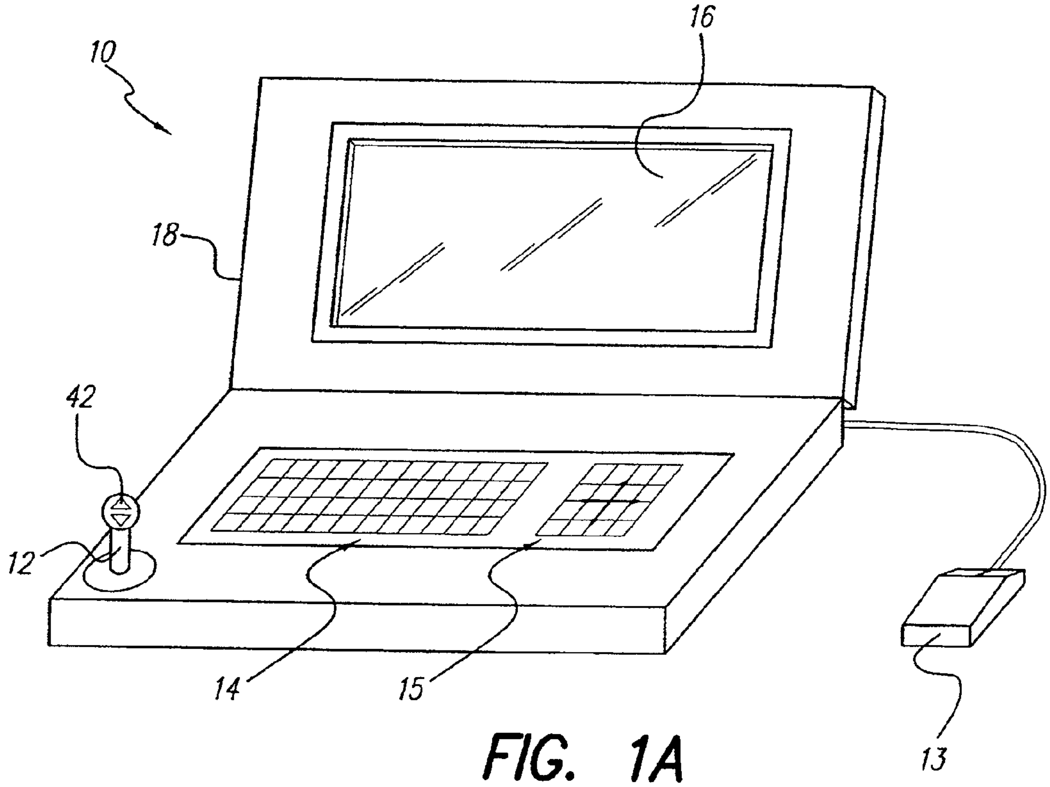
FIG. 1A is a perspective view of one embodiment of a directional programmer device with a visual display in accordance with the present invention.

Turning first to FIG. 1A, there is shown a representative view of a directional programmer system 10 implemented in accordance with one embodiment of the invention. Such system 10 comprises a joystick 12 (or other type of directional programming device), a keyboard 14, and a programming display screen 16, housed in a case 18. As seen in FIG. 1A, the overall appearance of the system 10 is that of a laptop personal computer (PC) and, in fact, the system 10 may be implemented using a PC that has been appropriately configured to include a directional-programming device and programmed to perform the functions described herein. As indicated previously, it is to be understood that in addition to, or in lieu of, the joystick 12, other directional programming devices may be used, such as a mouse 13, or directional keys 15 included as part of the keys associated with the keyboard 14.

Figure 1B:
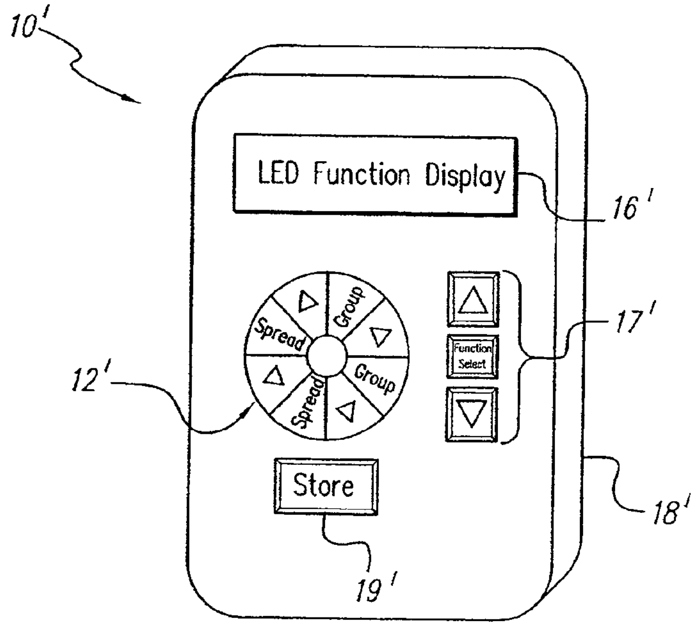
FIG. 1B is a perspective view of another embodiment of a directional programmer device in accordance with the present invention.

FIG. 1B depicts a custom directional programmer system 10' that may also be used with the invention. The programmer system 10' is built within a case 18' designed to fit within the hand of the user, and includes an array 12' of directional keys which allow directional signals to be generated, equivalent to those generated by a joystick. The hand-held unit 10' further includes a functional display 16', typically realized using light emitting diodes (LEDs), as is known in the art. Various programmable features or functions associated with the programmer system 10' may be selected using the keys 17'. Once selected, a "store" button 19' is provided to allow a desired electrode configuration, including other selected parameters, or a desired function, to be selected and saved in memory so that it can be recalled as desired to define the electrode configuration to be used at a later date.

Figure 3:
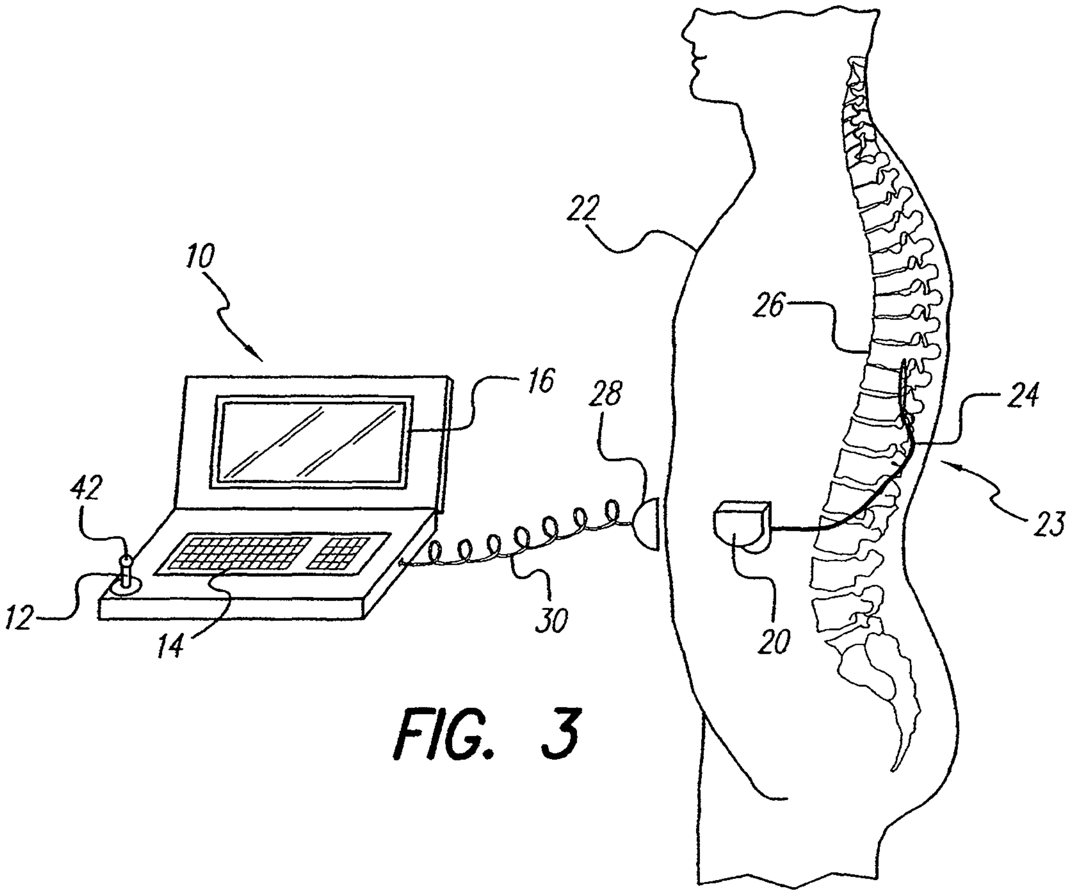
FIG. 3 is a schematic view of a patient with an implanted stimulator, coupled to a directional programmer system.

The joystick programmer system 10 of FIG. 1A, or the alternate hand-held programmer 10' of FIG. 1B, is intended to be used with an implanted tissue stimulator, e.g., an implantable spinal cord tissue stimulator 20 (see FIG. 3). A spinal cord tissue stimulator, as shown in FIG. 3, is typically implanted in the abdomen of a patient 22. An electrode array 23, electrically connected to the simulator 20, has individual electrode contacts, or electrodes 24, arranged in a desired pattern and positioned near the spinal column 26, The spinal stimulator 20, when appropriately programmed, is used by the patient for the control of pain. A more thorough description of a spinal cord stimulator may be found in the previously referenced '829 provisional patent application, which application has been incorporated herein by reference.

Advantageously, the directional programmer systems 10 or 10' greatly simplify the programming of multiple implanted electrode contact configurations. As previously indicated, programming systems currently require the physician or clinician to specifically select and manually input the electrode combinations that are to used for stimulation—a time-consuming and frustrating process. In contrast, the present invention allows the physician or clinician to readily determine a desired combination of electrodes, i.e., a selected "group" of electrodes, using the joystick 12 (or other directional programming device) that affects which electrodes are selected, the polarity of individual electrodes, and the stimulation intensity distribution, all of which parameters can contribute to "steer" and/or "focus" the stimulation current. In other words, through use of the present invention, the operator can adjust the stimulation field location, concentration and spread by maneuvering the joystick 12 that automatically configures electrodes for stimulation. Advantageously, as the stimulating group of electrodes is being configured and positioned using the directional signals generated by the joystick 12, the programmed stimulation is automatically directed to the electrodes for immediate and continuous patient response. A preferred technique for generating the directional signals that are automatically directed to electrodes in accordance with the invention, particularly in relation to moving the directional signals from one stimulation site to another in small steps, is described hereinafter.

Figure 2:
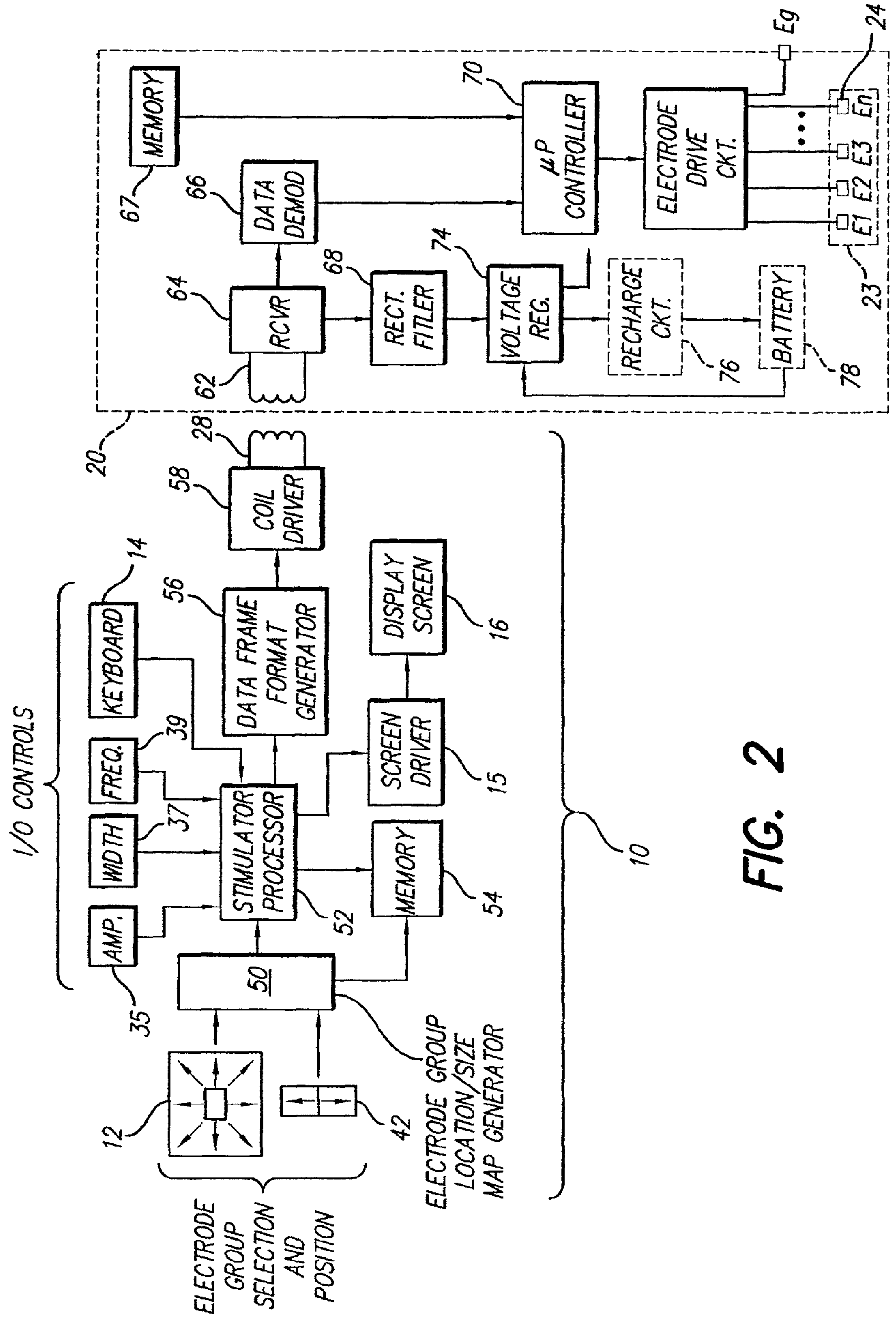
FIG. 2 is a functional block diagram of a directional programmer system in accordance with the present invention.

FIG. 2 shows a functional block diagram of a directional programming system 10 made in accordance with the present invention, and further includes a functional block diagram of the implantable tissue stimulator 20 that is programmed and controlled using such system. It is to be emphasized that the block diagram shown in FIG. 2 is a functional block diagram, i.e., a diagram that illustrates the functions performed by the programming system 10 and stimulator 20. Those of skill in the art, given the descriptions of the invention presented herein, can readily configure various hardware and/or software components that may be used to carry out the functions of the invention.

The implantable tissue stimulator 20 will be described first. It should be noted that the implantable tissue stimulator 20, per se, is not the subject of the present invention. Rather, the invention relates to a device or system for programming and/or controlling the stimulator 20 so that a desired pattern of tissue stimulation currents are applied to a selected group of electrodes that form part of the tissue stimulator 20. Nonetheless, in order to better understand and appreciate how the programming system 10 of the invention interacts with the stimulator 20, it will also be helpful to have at least a functional understanding of how the stimulator 20 operates.

Thus, as seen in FIG. 2, the implantable tissue stimulator 20 includes a coil 62 for receiving RF or other control signals and power from an external source, e.g., from the programmer 10. The signals thus received are passed through a receiver circuit 64. A rectifier/filter circuit 68 extracts power from the received signals and presents such extracted power to a voltage regulator circuit 74, which regulator circuit 74 generates the operating voltages needed within the implantable stimulator device 20. A preferred implantable tissue stimulator 20 includes a rechargeable or replenishable energy source 78, e.g., a rechargeable battery and/or large capacitor. If so, a suitable recharging circuit 76 derives power from the voltage regulator 74 and/or rectifier/filter circuit 68 for recharging or replenishing such power source 78. The power source 78, in turn, provides its stored energy to the voltage regulator circuit 74.

The signals received by the implant receiver circuit 64 are also directed to a data demodulator 66, which demodulator demodulates the control information (data) that is included in the signals received from the programmer 10. Typically, such control data are arranged in a sequence of frames, with certain bits of data in each frame signifying different commands or other information needed by the tissue stimulator 20 in order for it to carry out its intended function. Such control data, once recovered by the data demodulator 66, is presented to a controller 70. e.g., a microprocessor (μP) controller. The μP controller 70, upon receipt of the data, acts upon it in order to carry out whatever commands have been received.

The μP controller 70 may be programmed to operate in numerous modes. Typically, an operating program, stored in a suitable memory device 67 included within the implantable stimulator 20, directs or controls the μP controller 70 to carry out a sequence of operations. In some implementations, the operating program itself may be received and programmed into the memory 67 through receipt of the data commands received from the programmer 10. In other implementations, a basic operating program is permanently stored in the memory 67, e.g, in a read only memory (ROM) portion of memory 67, and various parameters associated with carrying out such basic operating program may be modified and stored in a random access memory (RAM) portion of the memory 67 through the data commands received from the programmer 10.

Regardless of how the operating program is received and stored within the tissue stimulator 20, it generally causes an electrical stimulation current, e.g., a biphasic stimulation current, to be applied to one or more selected pairs of a multiplicity of electrodes, E1, E2, E3, . . . . En, associated with the stimulator. That is, as controlled by the control signals received from the programmer 10, which signals may be acted on immediately, or stored in memory 67 for subsequent action, a given electrode of the multiplicity of electrodes E1, E2, E3, . . . En included within an array 23 of electrodes, is either turned ON or turned OFF, and if turned ON, it receives a biphasic or other current pulse having a selected amplitude, pulse width, and repetition frequency. In this manner, then, as controlled by the control signals received from the programmer 10, the tissue stimulator 20 thus applies a selected stimulation current to selected pairs of the electrodes included within the electrode array 23.

In some programming modes, an indifferent or return electrode, Eg, which may in fact form part of the case or housing of the implantable stimulator 20, may be paired with individual ones of the electrodes E1, E2, E3, . . . En so as to provide “monopolar” stimulation. When two of the electrodes E1, E2, E3, . . . En are paired together, such stimulation is generally referred to as “bipolar” stimulation. Stimulation currents must always be applied through two or more electrodes, with at least one electrode functioning as an anode and with at least one electrode functioning as a cathode, so that the stimulation current may flow into the tissue to be stimulated through one path and return therefrom through another path.

Still with reference to FIG. 2, the functions performed by the directional programmer system 10 will next be described. As seen in FIG. 2, a key element of such system 10 is the directional control device 12, which may comprise, e.g., a joystick device. Coupled with the directional control device 12 is a plurality of up/down bottons or selector buttons 42. The control device 12 and selector buttons 42 provide signals to an electrode group location/size map generator circuit 50 that defines a group 45 of electrodes 24 (see FIG. 4) within the array 23 of electrodes, which, depending upon the selected polarity of individual electrodes 24 within the group 45 of electrodes, further defines an electric field 33 between the selected electrodes that effectively defines a stimulation area 36 that receives the stimulation current. The definition of the group of electrodes 45 is provided to a stimulator processor circuit 52 and/or to a memory circuit 54.

Also provided to the stimulator processor circuit 52 are data that define a desired pulse amplitude, pulse width, and pulse repetition rate, and any other stimulation parameters (e.g., burst repetition rate, etc.) that characterize the stimulation pulses that are to be applied to the selected group of electrodes. Such characterization data may be preprogrammed into the processor 52, or it may be set through use of manual selection input/output (I/O) devices 35, 37 and 39, which devices may be implemented in hardware (e.g., slide switches) or software (e.g., simulated slide switches that appear on the display screen 16 of the programmer 10). Further, amplitude programming (also referred to as “magnitude programming”), as explained in more detail below, and as further described in the ’167 provisional patent application previously referenced and incorporated herein by reference, is preferably implemented to facilitate the programming of the stimulator system. Other I/O devices may also be used, e.g., the keyboard 14, as required, in order to enter needed characterization data.

The stimulator processor 52 takes the pulse characterization data, as well as the electrode group data, and processes such data so that the appropriate commands can be sent to the implantable receiver 20. A suitable data frame format generator circuit 56 may be used to form the data into suitable data frames that will be recognized and acted upon by the implant stimulator 20, as is known in the art. In practice, the function of the data frame format generator circuit 56 may be carried out as part of the processing functions performed by the stimulator processor 52. Once properly framed, such data commands are sent to a coil driver circuit 58, which drives the external coil 28, causing such signals to be inductively or otherwise coupled into the implant coil 62 and implant receiver circuit 64 of the implantable stimulator 20. The implantable stimulator 20 then acts on the data received so as to provide the programmed stimulation currents to the group of electrodes selected by the directional device 12 and selectors 42, using the polarity defined by the received data.

Also included as part of the programming system 10 is a display screen 16, and associated screen driver circuit 15. The display screen provides a display as controlled by the stimulator processor 52 of data, or other information, in conventional manner. For purposes of the present invention, as explained in more detail below in connection with FIGS. 4 and 5A, the display screen 16 displays a simulated picture of the implanted electrodes, as well as the selected group of electrodes. The moving, expanding, or contracting stimulation field 33 is then displayed in response to the directional controller 12 and selection controls 42.

It is noted that the implantable stimulator 20 may also include back telemetry capability which allows it to send data to the external programmer 20. Such back telemetry data may include status signals, e.g., voltage levels within the stimulator 20, and/or sensed data, e.g., sensed through one or more of the electrodes 24. In such instances, the programmer 10 includes appropriate circuitry for sensing and acting upon such received back telemetry data. For simplicity, such back telemetry features are not included in the functional block diagram of FIG. 2, but it is to be understood that such features may be used with the invention.

The following issued United States patents, each of which is incorporated herein by reference, provide additional detail associated with implantable tissue stimulators, programming such stimulators, and the use of biphasic stimulation pulses in a bipolar, monopolar or other stimulation mode: U.S. Pat. Nos. 5,776,172; 5,649,970; 5,626,629; and 5,601,617.

Turning next to FIG. 3, a typical implanted programmable spinal cord stimulator 20 is schematically illustrated. Such stimulator is typically implanted in the abdomen of a patient 22 for control of pain by electrical stimulation of the spinal cord. The stimulator 20 is connected to an array 23 of electrodes 24 implanted near the spinal column 26 of the patient 22. The preferred placement of the electrodes 24 is adjacent, i.e., resting upon, the spinal cord area to be stimulated. The stimulator 20 includes a programmable memory located inside of it which is used to direct electrical current to the lead electrodes 24. Modifying the parameters in the programmable memory of the stimulator 20 after implantation is performed by a physician or clinician using the directional programmer system 10. For example, control signals, e.g., modulated RF signals, are transmitted to a receiving coil inside the stimulator 20 by a transmission coil 28 connected to the programmer 10 via a cable 30.

In accordance with the teachings of the present invention, the directional programmer system 10 is used by the physician to modify operating parameters of the implanted electrodes 24 near the spinal cord 26. As it does so, the modification of operating parameters in carried out in an optimum manner such that changes in stimulus current occur gradually, in small steps, as the stimulus field moves from one group of electrodes to another. That is, in a preferred implementation, the inclusion or exclusion of a given electrode within a selected group of electrodes is gradually phased in or out, as directed by the directional controls received from the directional programmer system 10. The programmer system 10, as indicated above in connection with the description of FIG. 2, may selectively turn the stimulator 200N or OFF, or adjust other parameters such as pulse rate, pulse width and/or pulse amplitude, as desired.

Figure 4:
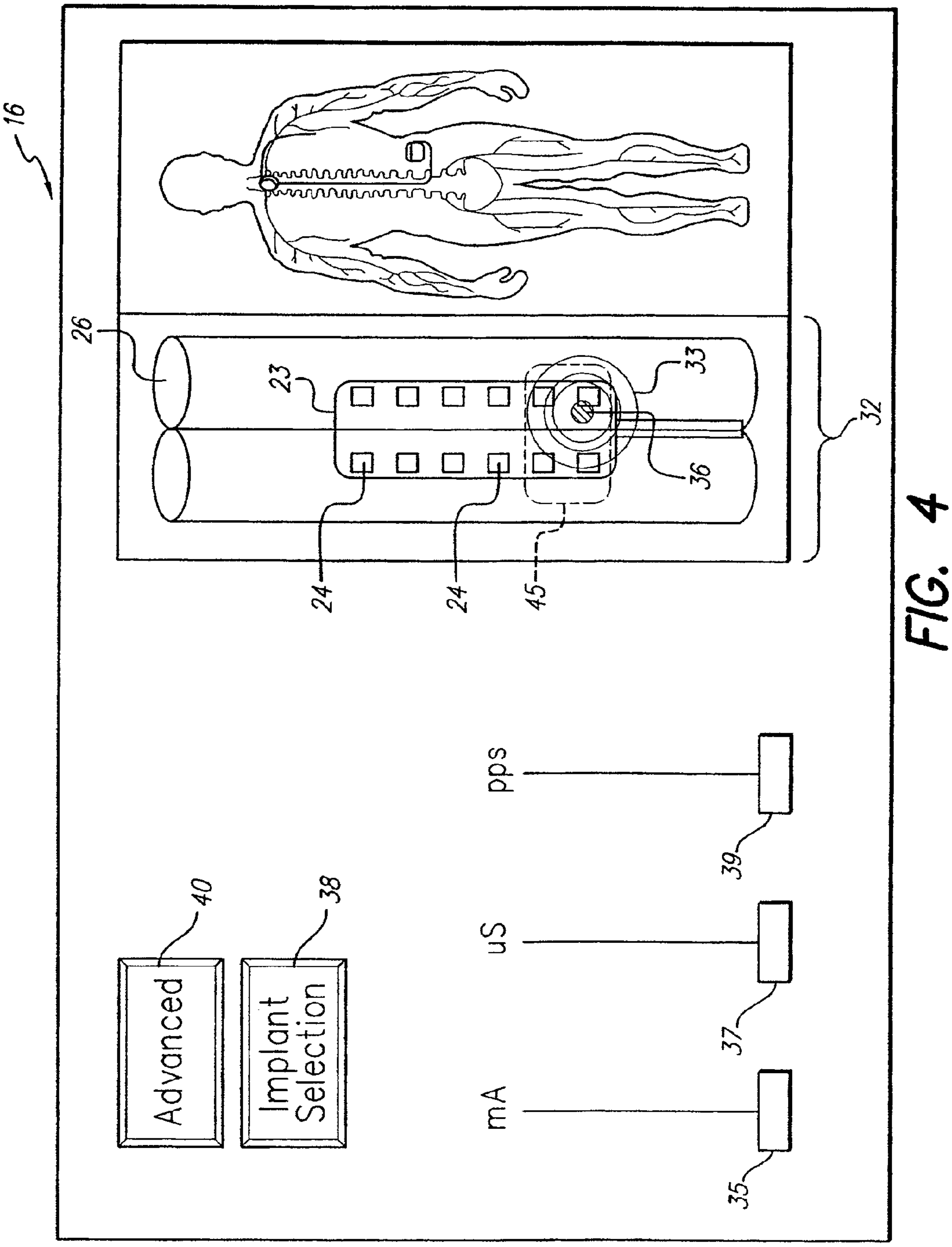
FIG. 4 is a view of the directional programmer display screen of FIG. 1A.

FIG. 4 illustrates a representative programming display screen 16 used with the directional programmer system 10. The programming screen 16 visually provides all of the information required to program the stimulator 20 and electrodes 24. Various types of programming information may be provided depending on the complexity desired from the system.

For the programmer system 10 to carry out its intended function, it must know the style, number, and location of the electrodes 24 that have been implanted near the spinal cord 26, along with information characterizing the implanted spinal cord stimulator 20 (i.e., the model number which determines performance capabilities of the implanted stimulator). Information regarding the type of electrode array 23, including the number and relative position of the individual electrodes 24 included within the array 23, as well as information characterizing the stimulator 20, may be entered and stored in the system 10 using the keyboard 14, or other suitable data-entry input/output (I/O) device. Alternatively, the electrode array and electrode information may be preprogrammed into the system 10. The electrode array position data may be determined using any suitable procedure, such as X-ray, xerography, fluoroscopy, or other imaging techniques, which position data is then entered into the programming system.

The programming screen shown in FIG. 4 includes an "Implant Selection" button 38. By clicking on the Implant Selection button 38 (or pressing on the button when a touch-sensitive screen is employed) displayed on the display screen 16, a drop-down list appears containing data that characterizes the available stimulators 20 and electrode array designs. Using the joystick 12 or keyboard 14 or other I/O device, the information for the implanted unit may be chosen from the list and input into the system. If the information for a particular unit is not on the list, the information can be entered. Pressing the "Advanced" button 40 provides access, through an appropriate menu selection, to advanced programming features such as manual electrode selection, burst programming, stimulation ramping, and other features commonly used in the art. The information is provided to the programmable memory 67 (FIG. 2) of the stimulator 20 in order to control the delivery of electrical pulses to the desired electrodes 24.

Once information characterizing the electrodes 24 and stimulator 20 are input into the system, a simulated display appears on one portion (e.g., the right portion as shown in FIG. 4) of the programming display screen 16 that illustrates the placement and relative position of each of the electrodes 24 included within the array 23 of electrodes relative to the patient's spinal column 26. A simulated display 32 of the electrode array pattern 23 thus appears on the display screen 16 just as though the programmer could view inside the patient to see the electrode placement on or near the spinal column. For the representative electrode array 23 shown in FIG. 4, two columns of electrodes 24 are used, each having six electrodes. Thus, the particular electrode array 23 shown in FIG. 4 has a total of twelve (12) electrodes. Each electrode in each column is spaced apart from adjacent electrodes along the same column. It is to be emphasized that the type of array shown in FIG. 4 is exemplary of only one type of many different types of arrays that may be used. Often, two or more leads are implanted, each having its own array. In such instance, the information (two or more leads with respective arrays) is entered into the system and accounted for in the programming and visual displays. What is relevant to the programmer is which lead(s) is (are) being used (to determine the electrode array layout, how the lead(s) is (are) oriented with respect to one another and the spinal cord, and which pulse generator within the implant is driving the stimulation electrode contacts.

The basic functions addressed by directional programming in accordance with the present invention include moving, concentrating, and focusing the stimulation field. While these functions could be separately controlled by several input devices, a preferred embodiment of the present invention advantageously minimizes hardware and software buttons by combining all these functions into one device, e.g., a single joystick device 12, thereby providing simplification in both design and use. The manner in which the preferred joystick device addresses each of these functions is depicted in FIG. 5A.

Any number of electrodes 24, out of the total available, may be formed into an electrode group 45 which can be displayed as a stimulation field 36. Through use of an additional data input device, e.g., selector button 42, the number of electrodes within the electrode group 45 can be increased or decreased. Such action (increasing or decreasing the number of electrodes in the group) redistributes, or concentrates, the stimulation current over a greater of smaller area.

The selector 42, for the embodiment shown in FIG. 3, comprises a pair of arrow buttons (up/down) that are located on top of the joystick 12. Of course, such selector 42 could also be separate, i.e., accessed from keyboard buttons. In a preferred implementation, the number of electrodes in a stimulation group 45, from 2 to n, where n is an integer greater than or equal to three, is initially determined by increase/decrease input from the selector, rather than by manually selecting electrodes.

Once the starting number of electrodes (concentration of stimulation) is determined, it is then focused and/or moved by the directional input of joystick 12. Selection software algorithms, stored in memory 54, work in conjunction with the position defined by the joystick 12, and/or other directional instructional means, to configure and combine the electrodes 24 into the electrode group creating the stimulation field 36. As the physician or patient maneuvers the joystick 12, the resulting stimulation field 36 and/or the selected electrodes can be visualized on display 32 (e.g., by a different color, by shading, by a dashed line encircling the selected electrodes, or the like.) The preferred manner in which the current stimuli is applied through the electrodes in the stimulation group 45, and more particularly the manner in which the current stimuli increases or decreases as the stimulation field is increased or decreased, is described more fully below.

Figure 5B:
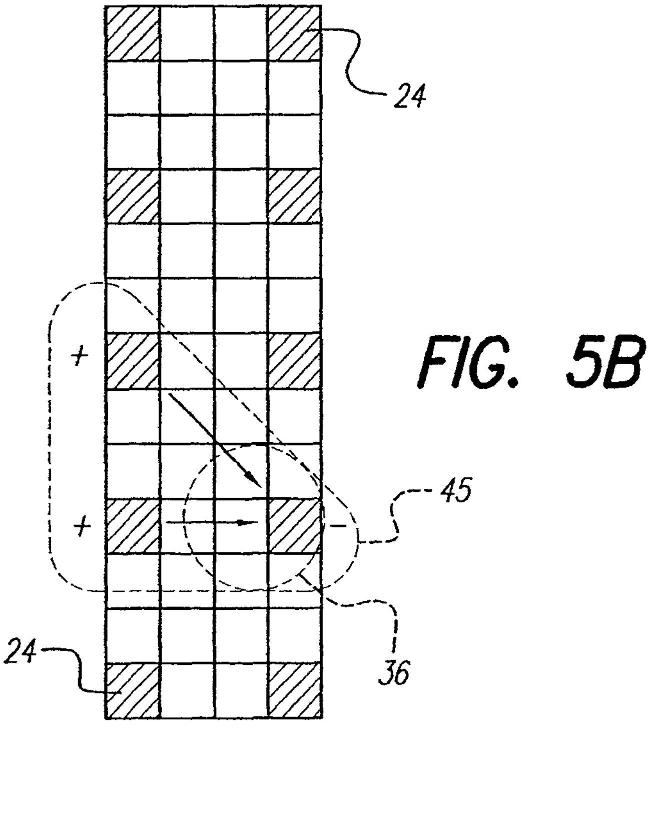
FIG. 5B illustrates one type of electrode grouping that may be achieved with the invention.
Figure 5A:
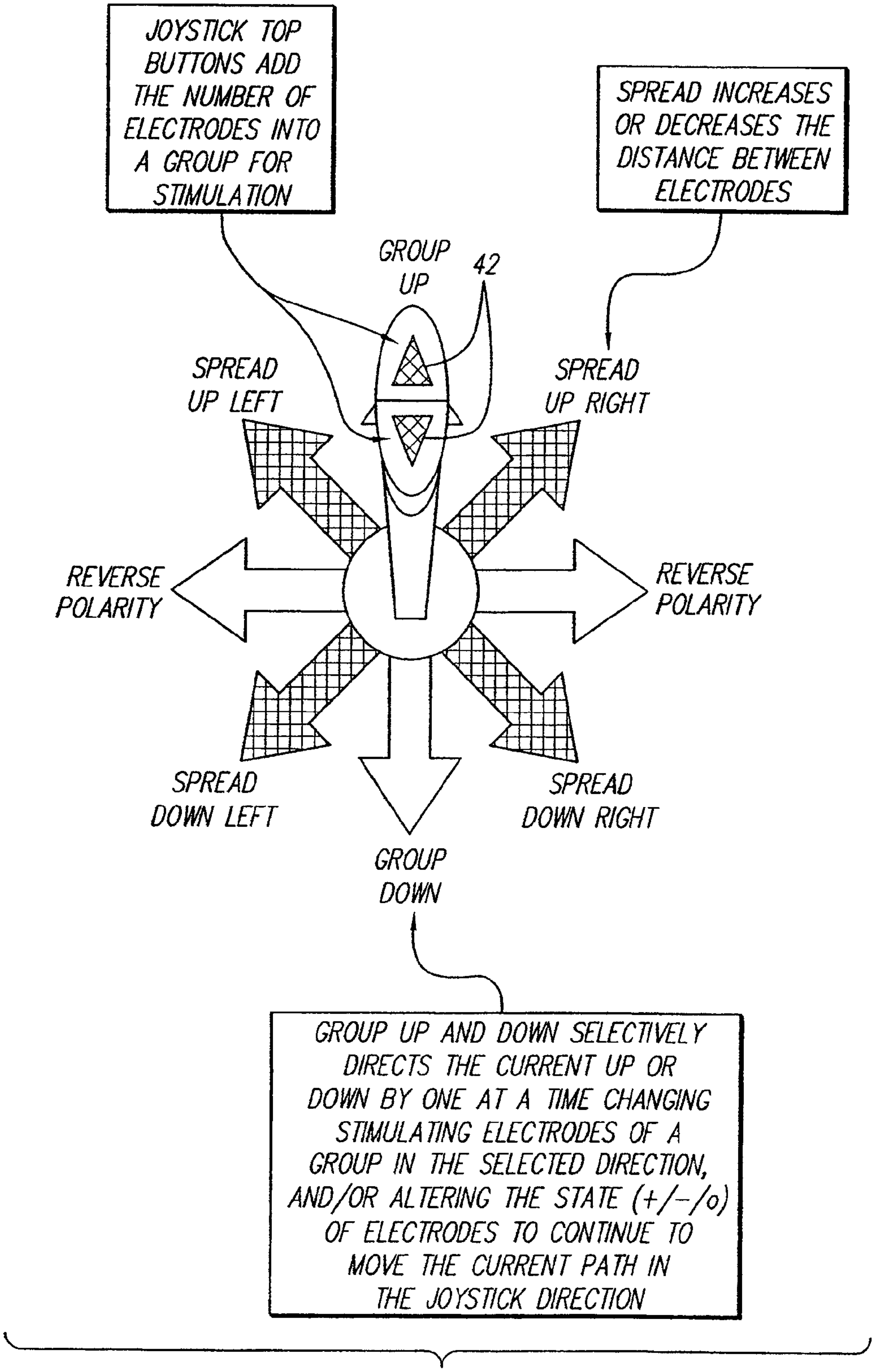
FIG. 5A schematically illustrates the various functions provided by the directional-programmer device.

In FIG. 5B, for example, an illustration is given of two columns of five electrodes 24. The selected group 45 of electrodes comprises two electrodes in the left column (second and third from the bottom), which are set to a "+" polarity, and one electrode in the right column (second from the bottom) which is set to a "−" polarity. This polarity and grouping creates an electric field which will cause electrical current to flow from both of the "+" electrodes to the single "−" electrode, which in turn defines a stimulation area 36 that is nearer to the right column than the left column, and that tends to be more concentrated nearer the "−" electrode.

Next, as illustrated in FIG. 5A, it is seen that the joystick 12 (or other directional programming device) can move a group selection of electrodes up and down within the array, which thus moves the field 36 up or down the spinal cord respectively. As the joystick 12, or other directional input device, is maneuvered forward, for example, the current field is steered up the spinal cord. This occurs, in one embodiment, by moving the selected group of electrodes up one level along the array. Because stimulation is generally associated with the cathode, or negative polarity electrodes, the stimulation can also be distributed among a group of electrodes by changing positive polarities to negative, and negative to positive, in the path of the direction programming within the group.

For even finer control of current steering, the amplitude of a group 45 of electrodes which includes more than a single anode and cathode is assigned a "group amplitude". The group amplitude is, in effect, a cumulative amplitude and might be, e.g., 5 mA, which is the absolute value total for all of the cathodes (−electrodes) in a single stimulating group. Thus, if a group of electrodes consists of four electrodes, including 2 anodes and 2 cathodes, the default value for such group might be −2.5 mA on each negative electrode, and +2.5 mA on each positive electrode. As the joystick 12 moves the stimulation area in an upward direction, the amplitude distribution is graduated to the higher anodes and cathodes until the lower anodes and cathodes are eventually turned off, after which the next higher electrodes start increasing in amplitude as the joystick 12 is held in the forward potion. This process is explained more fully below.

Figure 6A:
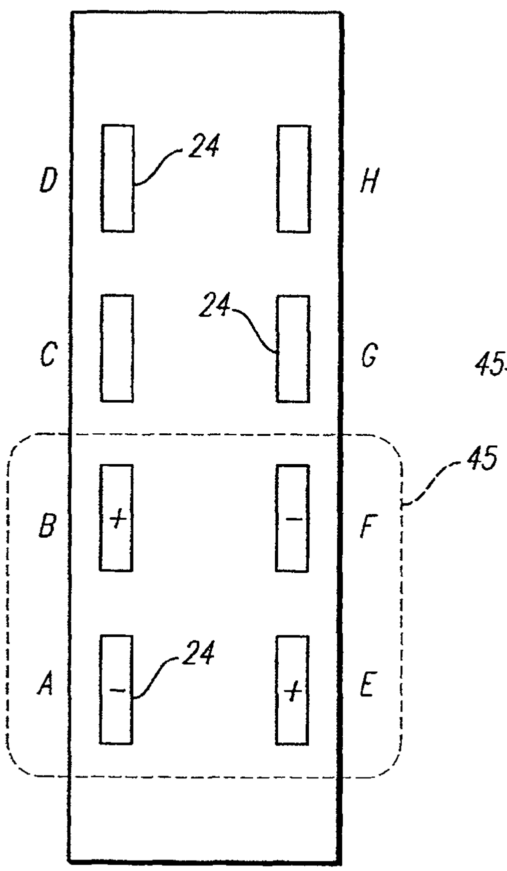
FIG. 6A illustrates a representative electrode array usable with the invention having eight electrode contacts.

By way of illustration, reference is made to FIG. 6A, which shows a four electrode group 45. Electrodes A and F each have −2.5 mA flowing to the electrode, totaling −5 mA, and electrodes B and E each have +2.5 MA flowing from the electrode. Hence, each polarity totals an absolute value of 5 mA. As the joystick 12 is moved forward, causing the electrodes C and G to be included in the group 45, and the electrodes A and E to be excluded from the group 45, the current flowing through electrode B and F each increases toward an absolute value of 5 mA, while electrodes A and E decrease toward 0 mA. As soon as electrodes A and E reach zero, electrodes C and G begins to increase toward an absolute value of 5 mA, while the electrodes B and F decrease toward zero. In this manner, the joystick 12 is able to steer the current up or down to a desired stimulation area 36. Note that current may also be steered in this manner left or right, although this is only possible when there are at least two rows of electrodes. The objective of directional programming is simply to steer current in the direction desired within the constraints of the electrode array(s) and pulse generator(s) by automatically configuring electrodes by defining or controlling the state (positive, negative, or off) of each electrode and by distributing current, including amplitudes, among the ON electrodes.

Another function available with directional programming, which could be linked to a separate direction input mechanism, is illustrated in FIG. 5 as field "spread" on the off-axis directions of a combined joystick 12. This directional input of the "spread" feature increases or decreases the current path, or the distance between selected electrodes. This affects the stimulating field by having a broader expanded field or a more focused field. To spread the field in a particular direction, for example, certain electrodes are locked in position, while others are moved in the direction of the spread desired. Referring to the four electrode group identified in FIG. 6A, including electrodes A, B, F and E, the following process is used: to move the spread up, electrodes A and E are held, while F and E are switched to C and G. In this manner, the positive to negative current path is lengthened, and the spread is increased. It is to be understood that there are many ways to organize the effect of directions to electrode configuration changes, all of which are included within the spirit of the invention. It is the use of a directional input device, or directional signals however generated, to automatically reconfigure electrodes for directing or steering current, whether to move a field, spread/focus a field, or concentrate a field for stimulation, that comprises the essence of the invention.

The constraints of the directional programming for the selection of electrodes depends on the lead style being used as well as the pulse generator. For example, a single in-line lead, such as is shown in FIG. 6C, would not have any left-to-right steering mobility. On the other hand, if two in-line leads are placed with electrodes in parallel, which would be input to the system, there would be left-to-right current steering possibilities. Likewise, use of existing pulse generators, such as the Itrel II pulse generator manufactured by Medtronic, would not be able to include more than four electrodes in a group.

The electrical current information for the electrode group 45 is transmitted by the RF signals to a receiving coil inside the stimulator 20 by a transmission coil 28 connected to the programmer 10 via a cable 30 (as shown in FIG. 3). As has been indicated, the advantage of using the joystick 12 (or other directional programming device) is that the clinician never has to manually select each possible combination of electrodes 24, or manually select each possible combination of electrodes 24, or manually input the desired stimulation parameters associated with each electrode selection. The initial parameters associated with the stimulation can be set, and then, by using the joystick 12, different electrode combinations can be selected while the clinician observes an immediate response from the patient, or alternatively the patient can directly operate the system. This allows the operator to move toward or away from certain joystick 12 maneuvers, with the electrical current for each of the electrodes 24 being reconfigured automatically with the joystick (directional programming) software.

In one embodiment, the operator adjusts the pulse amplitude (in milliamps, "mA"), the pulse width (in microseconds, "μS"), or pulse repetition rate (in pulses per second, "pps") of the pulses that are delivered to the group of electrodes selected by the joystick 12 using the simulated "slide switches" 35, 37 and 39 displayed on the screen 16. The amplitude is set for a "stimulation" channel, a single but alterable stimulation field. The channel amplitude is distributed among electrodes (+/−) as they are added or subtracted into the channel's electrode group with respective polarities. In this manner, the operator may simply maneuver the selected group 45 of electrodes to a desired area using the joystick (or other directional device), and make adjustments in the pulse width, pulse amplitude, and pulse repetition rate, and observe whether favorable or unfavorable results are achieved.

For some embodiments, the configuration software automatically makes configuration adjustments as a function of the stimulation parameters selected. For example, if the amplitude of the current stimulation pulses is set to a high value, then the size of the group 45 of electrodes included within the selected group may swell or increase, e.g., to four or five or more electrodes (from a nominal group size of, e.g., three electrodes); whereas if the amplitude of the current stimulation pulses is set to a low value, the size of the group

45 of electrodes included within the selected group may decrease, e.g., to one or two electrodes.

In one embodiment, the configuration software selects the size of the group 45 of electrodes in the manner illustrated in FIG. 5A. As seen in FIG. 5A, the electrodes are configured to move the stimulation field up by moving the joystick arm up, to move it down by moving the joystick arm down, to move it right by moving the joystick arm right, and to move it left by moving the joystick arm left. The relative size (number of electrodes within the group) of the group of electrodes is set by depressing one of two selector buttons 42 (increasing or decreasing) on top of the joystick arm (or otherwise positioned near the directional-programming device). The selected size may then be spread up and left by moving the joystick arm up and to the left; may be spread down and left by moving the joystick arm down and left; may be spread down and right by moving the joystick arm down and right; or may be spread up and right by moving the joystick arm up and right.

Figure 6B:
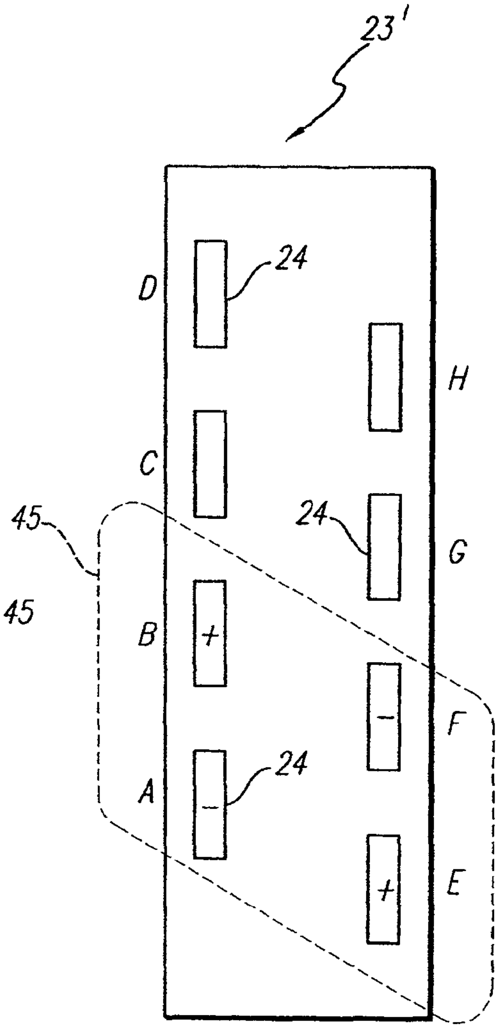
FIG. 6B illustrates an alternative electrode array usable with the invention.
Figure 6C:
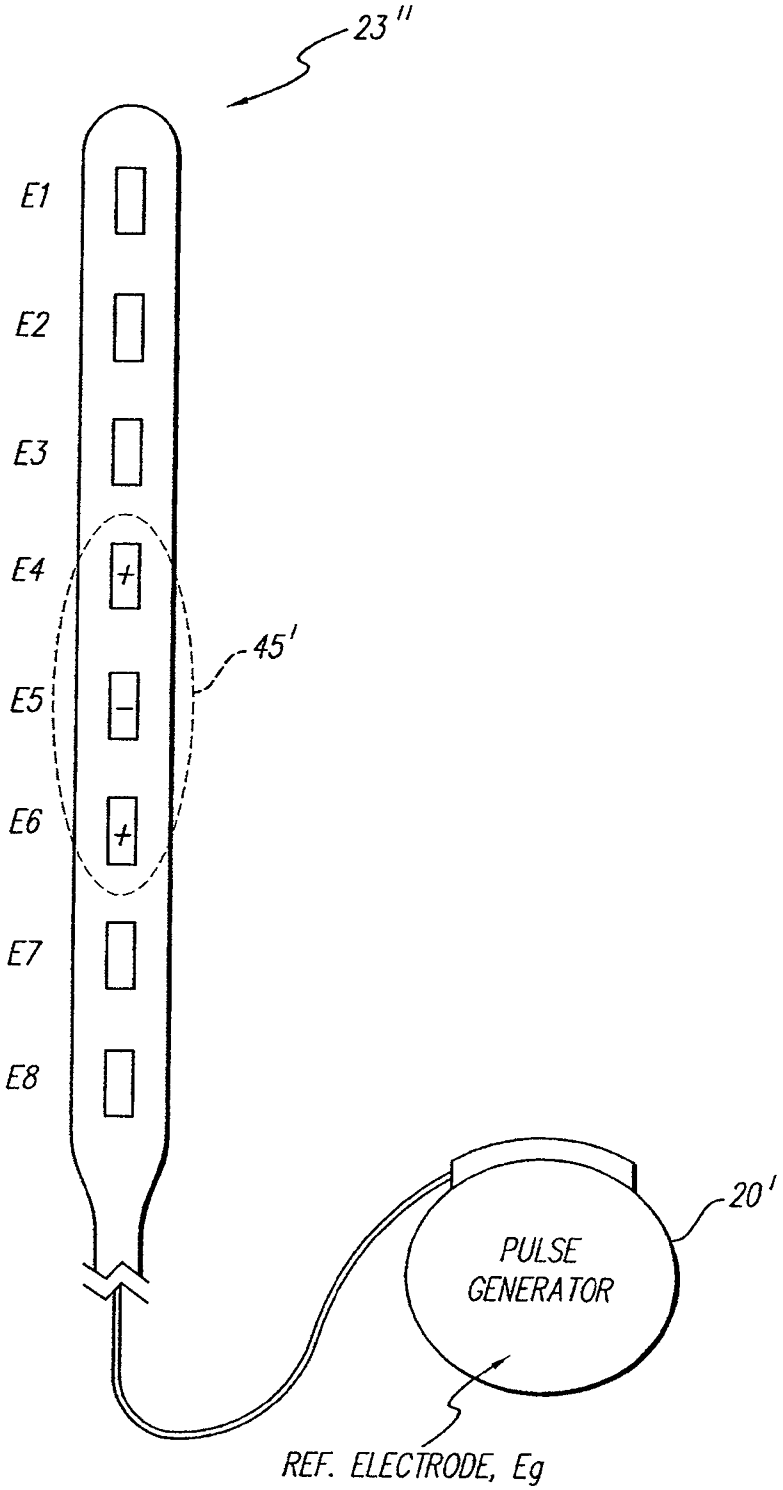
FIG. 6C illustrates yet another representative electrode array usable with the invention.

FIG. 6B illustrates an alternative embodiment of one type of electrode array 23' that may be used with the invention. In FIG. 66, the individual electrodes A, B, C and D included in the left column of electrodes are offset from the individual electrodes E, F, G and H included in the right column of electrodes.

FIG. 6C depicts yet another embodiment of an electrode array 23" that may be used with the invention. In FIG. 6C, electrodes E1, E2, E3, E4, E5, E6, E7, and E8 are arranged in a single column to form an in-line electrode array. The in-line array shown in FIG. 6C is electrically connected with a pulse generator 20'. The case of the pulse generator 20', or at least a portion of the case of the pulse generator 20', may be electrically connected as a reference electrode, Eg (see FIG. 2). By way of example, a group 45' of electrodes may include electrodes E4, E5 and E6, with electrodes E4 and E6 being positive electrodes, and electrode E5 being a negative electrode. The group 45' could "swell" to a larger group by including electrodes E3 and E7 in the group. Alternatively, the electrode group 45' could decrease to a smaller group by removing electrode E3 or electrode E7 from the group. The electrode group 45' could move up the electrode array by gradually deleting electrode E6 from the group while at the same time gradually including electrode E3 in the group, until such time as the group includes electrodes E3, E4 and E5. Continued movement of the electrode group up the array could continue by gradually deleting electrode E5 from the group while at the same time gradually including electrode E2 in the group. The inclusion and deletion of electrodes within the group is preferably accomplished in small steps, while maintaining current balance and perceived stimulation levels, as explained more fully below.

The present invention is preferably practiced using a stimulating system, e.g., an SCS system, that includes individually programmable electrodes. That is, it is preferred to have a current generator wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. With a single output source, the finest shifting of amplitude between electrodes is a total shift of the field from one or more selected electrodes to the next configuration. With two output sources, finer control can be achieved by gradually reducing output on one or more electrodes to be deleted from the group, and proportionately increasing the outputs on the electrodes to be included within the group. When as many output sources as electrodes are available, even finer shifting (smaller steps) may be achieved on each of the electrodes included in the shifting process.

In accordance with one aspect of the invention, a method of programming is provided wherein current (via current or voltage regulation) is shifted between two or more electrodes. The method begins with setting an amplitude level, in addition to other parameters such as pulse width and rate, as is currently done in practice. Advantageously, the amplitude level may be set in one of two ways: (1) using a fixed output value (standard method), or (2) using normalized output values (a new method).

As indicated, the amplitude level may be set using a fixed output value, such as 3 mA, or 3 Volts. Although it is possible to use a fixed amplitude value with the programming method described herein, there are disadvantages that will be apparent as the programming method is further described.

The amplitude level is preferably set using normalized output values, as described, e.g., in the '167 provisional application, previously referenced. This approach provides a normalized amplitude across electrodes with respect to patient thresholds. To better understand the normalized amplitude approach, it will be helpful to review how programming is currently performed. Currently, a patient or clinician adjusts the actual amplitude value, e.g. in voltage units within the range of the system capability. For example, the output on electrode E1 may be set to 3 volts, the output on electrode E2 may be set to 4 volts, and the like. However, an electrode array with n electrodes in a row (E1-En) on the spinal cord will likely have a variety of perception thresholds and maximum comfortable thresholds for each possible electrode at a given location in each possible combination. In a system that has an output range of 1-10 mA, for example, a patient might first perceive stimulation at 1 mA on E1 and might begin to feel uncomfortable stimulation at 5 mA. Likewise, electrode En might have a perception threshold (PT) of 2 mA and a maximum threshold (MT) of 4 mA. Thus, the first perception level of stimulation, or the lowest perceptible stimulation, may be different for electrode E1 than it is for electrode En; and the highest comfortable level of stimulation may also be different for electrode E1 than it is for electrode En. If a fixed value were to be set, e.g., 3 mA, and switched between electrodes, not only would the location of sensation change, but so would the intensity of the perceived stimulation.

The present invention, through use of normalized output levels, advantageously normalizes stimulation levels to perception. That is, a programmable amplitude range is utilized having an arbitrary scale, e.g., 0-10 (or min-max), with n steps. This arbitrary scale is then correlated to an actual current or voltage value. A zero level is equal to zero mA; a level one (or minimum level) is set to be equal to the perception level; a level 10 (or maximum level) is set to be equal to a maximum threshold level (i.e., the threshold level at which the patient begins to experience discomfort or pain). Thus, for example, setting the output of a given electrode to level 5 would place the output current stimulus (or voltage) so as to proportionately fall in the middle of the comfort zone for each electrode. Thus, using normalized intensity levels based on thresholds to control stimulation output comprises an important part of the present invention. In order to use normalized intensity levels based on threshold, a brief recording of the thresholds to be used in the programming equipment must initially be made.

In addition, electrode thresholds vary with the anodic and cathodic combinations. Typical electrode configurations are monopolar (one electrode paired with the implantable pulse generator, IPG, case ground), bipolar (a relatively close +− pair of electrodes), and multipolar (e.g. +−+). It is generally impractical to collect and record each threshold of each electrode in every possible combination to use in the programming of a stimulator. However, it has been found in the spinal cord that the bipolar thresholds, monopolar thresholds, and tripolar thresholds follow a similar trend. Thus, it is possible to record a minimal subset of thresholds, and then interpolate or estimate the remaining thresholds for each possible combination.

Normalizing amplitude for programming a stimulation system, such as an SCS system, is thus an additional feature of the present invention, although it is not required to practice the invention. Normalized amplitude programming offers an advantage because in order to recombine electrodes without manually resetting the amplitude to ensure a comfortable stimulation level, the normalized amplitude will aid in automatically calculating actual current or voltage amplitudes for recombined electrodes. Stimulation perception is also a product of pulse width, however, and pulse width should also be included in any threshold estimations or adjustments. Also, it should be noted that the same normalizing method may be used for motor thresholds instead of perception thresholds in applications where motor function is being achieved (FES).

Thus, it is seen that the present invention includes, inter alia, the setting of amplitudes and/or pulse widths during programming on selected electrodes based on normalization to perception values, with the ability to discriminate between various configuration types to adjust the threshold ranges. That is, the invention includes a means to increase the amplitude and/or pulse width, a means to record the thresholds for selected electrodes, and a means to estimate and/or interpolate thresholds for unrecorded electrodes in any given combination.

A preferred means to accomplish the above functions includes a software program that steps the patient or clinician through a process that records a minimum set of threshold values required to estimate the remaining thresholds to be used in the programming of the stimulator (i.e. a software wizard or a threshold user interface screen). Another means comprises use of a hardware device that has a location to identify the minimum and maximum thresholds for a given set of electrodes.

Currently, to Applicants' knowledge, threshold data is not recorded nor used to drive the programming of multiple electrode combinations. Instead, an electrode combination is selected, the amplitude is turned up from zero to a comfortable level, the patient responds to where the stimulation is felt, and the process is repeated for as many combinations as can or would be tried. This is true for manual selection or computer generated electrode selections.

An example of an equation that may be programmed into a processor and used by the invention to normalize amplitude levels is as follows:

X=Amplitude Level (0-10), 0 level=0 mA $I_i$=Current Amplitude, mA for electrode I of n $P_i$=Perception Threshold, mA for electrode I of n $M_i$=Maximum Threshold, mA for electrode I of n $F_i$=Fractional stimulation (±100%), % on electrode I of n For all cathodes (i.e. $F_i<0$):

$$I_i=F_i \times P_i \times X \text{ for } 0 \le X \le 1$$

and $$I_i=F_i \times [\{(M_i-P_i)/9\} \times (X-1)+P_i] \text{ for } X>1.$$

Note that:

$$\text{If } X=0, I_i=0$$

$$\text{If } X=1, I_i=\times P_i \times F_i$$

$$\text{If } X=10, I_i=M_i \times F_i$$

The total current for all cathodes is then:

$$I_{cathode} = \sum_{I=1, F_i<0}^{n} I_i$$

The current for anodes (i.e. $F_i>0$) is:

$$I_i=-F_i \times I_{cathode}$$

An example of output currents for different values of X using simple monopolar stimulation is as illustrated below in Table 1:

TABLE 1

| | Electrode | | | | | | | | |
|---|---|---|---|---|---|---|---|---|---|
| | E1 | E2 | E3 | E4 | E5 | E6 | E7 | E8 | CASE |
| $P_i$ (mA) | 2 | 3 | 3.3 | 2 | 2.2 | 2 | 3 | 4 | NA |
| $M_i$ (mA) | 10 | 12 | 12.7 | 11 | 10 | 9 | 11 | 12.7 | NA |
| $F_i$ (%) | | −100% | | | | | | | 100% |
| $I_i$ (mA) | | | | | | | | | |
| X = 0 | | 0.00 | | | | | | | 0.00 |
| X = 0.5 | | −1.50 | | | | | | | 1.50 |
| X = 1 | | −3.00 | | | | | | | 3.00 |
| X = 5 | | −7.00 | | | | | | | 7.00 |
| X = 10 | | −12.00 | | | | | | | 12.00 |

An example of output currents for multi-cathode stimulation is as depicted in Table 2, presented below:

TABLE 2

| | Electrode | | | | | | | | |
|---|---|---|---|---|---|---|---|---|---|
| | E1 | E2 | E3 | E4 | E5 | E6 | E7 | E8 | CASE |
| $P_i$ (mA) | 2 | 3 | 3.3 | 2 | 2.2 | 2 | 3 | 4 | NA |
| $M_i$ (mA) | 10 | 12 | 12.7 | 11 | 10 | 9 | 11 | 12.7 | NA |
| $F_i$ (%) | | −90% | −10% | | | | | | 100% |
| $I_i$ (mA) | | | | | | | | | |
| X = 0 | | 0.00 | 0.00 | | | | | | 0.00 |
| X = 0.5 | | −1.35 | −0.17 | | | | | | 1.52 |
| X = 1 | | −2.70 | −0.33 | | | | | | 3.03 |
| X = 5 | | −6.30 | −0.75 | | | | | | 7.05 |
| X = 10 | | −10.80 | −1.27 | | | | | | 12.07 |

A more complex example, involving multipolar stimulation, is shown in Table 3:

TABLE 3

| | Electrode | | | | | | | | |
|---|---|---|---|---|---|---|---|---|---|
| | E1 | E2 | E3 | E4 | E5 | E6 | E7 | E8 | CASE |
| $P_i$ (mA) | 2 | 3 | 3.3 | 2 | 2.2 | 2 | 3 | 4 | NA |
| $M_i$ (mA) | 10 | 12 | 12.7 | 11 | 10 | 9 | 11 | 12.7 | NA |
| $F_i$ (%) | | 10% | | −90% | −10% | | 90% | | |
| $I_i$ (mA) | | | | | | | | | |
| X = 0 | | 0.00 | | 0.00 | 0.00 | | 0.00 | | |
| X = 0.5 | | 0.10 | | −0.90 | −0.11 | | 0.91 | | |
| X = 1 | | 0.20 | | −1.80 | −0.22 | | 1.82 | | |
| X = 5 | | 0.60 | | −5.40 | −0.57 | | 5.37 | | |
| X = 10 | | 1.09 | | −9.90 | −1.00 | | 9.81 | | |

Another example of this implementation is:

E1: P=1 mA, M=4 mA

E2: P=2 mA, M=4 mA

If X=5, then:

E1=2.5 mA or E2=3 mA

If X=5 then:

If stimulation is 100% on E1, then E1=2.5. mA

If stimulation is 90% on E1 and 10% on E2, then E1=90%*2.5 mA and E2=10%*3 mA. Thus, if the level is set to X=5, and a shifting process moves the current field from E1 at 100% stimulation to 90% E1 and 10% E2 then the normalized values are proportionately shifted. The maximum shift would be from 100%*E1 to 100%*E2.

If normalized values are not used and X is set to 3 mA Then:

$$E1*100\%=3\text{ mA}$$

Or, $$E1(90\%)\text{ and }E2(10\%)\text{: }E1=2.7\text{ mA and }E2=0.3\text{ mA.}$$

A key part of the invention includes using a programming scheme to automatically switch electrode combinations, current distributions, etc. A suitable input mechanism, such as a joystick, or other input device, such as voice or sensor activation, may be used as the control input. Automatic preset shifting may also be used. In accordance with the invention, a suitable control mechanism (driven in software, hardware, and/or mechanical) is used to direct or steer stimulation (a current field) by combining anodic and cathodic electrodes in whole or in part of a given output. This requires independently programmable electrode outputs for at least two electrodes, and optimally n outputs for n electrodes. To illustrate, assume electrode E1 is selected as a cathode and electrode E3 is selected as an anode, either by default or manual selection. After the amplitude level is set (normalized or constant), current can be steered by automatically combining electrodes with various current distributions (depending on the stimulators capability). In a single row electrode, such as is illustrated in FIG. 6C, steering can only occur in the same axis. In a dual row (or more) electrode array, such as is shown in FIGS. 6A and 6B, an x-y axis can be steered. Additionally, a z axis can be included (depth of penetration by modulating intensity).

To shift current, the amplitude on a particular electrode is reduced proportionately to another electrode's increase. If, for example, a cathode electrode E1 has an amplitude of 3 mA (or 3V), the output can be reduced to 90%, 80%, etc., down to zero while another electrode E3 is increased to 3 mA starting from zero and increasing to 100%. The current summation in this case is always 3 mA.

The same shifting of current may also be accomplished with a normalized amplitude distribution among electrodes. Instead of applying a proportional increase or decrease on electrodes based on a constant total amplitude, however, the increase is proportional to the normalized level. This enables the shifting of current to stay at a relatively consistent perceptual intensity as the current field is directed to new locations. If, for example, a normalized "Level 5" (out of 10) is set, as cathodic current flow, and is shifted from the location of electrode E1 to the location of electrode E2, the intensity applied to electrode E1 beginning at 100% would have a value in the middle of the comfortable range (e.g., half way between the perception threshold and the maximum threshold). Should the threshold range for electrode E1 be 1 mA to 3 mA, then level 5 for electrode E1 would be 2 mA. Likewise, if the threshold range for electrode E2 is 3 mA to 5 mA, then level 5 for electrode E2 would be 4 mA. Thus, as current is shifted from electrode E1 to electrode E2 in a gradual manner, electrode E1 would be reduced by percentages of 2 mA (at level 5) as E2 is proportionately increased to its level 5, or 4 mA. Such can result in differing current summations as the current field is shifted, but there should be little or no perceptual change in intensity felt or sensed by the patient. If a constant current value of 4 mA were to be used instead of a normalized value, then as the current is shifted back from E2 to E1, the maximum threshold for the patient would be exceeded and could prove very uncomfortable for the patient. Thus, it is seen that by using a single current value, the current shifting could result in fluctuation intensity perceptions that can drop below the perception threshold or exceed the maximum tolerable threshold. To avoid this undesirable result, frequent adjustments in amplitude would have to be made during the shifting process. That is why use of the normalized value is preferred for the present invention: total amplitude adjustments may be automated while maintaining a comfortable stimulation perception.

It is noted that non proportional shifts could also be made, but such would be less optimal and would defeat the purpose or ease of calculation. However, if the shifting differences are minimal, such differences would not likely be perceived. An example of a non proportional shift is as follows: reducing E1 by 10% while increasing E2 by 20%, then reducing E1 by 20% while increasing E2 by 10%. Each shift is not proportional, but the shift ultimately results in a shift from electrode E1 to electrode E2, as is the case with proportional shifts.

Furthermore, it is noted that stimulation is typically driven by cathodic current. However, the positive and negative settings must equal zero. Any shifting of anodic electrode values must total the current on all of the cathodic electrodes, not perception thresholds. When shifting current fields using normalized levels, the combined current will fluctuate. Thus, proportional shifting of anodic values would not be based on the perception level, but on the total cathodic current. If driven by anodic current, then the opposite is true.

To move current from one location to another without having to set up each combination in a discretely tested process comprises a key element of the invention. Such is accomplished through use of a continuous current shifting process where stimulation is not interrupted. Several implementations of the continuous shifting process may be used. For example, the shifting process may include an algorithm that responds to an input signal indicating a directional move to calculate the next configuration to move current. The steering input device is used to indicate the next location of data to be used to calculate the electrode configuration. The data may be extracted from a "solve for" formula, or by locations on one or more tables advanced by the input device, or a combination of formulas and tables. In any case, the next configuration is predicated on, or calculated from, the previous configuration. Each input move configures the electrodes and distributes the current.

An example of a current shifting table-based algorithm used to shift current horizontally across an electrode array is illustrated in FIG. 7. In FIG. 7, as well as in FIGS. 8 and 8A-8Q (which show a table-based algorithm used to shift current vertically), explained below, the gray or shaded portion of the table represents that portion of cathodic amplitude value that is based on the normalized constant value set, whereas the white (non-shaded) portion of the table represents that portion of anodic current that is based on the sum of all the cathodic currents. The sequence of numbers arranged in a column along the left side of the table represent the discrete steps that are utilized in the shifting process, which steps are controlled by the user through an appropriate input mechanism, e.g., a joystick or equivalent device. Thus, in FIG. 7, at step number 1, the stimulus current (normalized to "1.0" in the table) flows from the anode (±) to the cathode (−) on the left side of the array. At step number 2, the anodic current (+) on the left is decreased 10%, the anodic current (+) on the right side of the array is increased the same amount, while the cathodic current (−) remains the same. Following this pattern, the anodic current (+) is gradually shifted from the left side to the right side while the cathodic current (−) is held at a constant value. Thus, at step number 11, all of the anodic current (+) has shifted to the right, while all of the cathodic current (−) remains on the left. Then, beginning at step 12, the cathodic current begins to shift in discrete steps of 10% from the left side to the right side, while the anodic current shifts in similar amounts from the right side back to the left side. This continues until at step 21 all of the cathodic current (−) has been shifted to the right side and all of the anodic current (+) is back to the left side. Then, while holding the cathodic current (−) constant on the right side, the anodic current (+) is shifted back to the right side in discrete steps of 10%, until at step 31 all of the anodic current (+) has been shifted back to the right side, resulting in a complete shift of the stimulus current from the left side of the array to the right side.

It should be noted that in the shifting algorithm shown in FIG. 7, as well as that shown in FIGS. 8 and 8A-8Q below, that the illustrated discrete step size of 10% is only exemplary. In practice, the step size could be smaller or larger than this amount, as desired.

Figure 8:
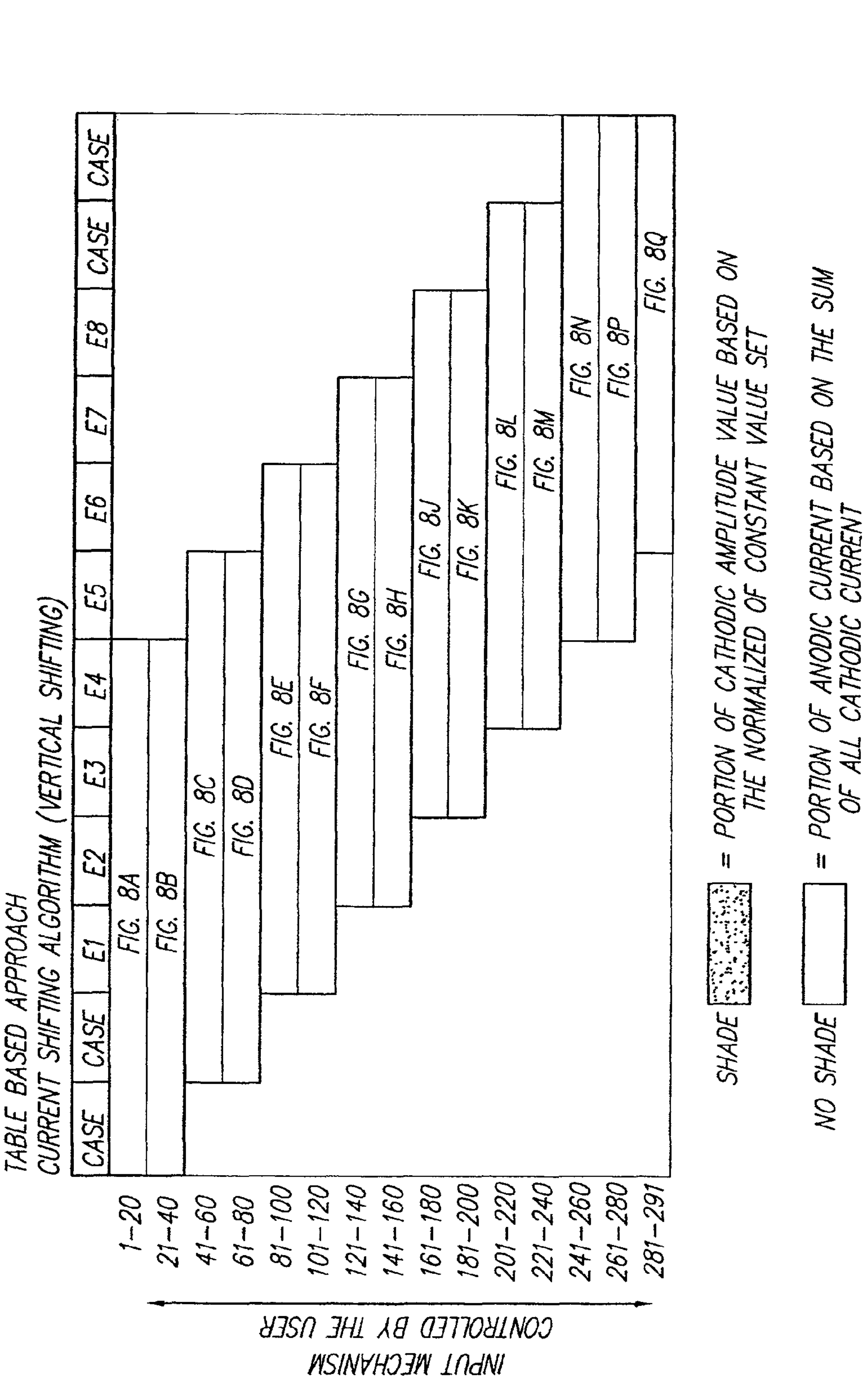
FIGS. 8 and 8A-8Q (note, there is no FIG. 8I or FIG. 8O) show a table-based current shifting algorithm for vertical shifting, with FIG. 8 providing a map to FIGS. 8A-8Q.
Figure 8G:
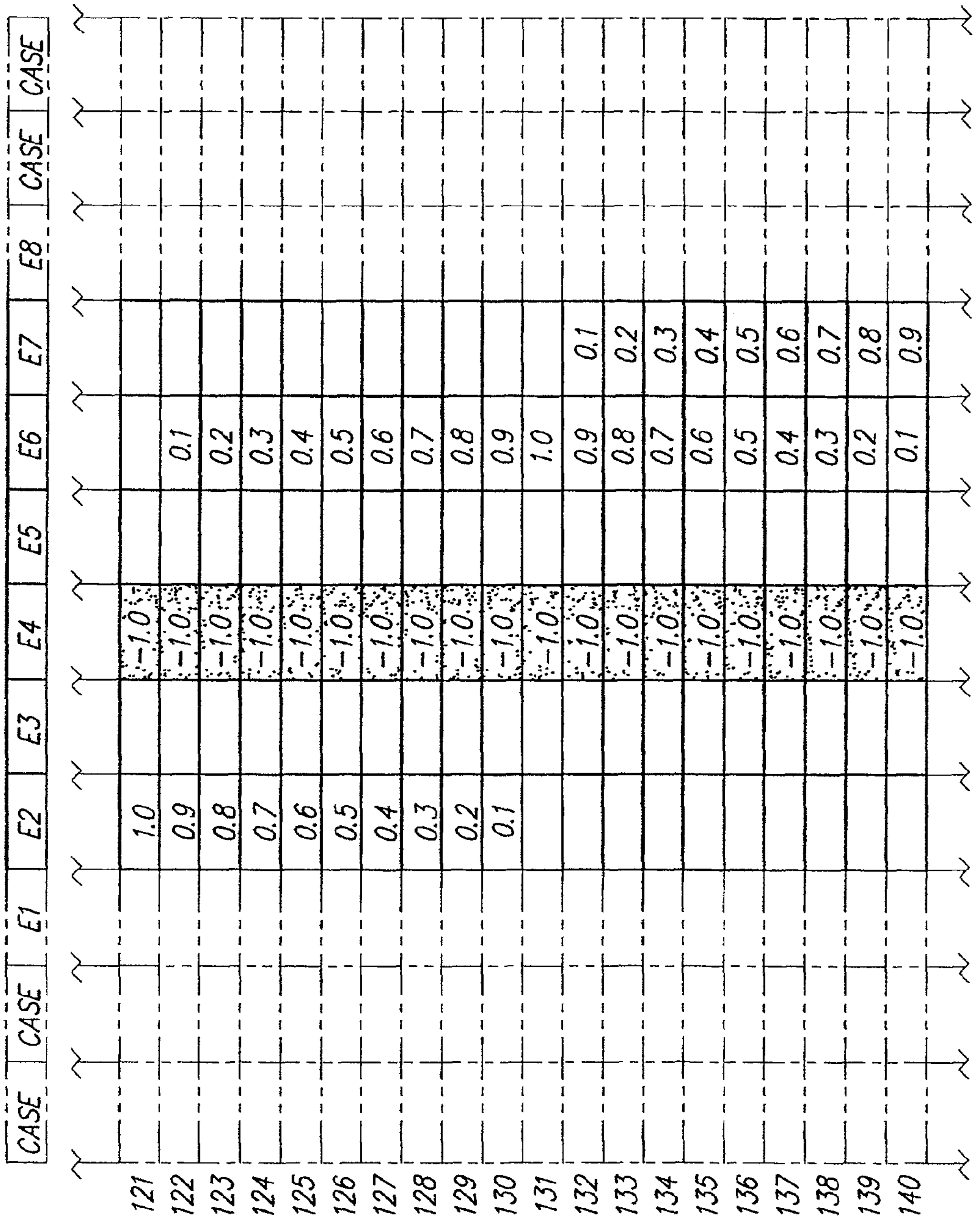
Figure 8M:
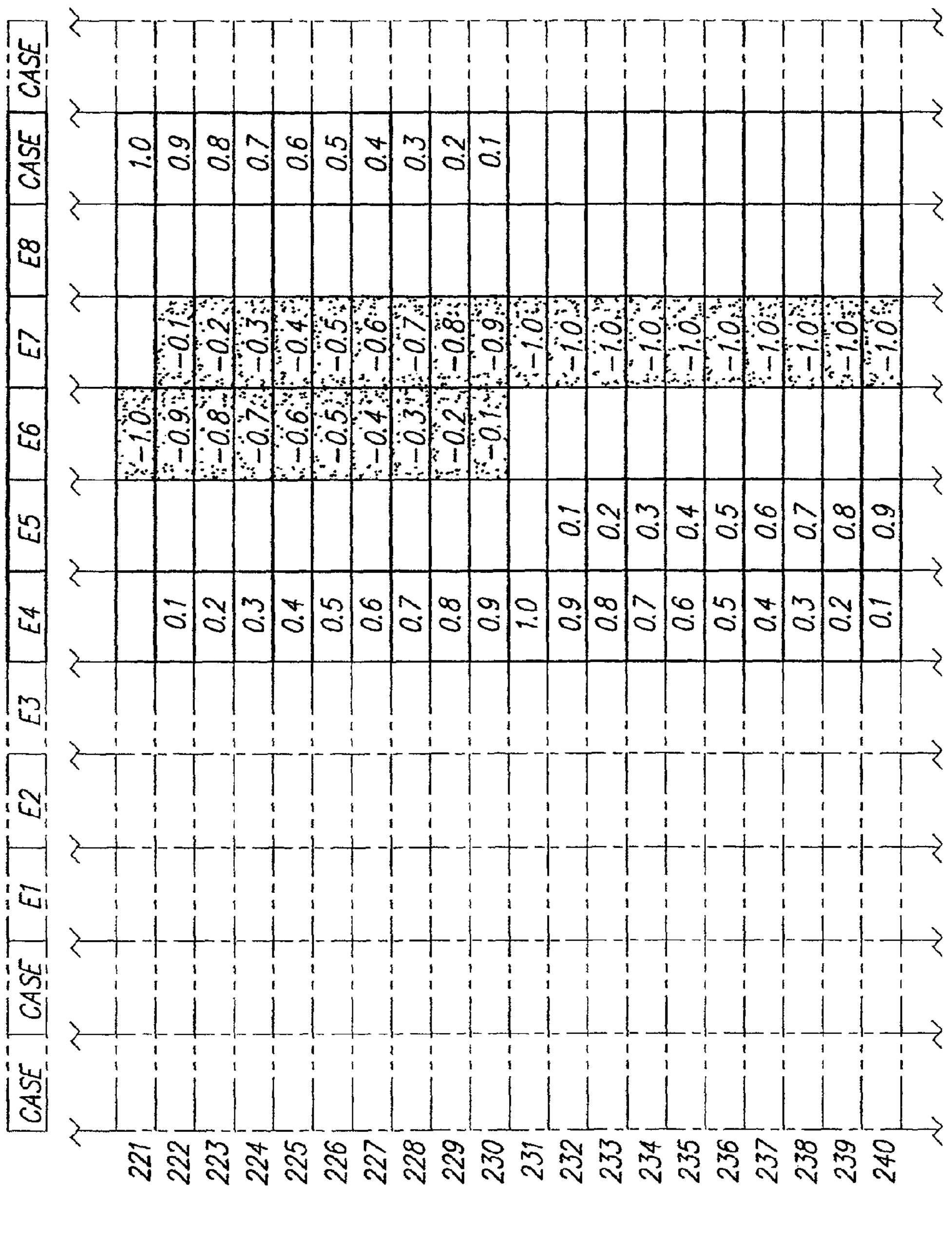
Figure 8N:
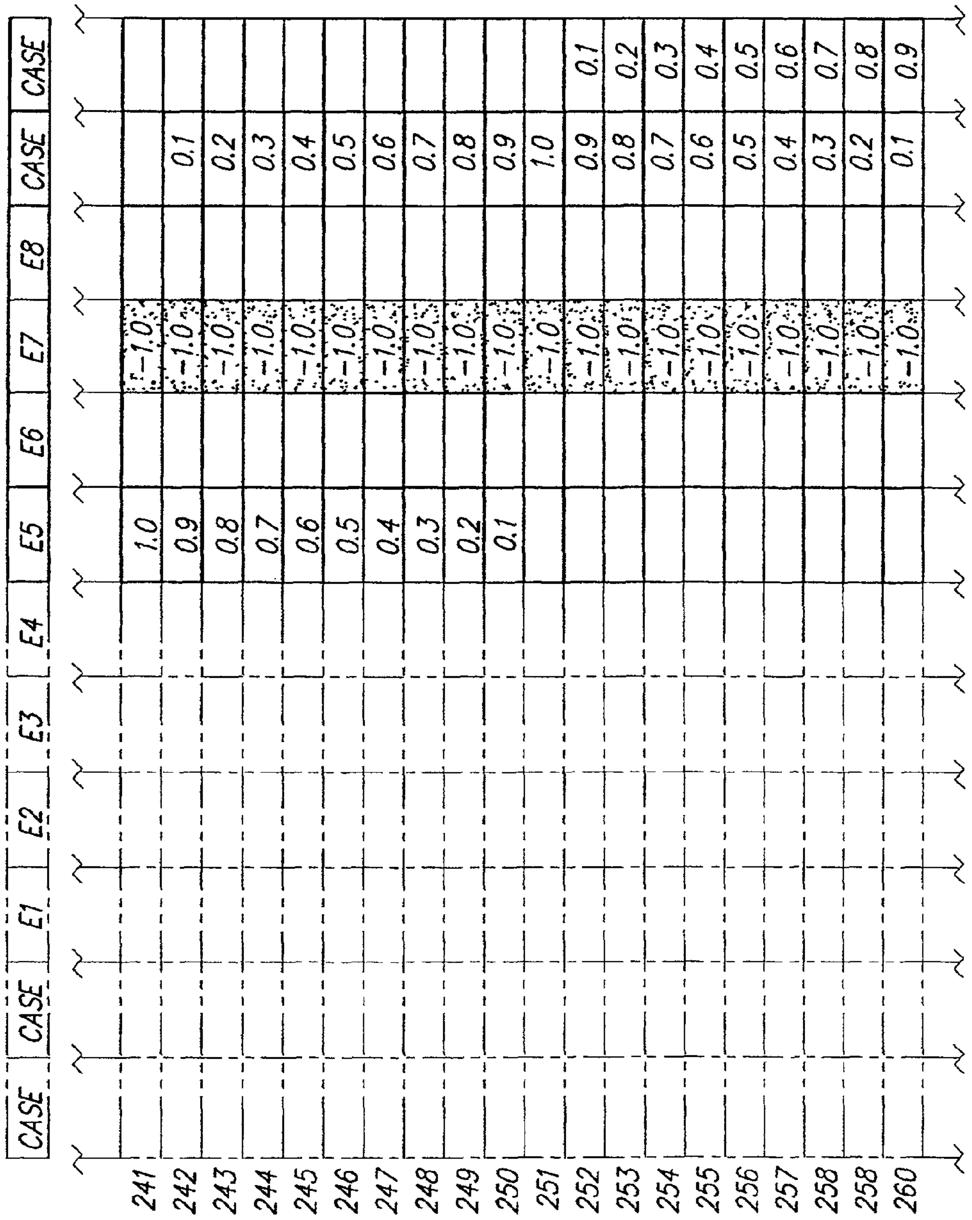
Figure 8Q:
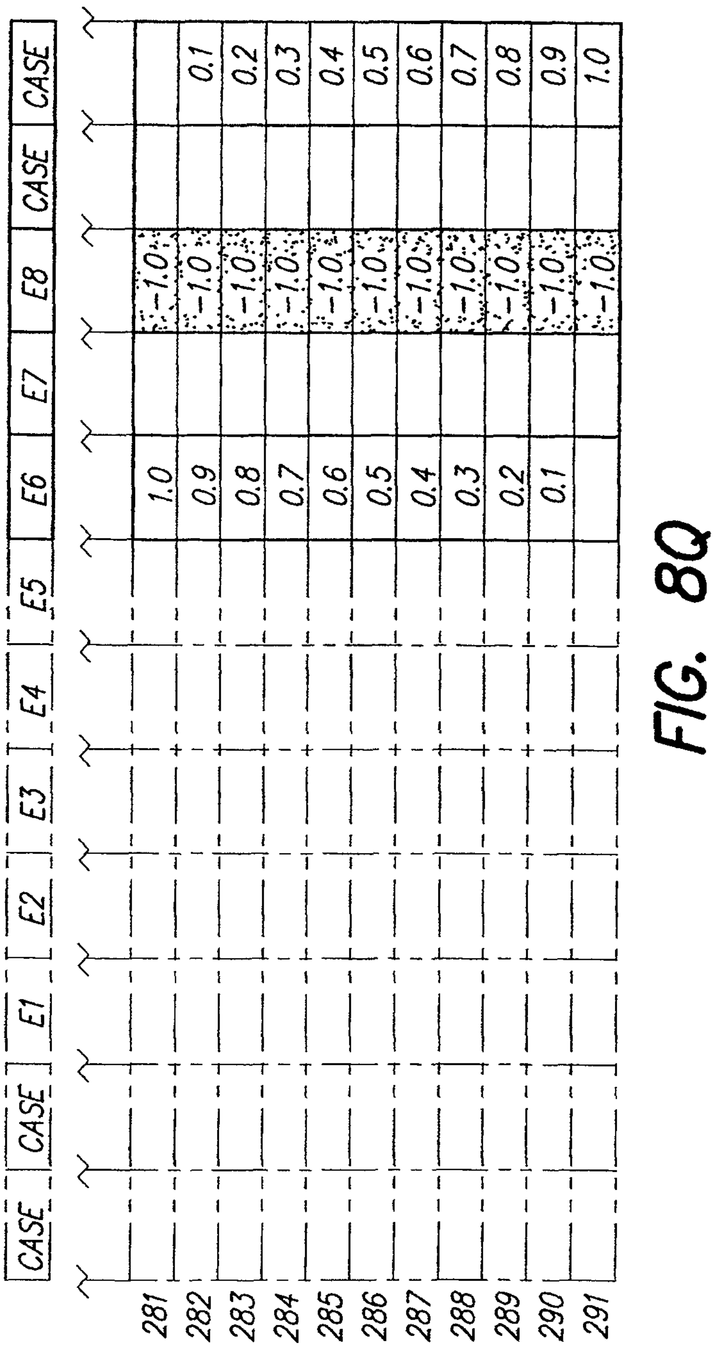

In a similar manner, FIGS. 8 and 8A-8Q illustrate an exemplary table-based algorithm that may be used to shift current vertically within an electrode array, e.g., up or down an in-line array of the type shown in FIG. 6C. For purposes of the example shown in FIGS. 8 and 8A-8Q, it is assumed that monopolar stimulation is present at electrode E1 (paired with the case electrode), and that it is desired to shift the stimulation vertically so that eventually monopolar stimulation is achieved at electrode E8 (paired with the case electrode). Starting at step number 1 in FIG. 8A, all of the anodic current (+) flows from the case electrode, and all of the cathodic current (−) flows to electrode E1. The anodic current (+) flowing from the case electrode is gradually decreased in small discrete steps of, e.g., 10%, while the anodic current (+) flowing from electrode E3 gradually increases in the same step sizes, until at step 11, all of the anodic current (+) has been shifted to electrode E3. Then, beginning at step 12, the anodic current (+) flowing from electrode E3 is gradually decreased in discrete steps of 10%, while the anodic current (+) flowing from electrode E4 gradually increases in the same step sizes, until at step 21 (FIG. 88), all of the anodic current (+) has been shifted to electrode E4. Beginning at step 22 the cathodic current (−) flowing to electrode E1 is gradually decreased in discrete steps of 10%, while the cathodic current (−) flowing to electrode E2 is gradually increased in discrete steps of the same value, while at the same time the anodic current (+) flowing from electrode E4 is gradually decreased in discrete steps of 10%, while the anodic current (+) flowing from the case electrode increased in discrete steps of the same value. Following this process, at step number 31, all of the cathodic current (−) has been shifted to electrode E2, while all of the anodic current (+) has been shifted back to the case electrode. Then, beginning at step 32, the anodic current (+) is gradually shifted to a second case electrode, until at step 41 all of the anodic current (+) has been shifted to the second case electrode.

Following a process similar to that described above, the cathodic current (−), which is generally considered as the current responsible for achieving a desired stimulation, is gradually shifted in small discrete step sizes, as shown in the balance of FIG. 8B, and continuing through FIGS. 8C-8Q, until at step number 291 of FIG. 8Q, the cathodic current (−) has been shifted vertically all the way to electrode E8 and the anodic current (+) is all flowing from the case electrode (monopolar simulation).

It is to be emphasized that the equivalent of using formulas and/or tables to configure electrodes and distribute current may be achieved through other means, such as the use of a mechanical switching matrix mechanically controlled by an input steering device, such as a joystick. It is submitted that those of skill in the art could readily fashion such a switching matrix, given the teachings provided herein.

Figure 9:
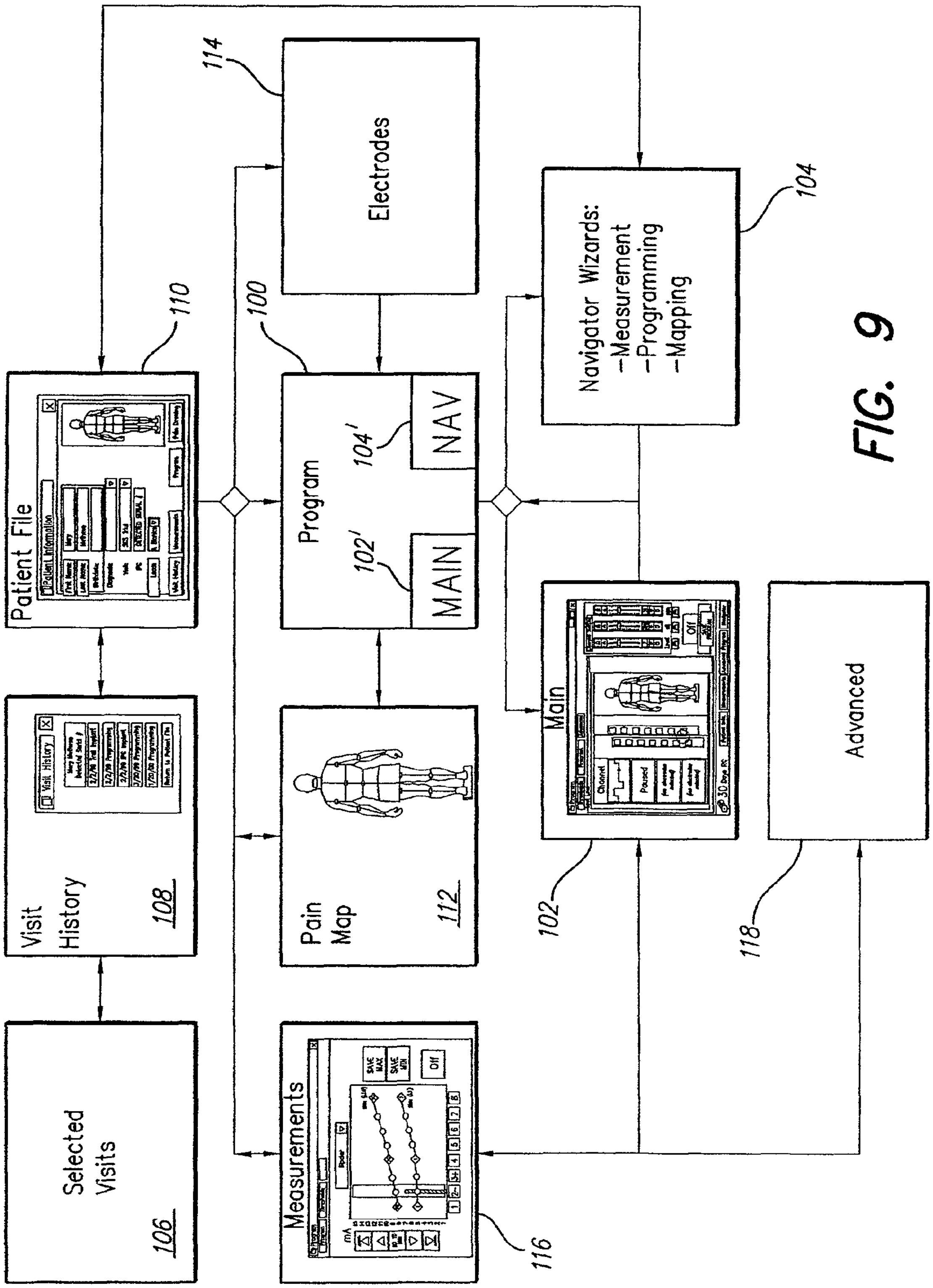
FIG. 9 is a block diagram of the software architecture used in an SCS system, or other neural stimulation system, in accordance with the present invention.

Turning next to FIG. 9, there is shown a block diagram of the software architecture used in a preferred embodiment of the present invention. As seen in FIG. 9, a core program 100 invokes other programs, e.g., subroutines and/or databases, as required to assist it as the stimulation system carries out its intended function. The core program 100 includes two sections: a main section 102' that invokes a main program 102 where the underlying programs that control the operation of the SCS system reside, and a navigator section 104' that invokes a Navigator Wizard program 104 where set up programs reside that aid the user as he or she initially sets up, i.e, programs, the system. That is, the Navigator Wizard program 104 facilitates programming the main program 102 so that the main program 102 has all the data and parameter settings it needs to carry out its intended function.

When invoked, the main program 102 provides stimulation pulses to the patient at selected electrode locations with stimulation pulses having a selected amplitude, pulse width, pulse repetition rate, and other control parameters. Being able to readily determine the optimum location where the stimulation pulses should be applied, and the parameters associated with the applied stimulation pulses (amplitude, width, rate) is the primary focus of the present invention.

Data files 106 and 108 track the patient's history, and patient file 110 provides patient data information. The information contained in patient file 110, e.g., patient name, address, type of stimulator, serial number of stimulator, etc., is generally entered by the physician or other medical personnel at the time the patient is first fitted with the SCS system. The data in the history file 108 keeps a chronology of when the patient visited the SCS physician and for what purpose, while the data in the selected visit file 106 provides detail data regarding what occurred during a given visit.

Figure 10:
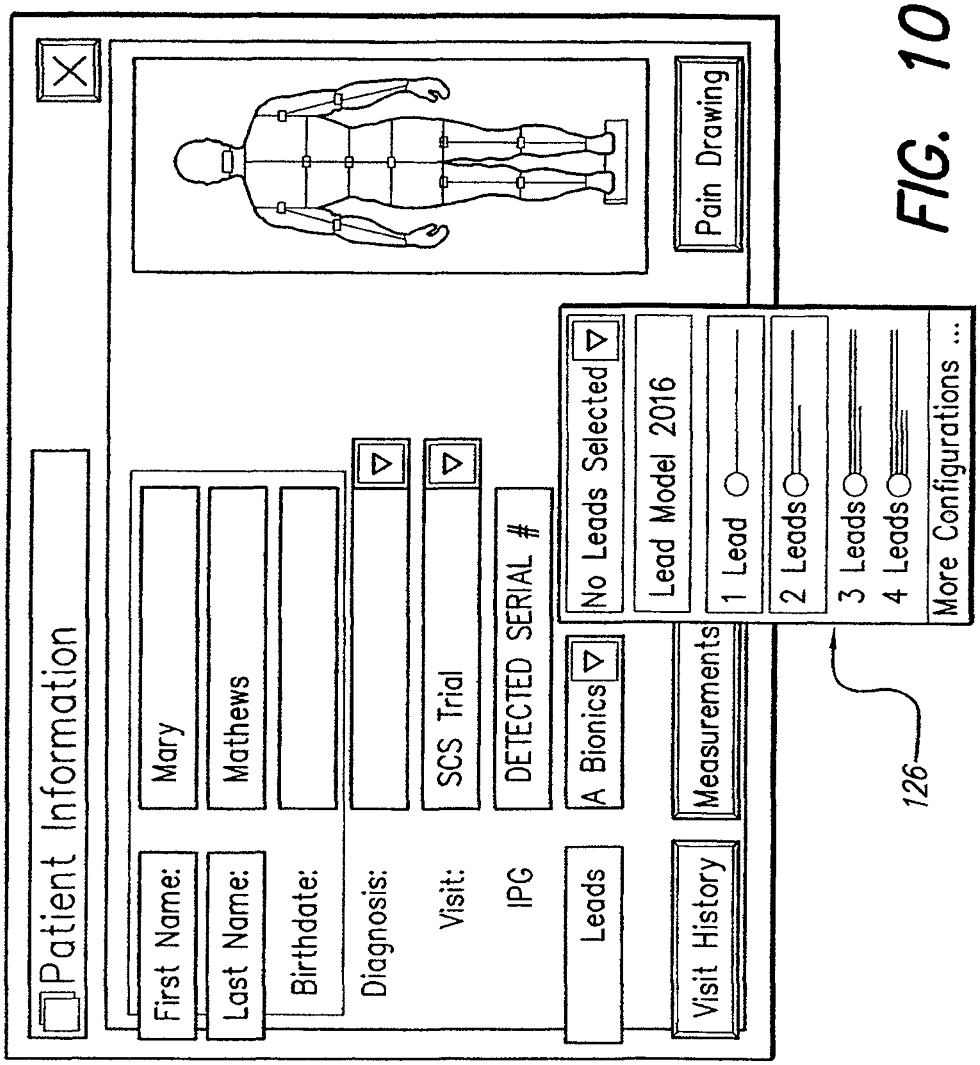
FIG. 10 depicts a representative patent information screen that may be used with the software architecture of FIG. 9.

An exemplary patient information screen display that is generated on the display screen 16 of a suitable programming device 10 (FIGS. 1A, 2 and 3) when patient information is entered or reviewed is shown in FIG. 10. Such patient information display allows information such as the patient name, birthday, purpose of visit, diagnosis resulting from the visit, lead (electrode) type, area of pain, and the like, to be displayed and/or entered into the system. Included on the particular screen shown in FIG. 10 is a drop down menu 126 that allows the user to specify the type of electrode array that the patient has, e.g., a single in-line lead, two in-line leads positioned end to end, two in-line leads positioned side by side, and the like.

Referring back to FIG. 9, a pain map file 112 contains the needed data for allowing the main programs 100, 102 to display a map of the patient's body. Using this map, the patient, or other programming personnel, may select those areas of the body where pain and/or paresthesia is felt.

An electrode file 114 stores data that defines the types of electrodes and electrode arrays that may be used with the SCS. Using the data in the electrode file 114, the physician or other programming personnel, can define the electrodes available through which stimulation pulses may be applied to the patient. Further, diagnostic testing of the available electrodes may be performed to verify that an electrode which should be available for use is in fact available for use.

A measurement file 116 stores and tracks the perception threshold and maximum comfort threshold that are either measured using the navigator wizard program 104, or calculated based on an interpolation of measured data by the main program 100.

An advanced program file 118 provides various programs and data needed to perform advanced functions associated with operation of the SCS system. In general such advanced functions are not that relevant to the present invention, and are thus not described in detail. The advanced program file 118 further provides a location where future enhancements for the SCS system operation may be stored and updated. For example, should an improved interpolation technique be devised to calculate threshold data stored in the measurement file 116, then such improved interpolation technique could be stored in the advanced program file 118.

A key feature of the present invention is the use of a navigator wizard program 104. The wizard program(s) 104 provides a software interface that advantageously walks the user step by step through the measurement and programming process. Additionally, to make the process even easier, and enjoyable, the wizard may use a map, akin to a treasure map, which is animated (akin to a video game) and incorporated into the fitting software. Alternatively, the treasure map, or other type of map, may be published as a printed document. The purpose of the animated treasure map, or printed document, or other software interface, as the case may be, is to detail the fitting procedure, and more particularly to graphically assist the clinician and patient as they search for the optimum program settings that can be used by the system to best treat the pain (or other neural condition) felt or experienced by the patient.

Figure 11:
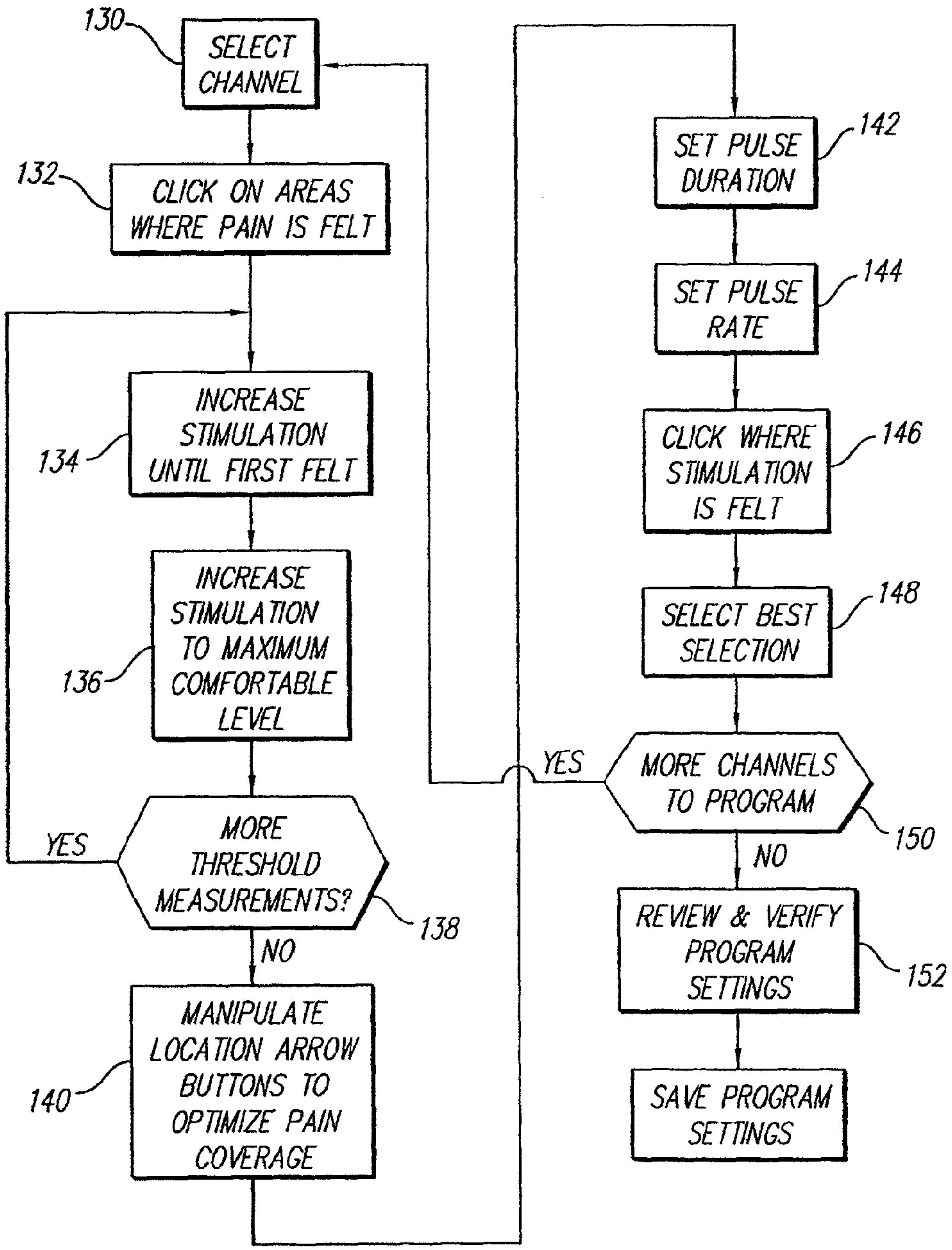
FIG. 11 is a flow chart that depicts the steps utilized by a software wizard in order to guide a user through the fitting process associated with an SCS, or other neural stimulation system.
Figure 12A:
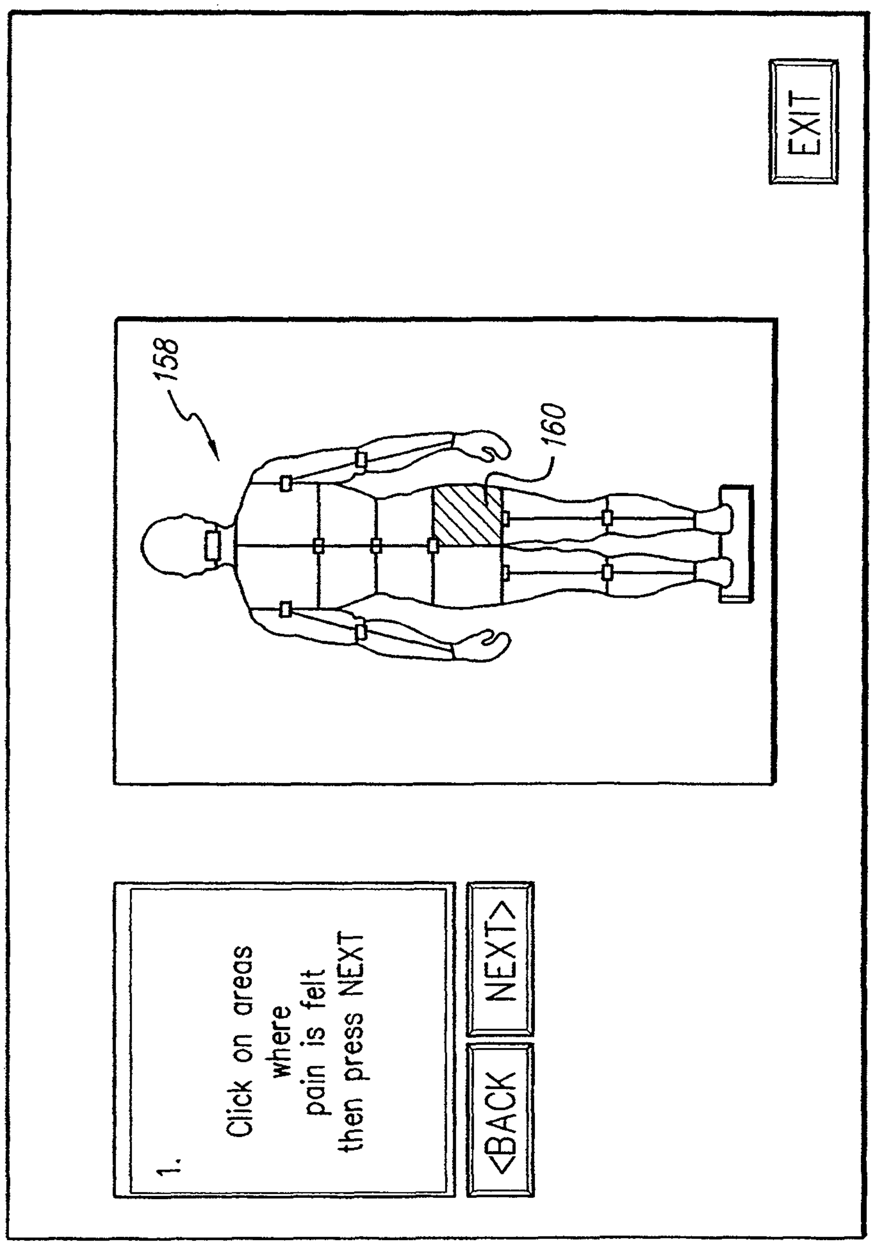

By way of illustration, the main steps carried out by a preferred measurement/programming wizard are illustrated in the flow diagram of FIG. 11. In a first step (block 130), the user is directed to select a stimulation channel. In some instances, there may be only one stimulation channel that is being used. In other instances, more than one stimulation channel may be used. Once the channel has been selected, the user is prompted to click on the areas where pain is felt (block 132). In one embodiment, this prompt is accomplished by displaying a screen similar to that shown in FIG. 12A. As seen in FIG. 12A, a patient body 158 is displayed having various stimulation areas 160 depicted. By clicking on one of the areas 160, it is shaded, or colored, in an appropriate manner to indicate that it has been selected. This selection activates electrodes which are, as a first try, believed to be the electrode(s) which can treat the pain area selected.

Figure 12B:
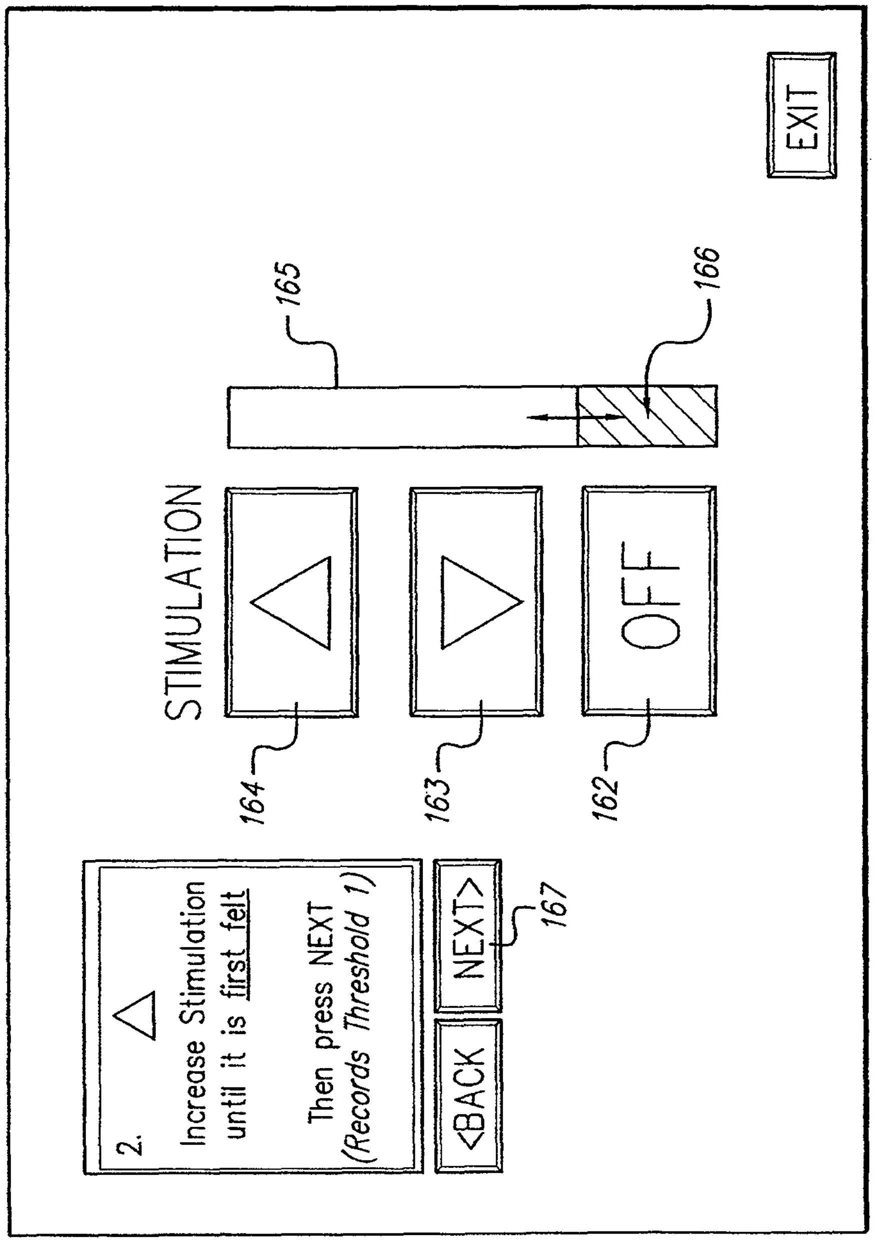

Referring back to FIG. 11, after the user has selected the areas where pain is felt, the user is prompted to increase the stimulation level until it is first felt (block 134). This step, in effect, measures the stimulation perception threshold. The user is prompted to measure this threshold, in one embodiment, by displaying a screen as shown in FIG. 12B. Such threshold measurement screen provides instructions to the user in the upper left hand corner. It also displays three buttons, an OFF button 162, a decrease button 163, and an increase button 164. By pressing (i.e., clicking) the OFF button 162, the user is able to selectively turn the stimulus current On of Off. Once on, the user can increase or decrease the amplitude of the stimulation current using the buttons 163 and 164. As he or she does so, a vertical bar graph 166, within a vertical window 165, increases or decreases in height, thereby providing a visual indication of the relative level of the stimulus current. Once the user has determined the level at which stimulation is first felt, the NEXT button 167 is pressed in order to advance to the next step in the process.

Figure 12C:
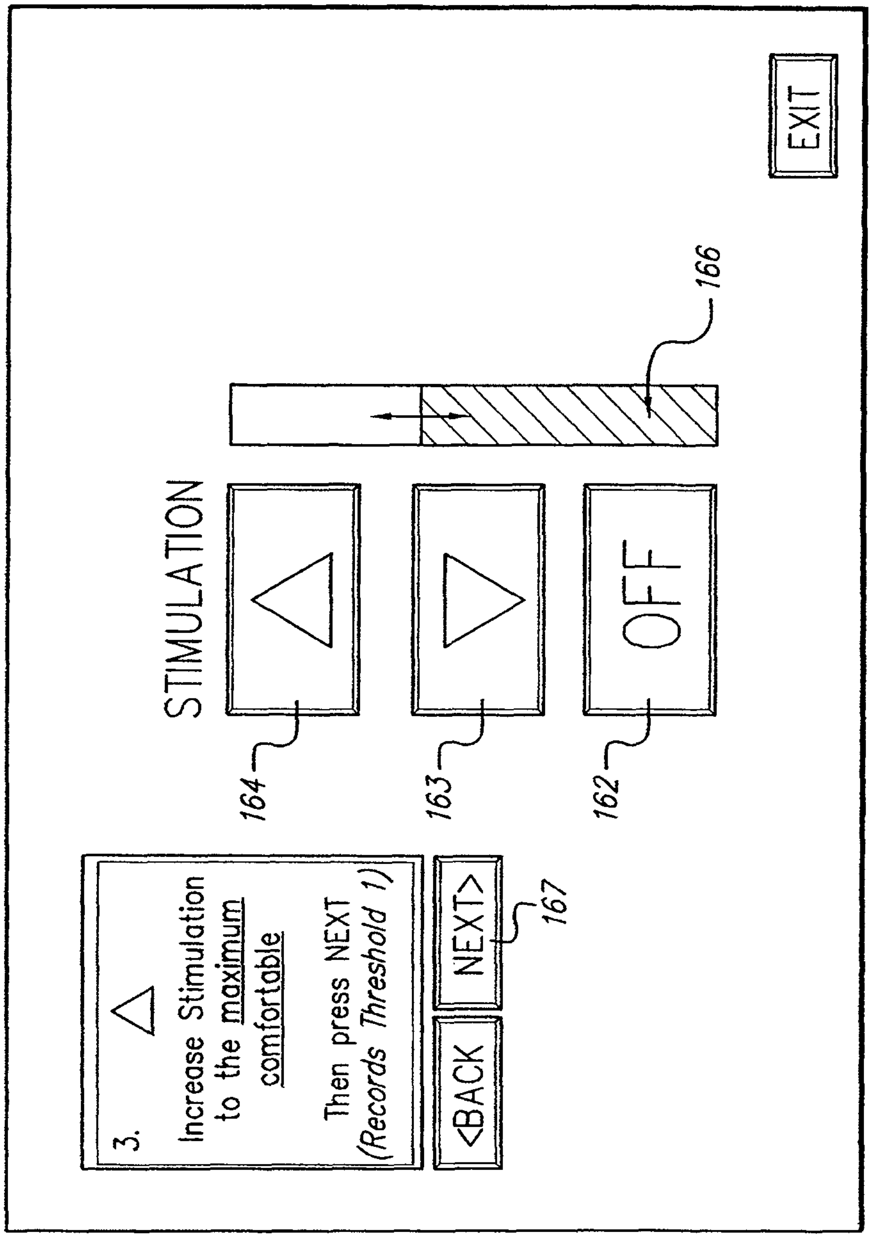

Returning again to FIG. 11, the user next increases the stimulation level until the maximum comfortable level is determined (block 136). This step thus measures the maximum comfortable stimulation threshold for the patient on the selected channel. To aid in this process, in one embodiment of the invention, a prompt screen as shown in FIG. 12C is displayed. The screen shown in FIG. 12C is essentially the same as the one shown in FIG. 12B except that different instructions are provided in the upper left hand corner. As the user increases the stimulation level to the maximum comfortable level, the bar graph 166 increases in height. Once the user has determined the maximum comfortable stimulation level, the NEXT button 167 is pressed in order to advance to the next step of the fitting process.

As seen in FIG. 11, the next step in the fitting process is to determine if more threshold measurements need to be taken (block 138). Typically, more than one electrode, or more than one grouping of electrodes, will be associated with the selected pain site. Hence, the first threshold measurements are taken for a first group of electrodes associated with the site, and second threshold measurements are taken for a second group of electrodes, and perhaps third threshold measurements are taken for a third group of electrodes. Typically, no more than about two or three groups of electrodes are used to determine thresholds, although more combinations than three could be measured for thresholds if desired. If every possible electrode combination were measured, the fitting process would take too long. Hence, in accordance with the teachings of the present invention, after two or three threshold measurements have been made, the threshold values for other possible electrode combinations associated with the selected pain site are calculated using interpolation or other suitable estimation techniques.

Figure 12D:
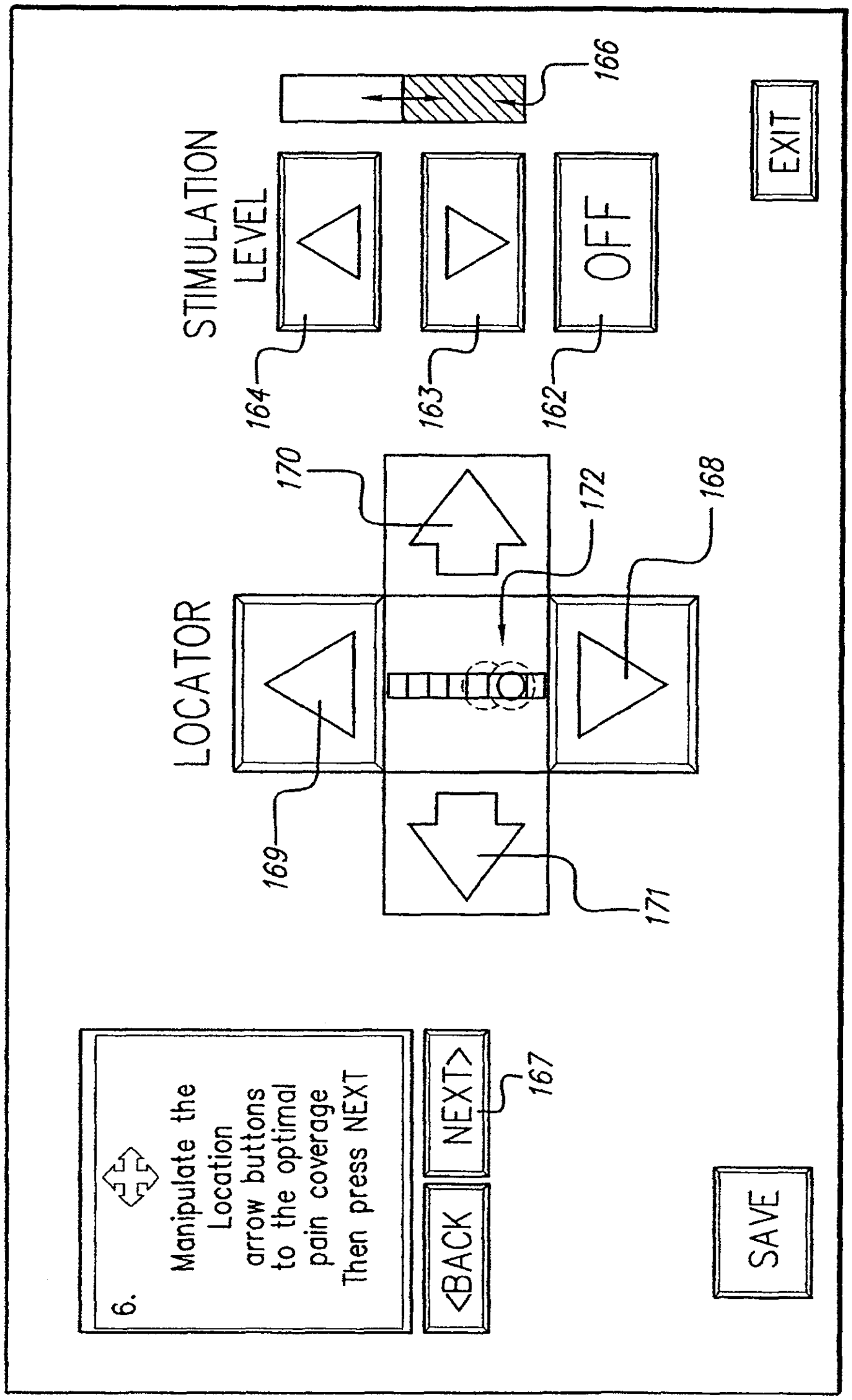

Once an adequate number of threshold measurements have been made (FIG. 11, blocks 134, 136, 138), the user is instructed to manipulate the location arrow buttons to determine an optimal pain coverage. This step is done, in one embodiment, by displaying a locator screen as shown in FIG. 12D. The locator screen includes, on its right side, controls for the stimulation level, including an ON/OFF button 162, increase button 164, decrease button 163, and stimulation level bar graph indicator 166, much the same as, or similar to, those shown in FIGS. 12B and 12C. Also included within the locator screen seen in FIG. 12D, in addition to specific instructions in the upper left hand corner, is an up arrow button 169, a down arrow button 168, a left horizontal arrow button 171 and a right horizontal button 171. The screen shown in FIG. 12D assumes that only an in-line electrode is used, hence only the up button 169 and the down button 168 are activated. (For electrode arrays that allow horizontal movement, the right and left buttons 170 and 171 would also be activated.) As these locator buttons are pressed, the effective stimulation site, schematically illustrated at area 172 in the center of the locator buttons, shifts up or down the electrode. Hence, through use of the locator buttons 168, 169, 170 and/or 171, the user is able to zero in on an optimal pain coverage location.

Figure 12E:
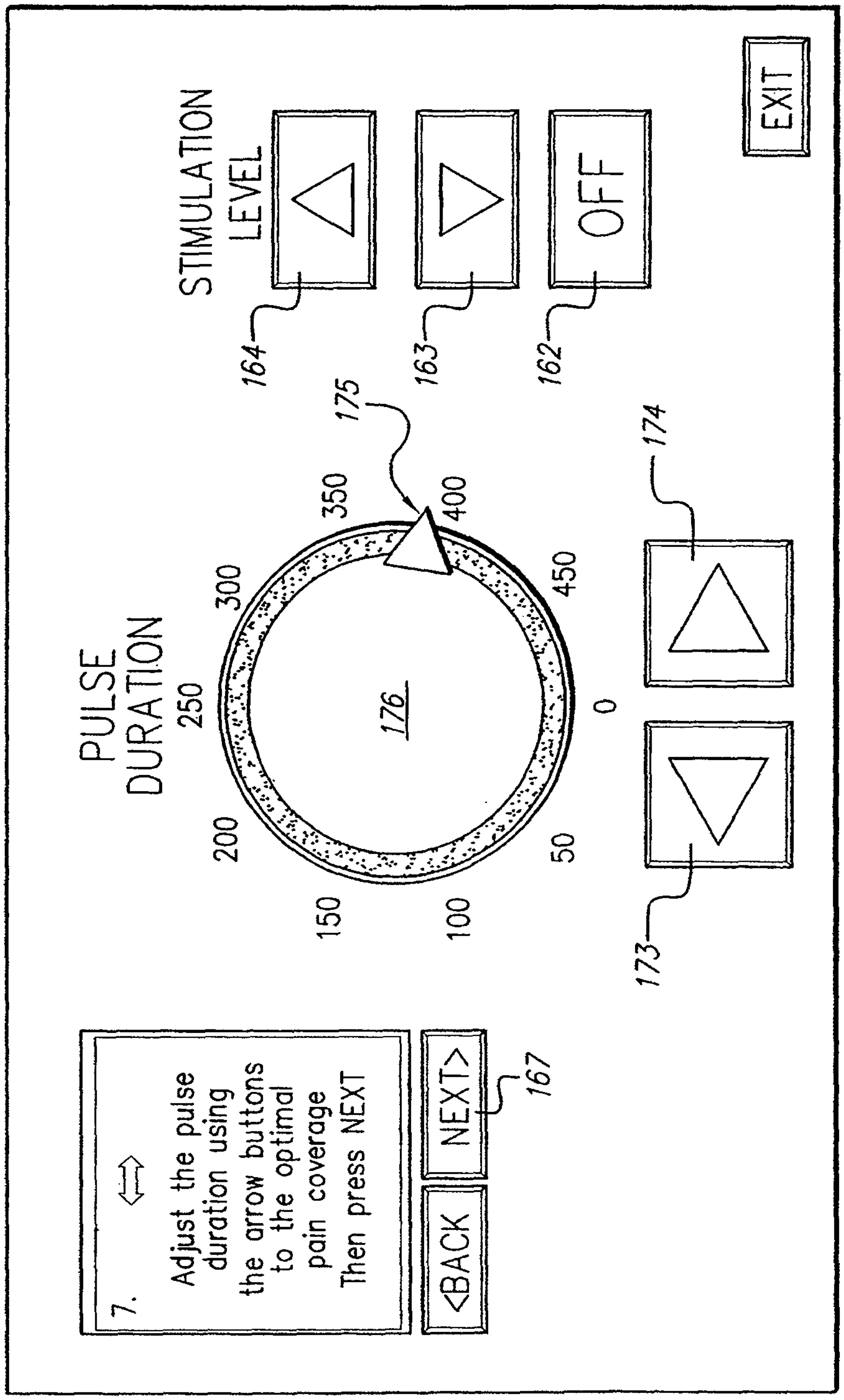

Once the user has located the optimal pain coverage location for the selected channel, the pulse duration is selected (FIG. 11, block 142). To assist the user in selecting the pulse duration, in one embodiment, a pulse duration screen is displayed as shown in FIG. 12E. Such pulse duration screen includes instructions in the upper left hand corner of the screen, and stimulation level controls 162, 163, and 164 on the right side of the screen, similar to the previously-described wizard screen of FIG. 12D. The pulse duration screen further includes arrow buttons 173 and 174 which, when clicked, allow the user to decrease or increase the stimulation pulse width. As adjustments to the stimulation pulse width are made, an analog knob 176, having a pointer 175, rotates to the location indicative of the selected pulse width. For the selection shown in FIG. 12E, the pulse width is approximately 390 microseconds. As an alternative to increasing and decreasing the pulse width using the arrow buttons 173 and 174, the user may also simply click and hold the mouse cursor on the knob 76, and then by moving the cursor, cause the knob to rotate to a desired pulse width selection.

Figure 12F:
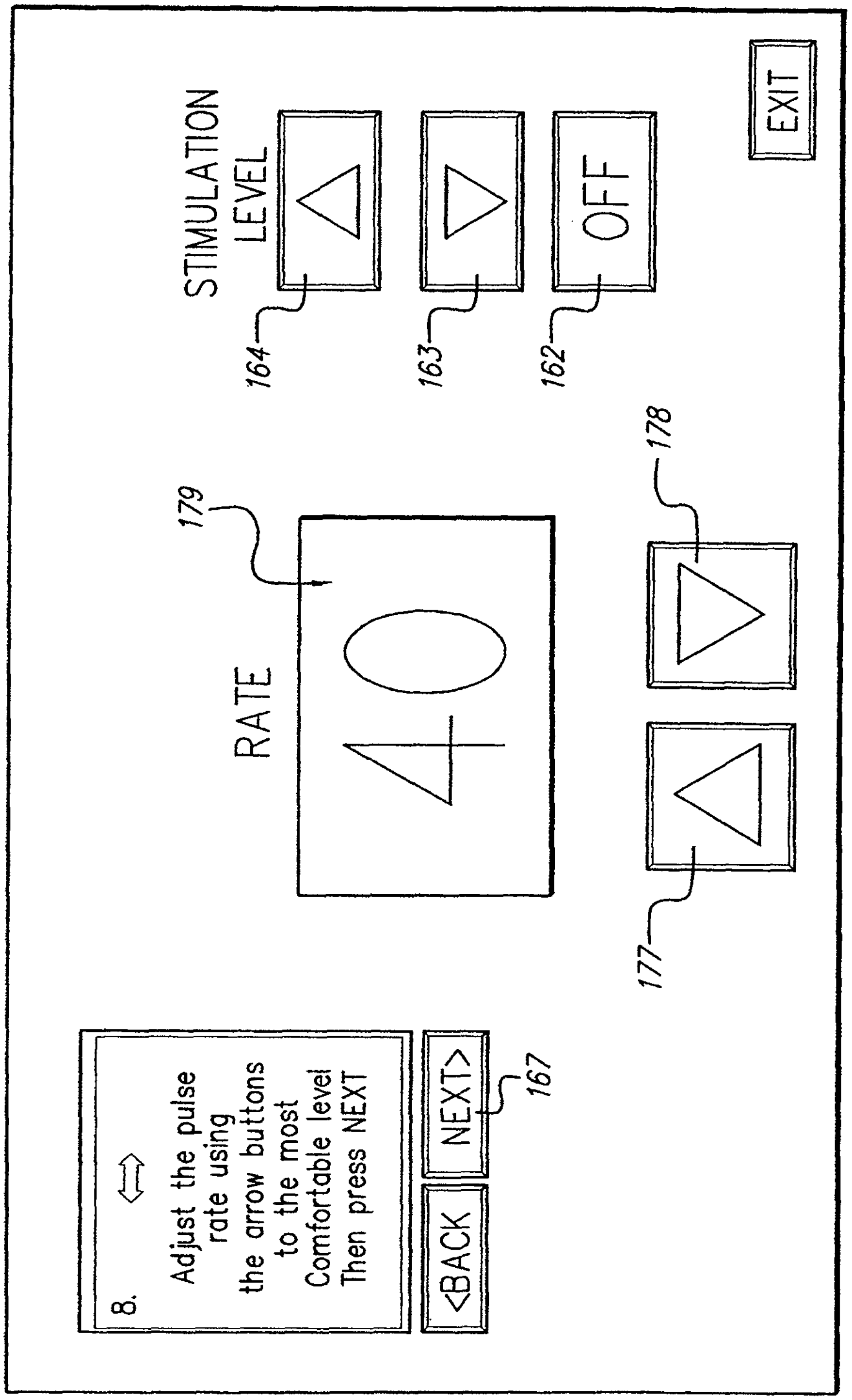

Once the pulse duration, or pulse width, has been set, the next step is to select the pulse rate (FIG. 11, block 144). In one embodiment of the invention, this step is prompted by displaying a rate screen as shown in FIG. 12F. Such pulse rate screen includes instructions in the upper left hand corner of the screen, and stimulation level controls 162, 163, and 164 on the right side of the screen, similar to the previously-described wizard screens of FIGS. 12D and 12E. The pulse rate screen further includes arrow buttons 177 and 178 which, when clicked, allow the user to decrease or increase the stimulation pulse rate. The rate selected is displayed as a number in the area 179. For the rate screen shown in FIG. 12F, the rate has been set to 40 pulses per second (pps). Once the rate has been set to a most comfortable level, the NEXT button 167 is clicked in order to advance to the next step of the fitting process.

Figure 12G:
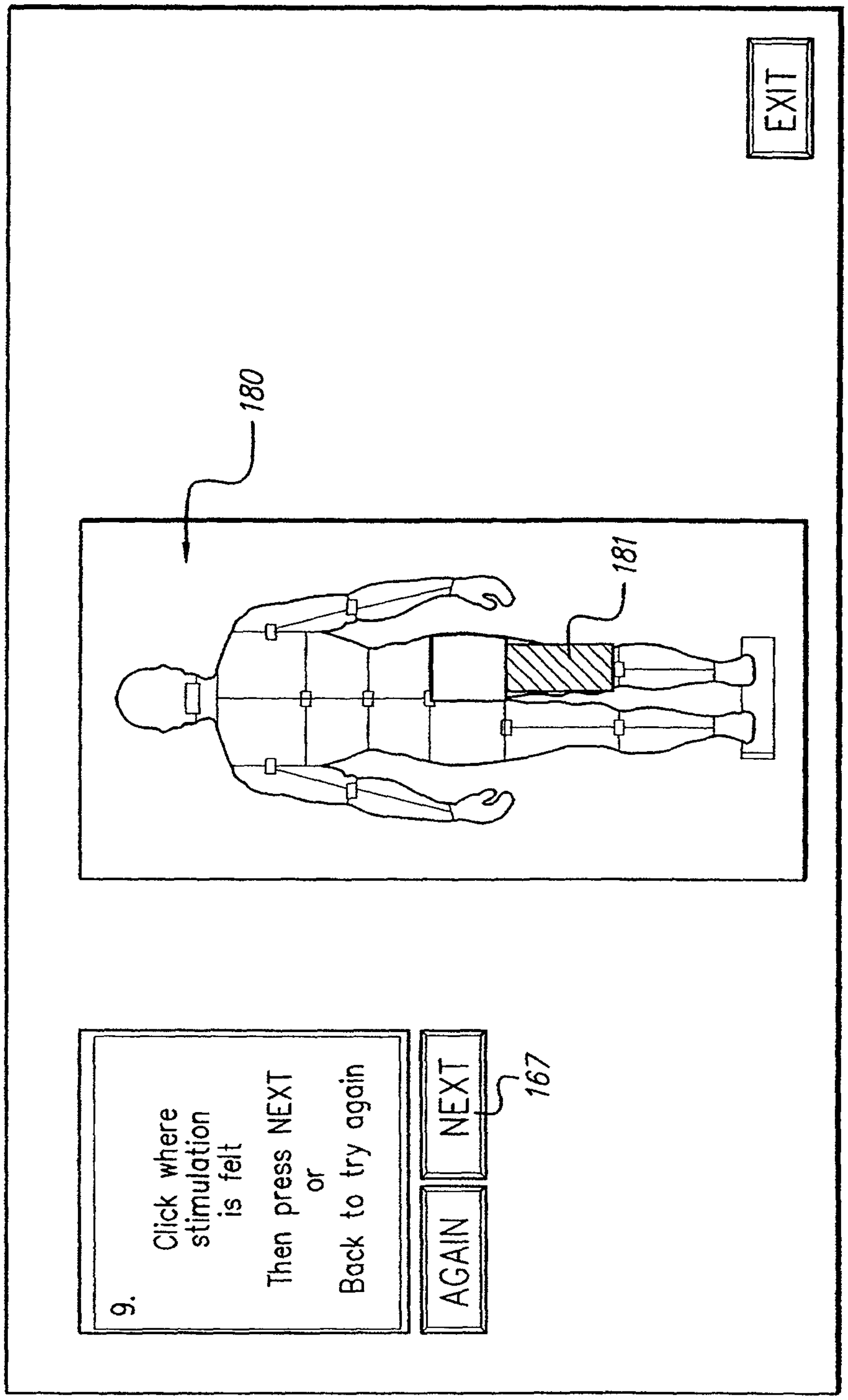

The next step of the fitting process, as shown in the flow diagram of FIG. 11, comprises defining where the stimulation is felt (block 146). This process is facilitated by displaying a patient FIG. 180 as illustrated in FIG. 12G. Once the FIG. 180 has been displayed, one area 181 of the patient FIG. 180 is selected as the area where the patient feels stimulation. While the area 181 is shown in FIG. 12G as cross-hatched, such is shown only for purposes of illustration in a black and white drawing. Typically, the area 181 changes to a different color, e.g., red, yellow, blue or green, when selected.

Figure 12H:
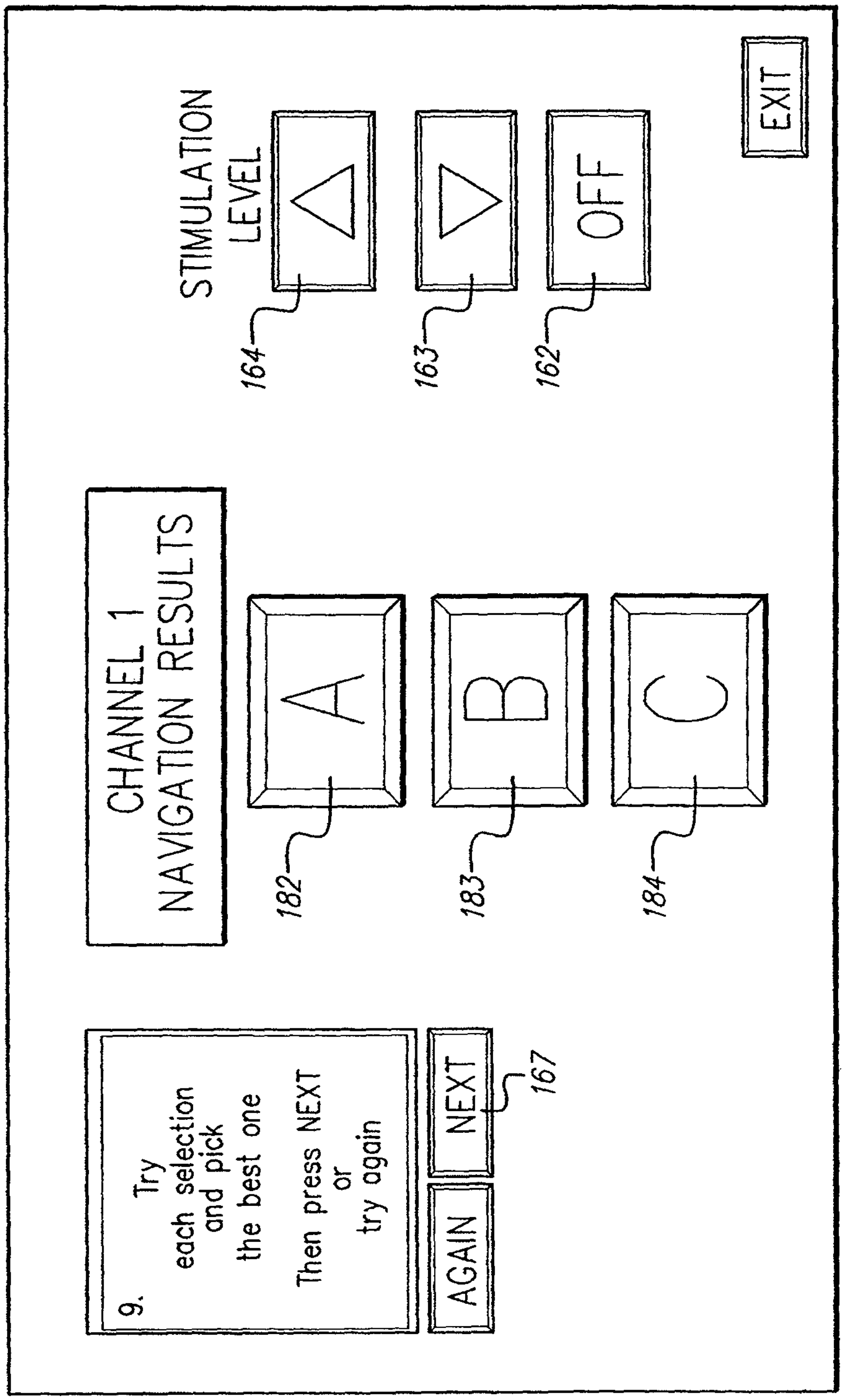

As part of step of selecting where stimulation is felt, some embodiments of the invention further allow the user to select one of up to three different stimulation settings as the best setting for that channel. Such selection is facilitated by displaying a navigation results screen as depicted in FIG. 12H. The navigation results screen shown in FIG. 12H includes instructions in the upper left hand corner of the screen, and stimulation level controls 162, 163, and 164 on the right side of the screen, similar to the previously-described wizard screens of FIGS. 12D, 12E and 12F. Also included are three selection buttons 182, 183 and 184, labeled "A", "B" and "C" in FIG. 12H. Selection button "A" (button 182) selects a first set of stimulation parameters; selection button "B" (button 183) selects a second set of stimulation parameters; and selection button "C" (button 184) selects a third set of stimulation parameters. These different sets of stimulation parameters may be derived from the threshold measurements (FIG. 11. blocks 134, 136), the location manipulator adjustments (FIG. 11, block 140), and/or the pulse duration (FIG. 11, block 142) and pulse rate selections (FIG. 11, block 144) previously made, or previously selected by the user. The ability to select a "best" set of stimulation parameters in this manner offers the user the chance to "feel" and "compare" stimulations based on differing sets of stimulation parameters in close proximity in time. In this regard, the selection offered in the navigation results screen of FIG. 12H is similar to the choice an optometrist or ophthalmologist offers a patient while testing vision when he/she asks the patient "which looks better, A, B or C?" as different lenses are switched in and out of the viewer through which the patient views an eye chart.

Figure 12J:
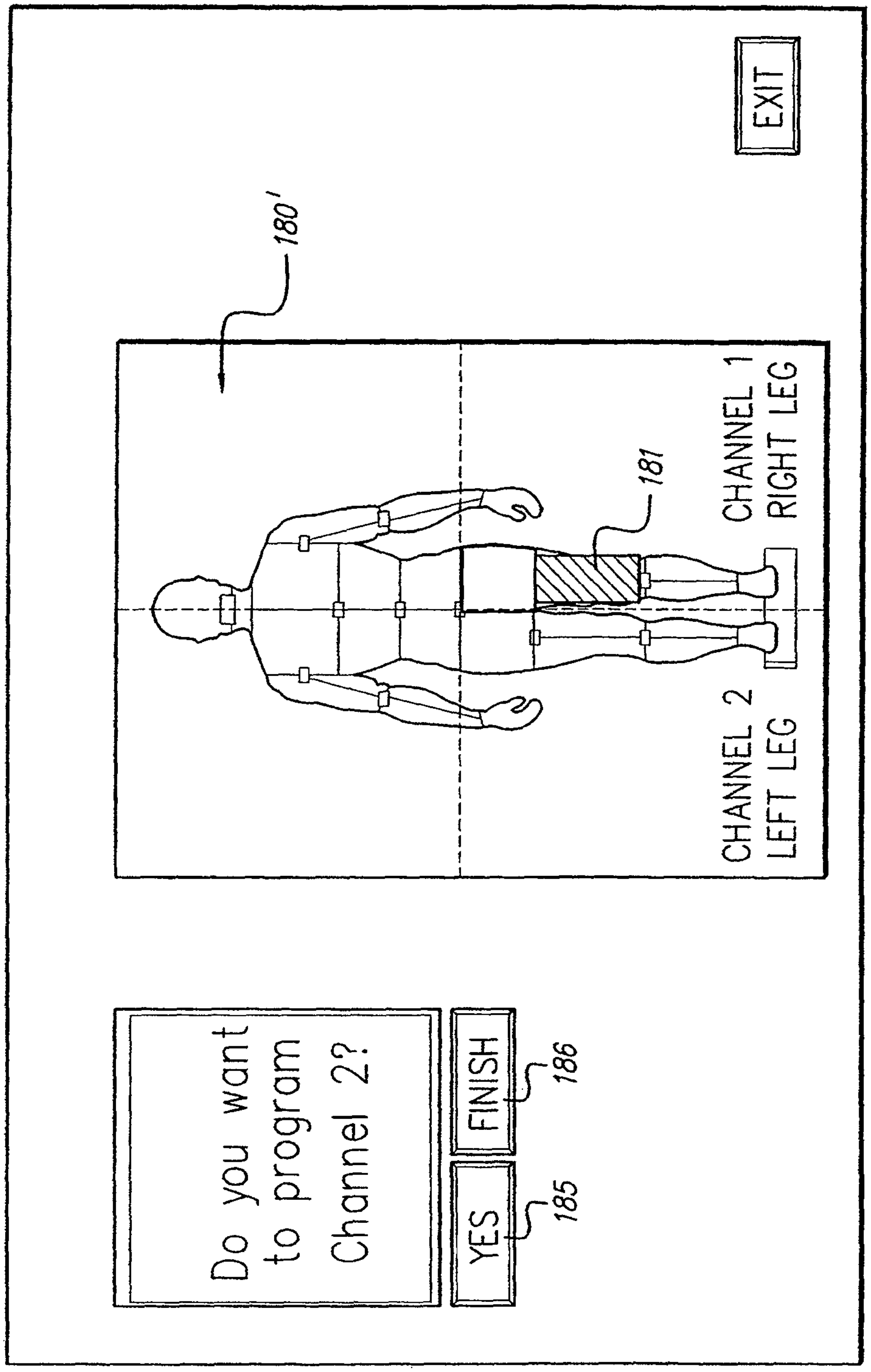

After the user has selected the "best" selection of stimulation parameters for the given channel (FIG. 11, block 148), he or she is offered the choice to program additional channels (FIG. 11, block 150). In one embodiment, such choice is presented by way of a prompt screen such as the screen depicted in FIG. 12J. Such prompt screen asks the user whether he or she wants to program another channel, e.g., channel 2 (see upper left hand corner), while presenting a display of the patient's body 180' wherein the other channel to be programmed is defined. For the situation represented in FIG. 12J, channel 1 comprises stimulation pulses applied to, or felt in, the right leg; while channel 2 comprises stimulation pulses applied to, or felt in, the left leg. If the user does want to program another channel, e.g., channel 2, then he or she clicks on a YES button 185. If the user does not want to program another channel, then he or she clicks on the FINISH button 186.

Figure 13:
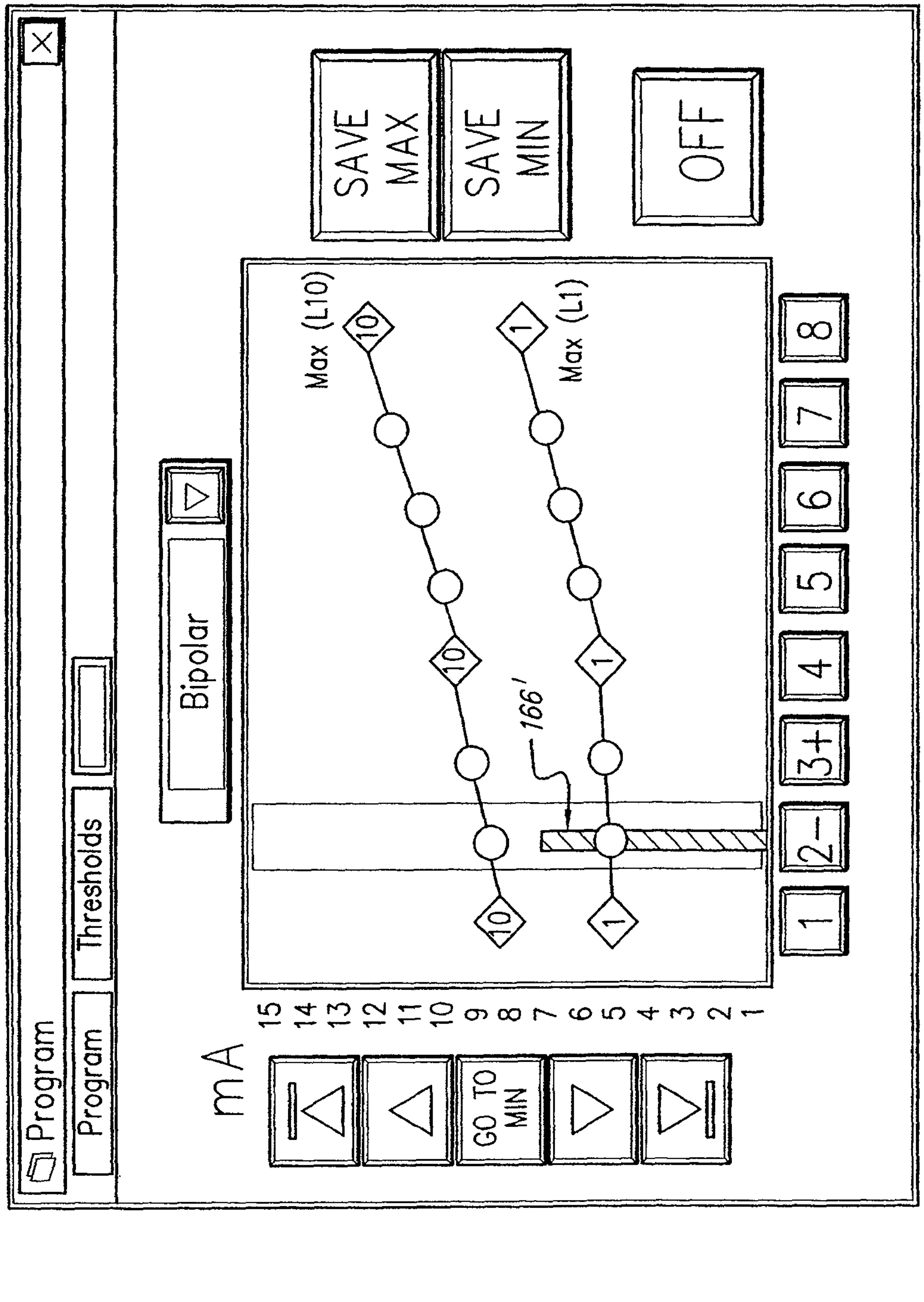
FIG. 13 illustrates a representative measurement screen used as a part of the fitting process which graphically shows the measured and calculated threshold settings.

Should the user indicate that he or she is finished, by clicking the FINISH button 186, then the user is provided the opportunity to review and/or verify the program settings that have been made (FIG. 11, block 152). Such verification and review, in one embodiment, allows the user to select, inter alia, a chart, as shown in FIG. 13, that graphically displays the normalized settings as a function of each electrode position. As seen in FIG. 13, for example, the minimum perceived threshold (level 1) is illustrated for all 8 electrodes. The minimum perceived threshold was measured only for electrodes E1, E4 and E8, and from these measurements the minimum perceived threshold was calculated using interpolation for the remaining electrodes E2, E3, E5, E6 and E7. Similarly, the maximum comfortable threshold was measured only for electrodes E1, E4 and E8, and from these measurements the maximum comfortable threshold was calculated using interpolation for the remaining electrodes E2, E3, E5, E6 and E7. The program settings screen shown in FIG. 13 further shows that electrode E2 is selected as the cathodic (−) electrode, with electrode E3 selected as the anodic (+) electrode, and with the stimulation current level being represented as a vertical bar 166'. Such vertical bar 166' shows that for the settings represented in FIG. 13, the stimulation level on electrode E2 is approximately half way (level 5 or 6) between the minimum (level 1) and maximum (level 10) amplitude settings. The chart in FIG. 13 also shows that a level 1 stimulation level on electrode E2 corresponds to a stimulation current amplitude of about 5 ma, while a level 10 stimulation level on electrode E2 corresponds to a stimulation current having an amplitude of about 8.5 ma. Other buttons include in FIG. 13 allow other settings to be verified, adjusted, or saved, in conventional manner.

Figure 14:
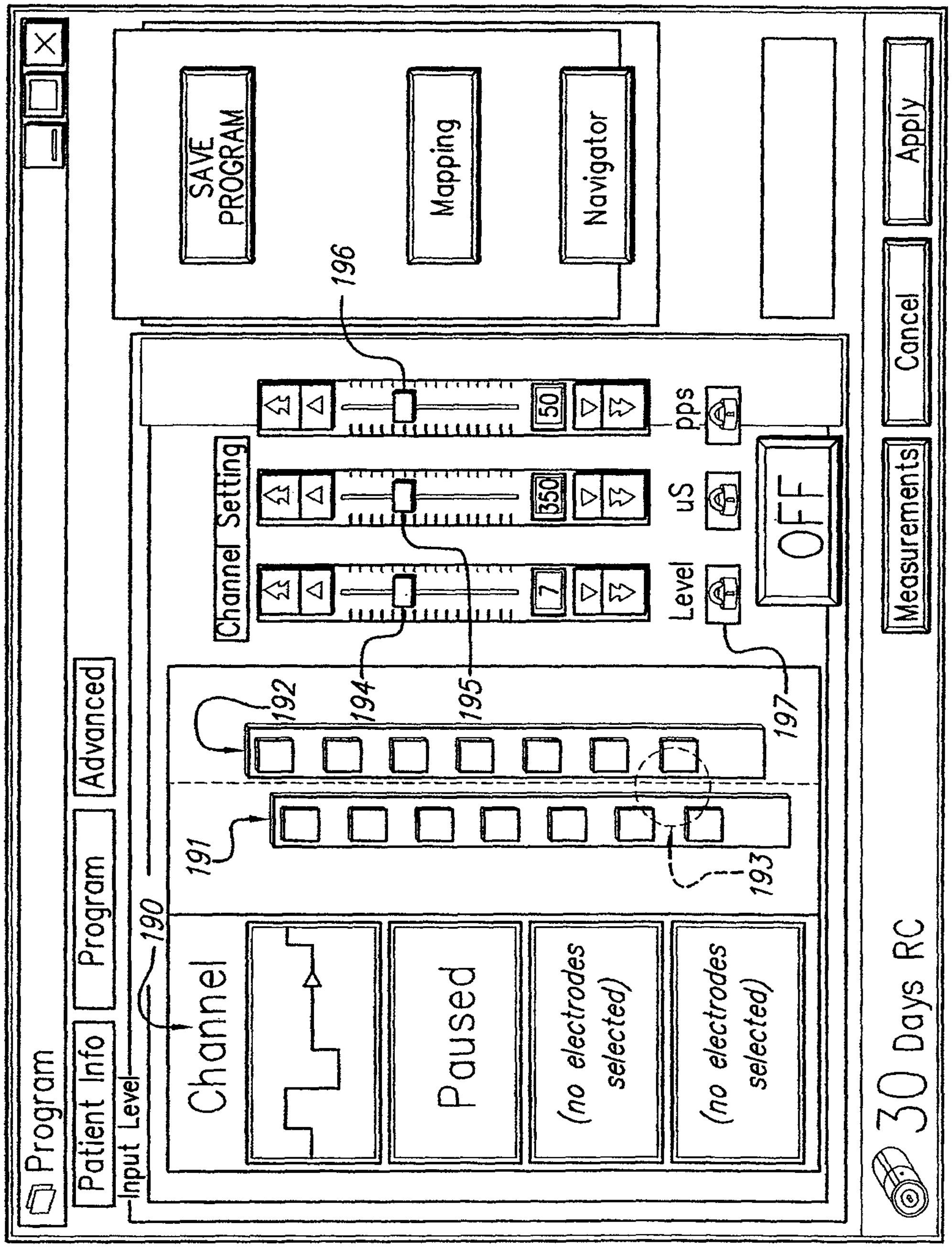
FIG. 14 illustrates a representative programming screen used as part of the fitting process carried out by the software wizard of FIG. 11.

Other of the data that may be reviewed and adjusted or modified, as desired (FIG. 11, block 152), includes the parameter settings as summarized, e.g., on the screen shown in FIG. 14. Included in such parameter setting display is a schematic representation 190 of the channels on the left side of the screen. In the preferred embodiment, up to four independent channels may be provided by the SCS system. For the condition represented by the parameter settings in FIG. 14, only one channel is active (the one at the top of the channel windows, and it is programmed to provide a biphasic pulse). One of the channels is paused, and two of the channels have no electrodes selected, which means these channels are inoperable for this setting.

The parameter settings represented in FIG. 14 also include a schematic representation of the electrode array. For the conditions represented by FIG. 14, two side-by-side in-line electrode arrays 191 and 192 are used, with staggered electrodes. The stimulation site selected is near the bottom of the arrays, as oriented in FIG. 14. The parameter settings associate with the active channel are also represented in FIG. 14, and may readily be adjusted, if needed. As seen in FIG. 14, the stimulation level is set to "7", the pulse width (or duration) is set to 350 psec, and the stimulation rate is set to 50 pps. Any of these values may be readily adjusted by simply clicking on to the respective slide bars 194, 195 or 196 and moving the bar in one direction or the other. Before such values can be adjusted, they must be unlocked, by clicking on the respective locked icon 197 at the bottom of the slide bar. Unlocking these values for adjustment may, in some embodiments, require a password.

Figure 15:
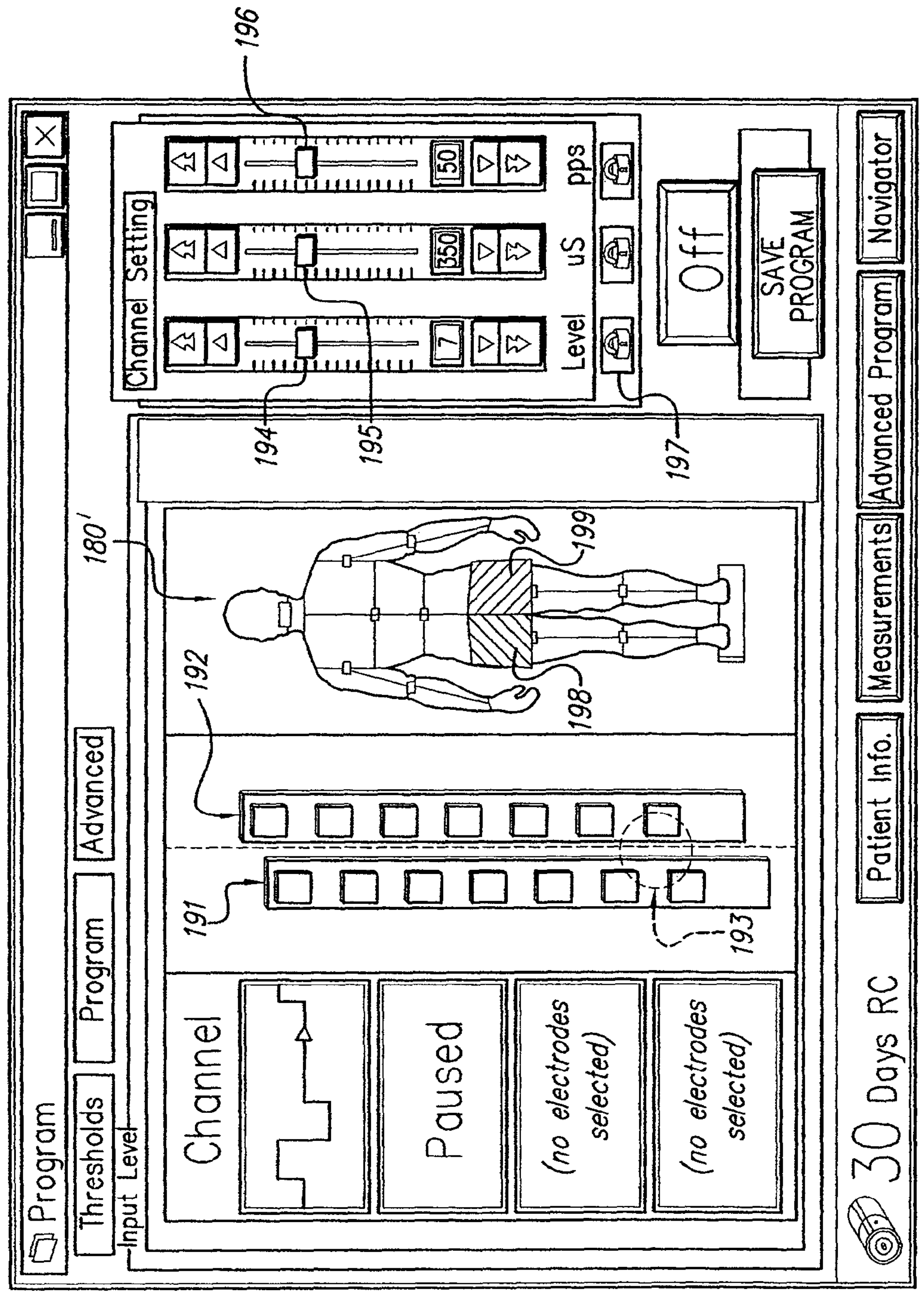
FIG. 15 similarly illustrates a representative programming screen used as part of the fitting process.

FIG. 15 illustrates another type of screen that may be displayed as the channel settings are reviewed and/or modified. For the most part, the screen shown in FIG. 15 contains much of the same information as is included in FIG. 14. However, FIG. 15 further includes a patient display 197 that allows selected areas on the patient, e.g., areas 198 and/or 199, to be selected for receiving stimulus pulses.

Figure 16:
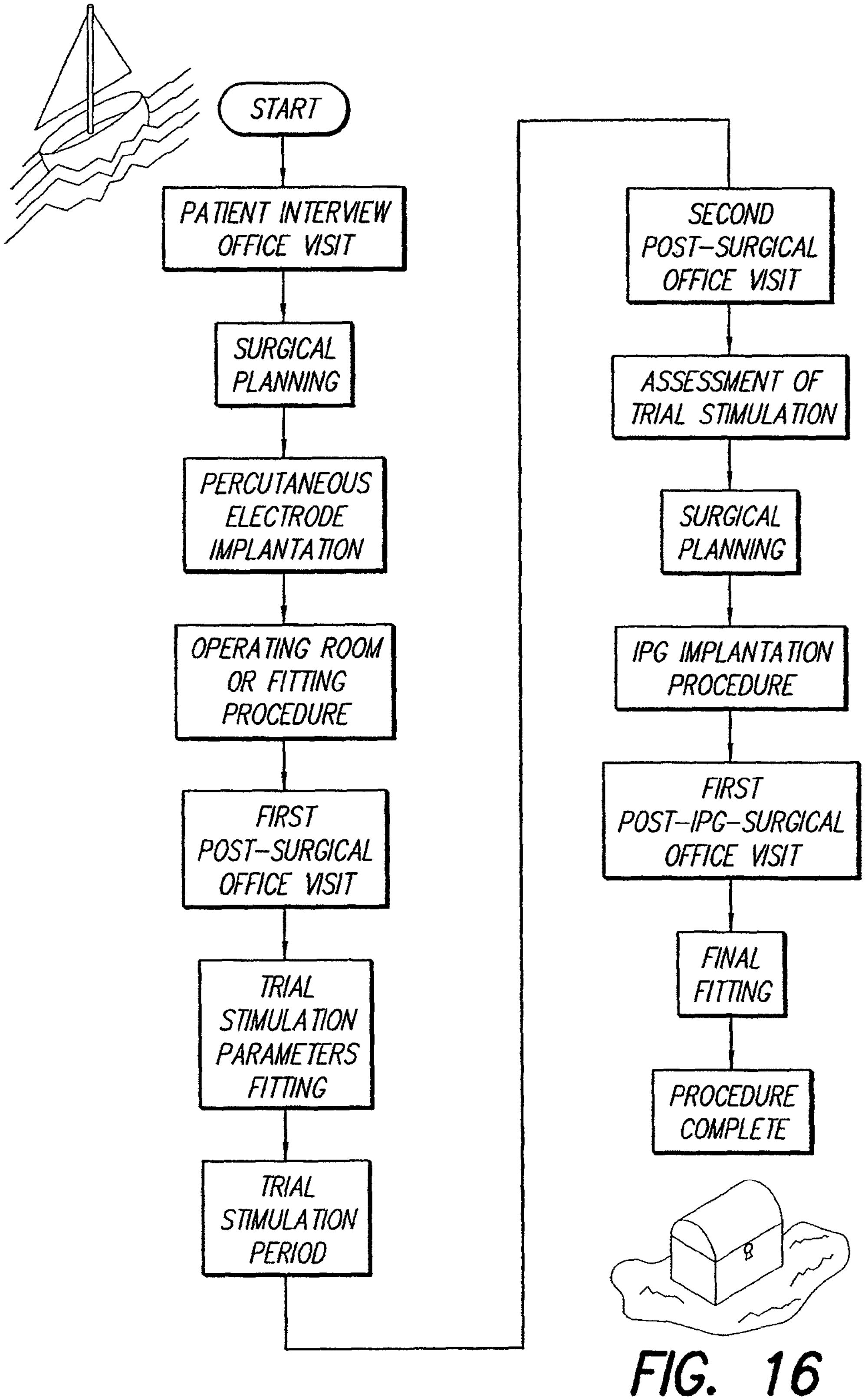
FIG. 16 shows an illustrative navigator map that may be used with the fitting system of the present invention in order to teach and guide the patient through the complete fitting process.

Next, with respect to FIG. 16, a representation of a treasure map is displayed, which map may be used, in some embodiments of the invention, to aid the clinician and patient as the fitting process is carried out. The treasure map depicted in FIG. 16 highlights the path the patient must follow to achieve a successful fitting of his or her SCS system, represented by a treasure chest, the ultimate goal of following the map. The treasure map shown in FIG. 16 may be displayed on the screen 16 of the programming device 10 (see FIG. 1A) and/or printed as a fold-out map. Eye-catching illustrations may be positioned at various locations on the map, such as a sail boat carrying a trained, faithful and talented crew of clinicians and other medical personnel to assure that the patient stays on course on route to the treasure. Other fun and interesting information (not shown in FIG. 16) may also be included on the map. When shown on a display screen, each of the main blocks, or steps, included on the path to the treasure chest, may flash or be lighted or change color as these steps are traversed by the patient. Sound bites may also be interspersed at key locations along the path to the treasure to educate and entertain.

As is evident from FIG. 16, the fitting process involves much more than a single visit from the patient with the clinician. Rather, numerous steps must be traversed, in a prescribed sequence, in order for the fitting to be successful. These steps are described more fully in the previously referenced '829 provisional patent application. As seen in FIG. 16, at least the following steps lie along the path to reach the treasure—a successful fitting and a happy patient—: (1) a patient interview office visit; (2) surgical planning; (3) percutaneous electrode Implantation; (4) operating room (OR) fitting procedure; (5) First Post-surgical office visit; (6) trial stimulation parameters fitting; (7) trial stimulation period; (8) second post-surgical office visit; (9) assessment of trial stimulation; (10) surgical planning; (11) IPG (implantable pulse generator) procedure; (12) First Post-IPG-Surgical Office Visit; and (13) final fitting.

As described above, it is thus seen that the present invention provides numerous functions and meets various needs. These functions and needs include the following:

1. A programming system using an input device and control logic (by software, hardware, or electrical design) to continuously configure electrodes and current distributions in response to the user controlled input device.
2. A method of stimulating where current shifting and electrode configurations are determined in response to an input mechanism controlled by the user, that interprets the shifting based on a table, formula, or mathematical model.
3. A programming method where reconfiguring electrodes is achieved without stopping stimulation to select the next configuration to be tested.
4. A programming method where reconfiguring electrodes (or current shifting) is achieved without stopping stimulation to select the next configuration to be tested:
   A. Using a table based approach (preset list of possible sequences).
   B. Using a "solve for" equation (or a mathematical model).
5. A neural stimulating system where electrodes can have current split to unequal and independently determined levels on a single channel.
6. A neural stimulating system wherein a threshold/maximal range is used to normalize amplitude levels in a current summation process to determine the amount of current that should be applied on a given electrode in a group based on a given "level".
7. A method for changing electrode configurations and current levels on selected electrodes of a neural stimulating system while maintaining a relative intensity perception of the stimulation.
8. A patient useable take-home programmer that interprets normalized levels to proportionately increase or decrease amplitude on the programmed group of electrodes, thereby ensuring that the patient cannot exceed the maximum tolerable level.
9. A method of programming where any change in distribution can be implemented in the smallest obtainable change in stimulation parameters on adjacent electrodes.
10. A method of programming where a transition from one distribution of current or voltage amplitudes X={$x_1$, $x_2$, . . . , $x_n$} on n electrodes to a second distribution of current or voltage amplitudes Y={$y_1$, $y_2$, . . . $y_n$} such that $$\sum_{i=1}^{n} (xi - yi)^2 < \text{Maximum of} \left[ \sum_{i=1}^{n} (x_i - y_i)^2 \right]$$

11. A system that must use the maximal resolution available to the system at all points of its operation parameters, i.e. a 16 bit DAC system must use 16 bit resolution.
12. A user interface useable in a neural stimulation system that visually represents the changing current field.
13. A user interface useable in a neural stimulation system that uses consecutive windows in a "wizard" process to step the user through each step in the fitting process.
14. A system that allows a clinician and the patient to quickly determine the desired electrode stimulation pattern, including which electrodes of a multiplicity of electrodes in an electrode array should receive a stimulation current, including the amplitude, width and pulse repetition rate of such current, so that the tissue stimulator can be programmed with such information.
15. An electrode selection/programming system that allows the clinician to readily select and visualize a particular group of electrodes of an electrode array for receipt of a stimulation pulse current, and/or to allow different combinations of pulse amplitude, pulse width, and pulse repetition rates to be applied to the selected group.
16. A system that facilitates the programming of an implantable tissue stimulator, having an array of stimulation electrodes attached thereto, so that only those electrodes which prove most effective for a desired purpose, e.g., pain relief, are selected to receive a pulsed current having an amplitude, width and repetition frequency that best meets the needs of a particular patient.

While the invention herein disclosed has been described by means of specific embodiments and applications thereof, numerous modifications and variations could be made thereto by those skilled in the art without departing from the scope of the invention set forth in the claims.

What is claimed is:

1. A programmer for a tissue stimulator that generates a stimulation field adjacent an array of electrodes, comprising:

a user-controlled input device configured for generating control signals;

a processor configured for generating stimulation parameter values that can be used by the tissue stimulator to modify the stimulation field adjacent the electrodes, the processor further configured for generating display signals that can be used to display the modified stimulation field, the displayed modified stimulation field comprising at least one line surrounding at least a portion of selected ones of the electrodes;

control circuitry configured for generating programming signals containing the stimulation parameter values; and a transmitter configured for transmitting the programming signals to the tissue stimulator.

2. The programmer of claim 1, further comprising a monitor configured for displaying the modified stimulation field relative to the electrodes.

3. The programmer of claim 1, wherein the line is dashed.

4. The programmer of claim 1, wherein the stimulation parameter values are stimulus current values.

5. The programmer of claim 4, wherein the processor is configured for shifting the stimulus current values between the electrodes in response to the control signals.

6. The programmer of claim 1, wherein the transmitter is a wireless transmitter.

7. The programmer of claim 1, wherein the user-controlled input device comprises a joystick.

8. The programmer of claim 1, wherein the tissue stimulator is an implantable pulse generator.

9. The programmer of claim 1, wherein the at least one line encircles the selected electrodes.

10. The programmer of claim 1, wherein the at least one line completely surrounds the selected electrodes.

11. The programmer of claim 1, wherein the electrodes are configured for being implanted adjacent a spinal cord of a patient, such that the stimulation field stimulates the spinal cord, and the processor is configured for generating the display signals that can be used to display the modified stimulation field that stimulates the spinal cord.

12. The programmer of claim 1, wherein the processor is configured for generating the display signals as the stimulation field is modified.

13. A tissue stimulation system, comprising:

an implantable array of electrodes;

an external programmer configured for generating programming signals in response to user input to modify a stimulation field generated adjacent the electrodes, the external programmer further configured for prompting a monitor to display the modified stimulation field, the displayed modified stimulation field comprising at least one line surrounding at least a portion selected electrodes; and a tissue stimulator configured for receiving the programming signals and generating the modified stimulation field adjacent the electrodes in accordance with the programming signals.

14. The system of claim 13, further comprising a display configured for displaying the modified stimulation field.

15. The system of claim 13, wherein the line is dashed.

16. The system of claim 13, wherein the tissue stimulator is configured for steering current-controlled stimulation energy between the electrodes in accordance with the programming signals.

17. The system of claim 13, wherein the external programmer is configured for wirelessly transmitting the programming signals to the tissue stimulator.

18. The system of claim 13, wherein the external programmer includes a user-controlled input device for receiving the user input.

19. The system of claim 18, wherein the user-controlled input device comprises a joystick.

20. The system of claim 13, wherein the tissue stimulator is an implantable pulse generator.

21. The system of claim 13, wherein the at least one line encircles the selected electrodes.

22. The of claim 13, wherein the at least one line completely surrounds the selected electrodes.

23. The system of claim 13, wherein the electrodes are configured for being implanted adjacent a spinal cord of a patient, such that the stimulation field stimulates the spinal cord, and the external programmer is configured for generating the display signals that can be used to display the modified stimulation field that stimulates the spinal cord.

24. The system of claim 13, wherein the external programmer is configured for generating the display signals as the stimulation field is modified.

* * * * *